(12) United States Patent
Ellis-Behnke et al.

(10) Patent No.: US 9,415,084 B2
(45) Date of Patent: Aug. 16, 2016

(54) TREATMENT OF LEAKY OR DAMAGED TIGHT JUNCTIONS AND ENHANCING EXTRACELLULAR MATRIX

(75) Inventors: Rutledge Ellis-Behnke, Canton, MA (US); Terrence W. Norchi, Natick, MA (US); Stephen Richard Kelly, Manchester, MA (US)

(73) Assignee: Arch Biosurgery, Inc., Cambridge, MA (US)

( * ) Notice: Subject to any disclaimer, the term of this patent is extended or adjusted under 35 U.S.C. 154(b) by 507 days.

(21) Appl. No.: 12/049,190

(22) Filed: Mar. 14, 2008

(65) Prior Publication Data

US 2008/0274979 A1 Nov. 6, 2008

Related U.S. Application Data

(60) Provisional application No. 60/894,872, filed on Mar. 14, 2007.

(51) Int. Cl.
| | |
|---|---|
| *A61K 38/10* | (2006.01) |
| *A61K 38/07* | (2006.01) |
| *A61K 38/08* | (2006.01) |
| *C07K 5/103* | (2006.01) |
| *C07K 7/06* | (2006.01) |

(52) U.S. Cl.
CPC .................. *A61K 38/07* (2013.01); *A61K 38/08* (2013.01); *A61K 38/10* (2013.01); *C07K 5/1008* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 4,098,728 | A | 7/1978 | Rosenblatt |
| 4,211,227 | A | 7/1980 | Anderson et al. |
| 4,272,398 | A | 6/1981 | Jaffe |
| 4,636,208 | A | 1/1987 | Rath |
| 4,829,000 | A | 5/1989 | Kleinman |
| 4,861,627 | A | 8/1989 | Mathiowitz et al. |
| 5,019,646 | A | 5/1991 | Furcht |
| 5,180,375 | A | 1/1993 | Feibus |
| 5,192,302 | A | 3/1993 | Kensey et al. |
| 5,222,974 | A | 6/1993 | Kensey |
| 5,645,565 | A | 7/1997 | Rudd |
| 5,670,483 | A | 9/1997 | Zhang et al. |
| 5,955,343 | A | 9/1999 | Holmes et al. |
| 6,333,194 | B1 | 12/2001 | Levy et al. |
| 6,368,877 | B1 | 4/2002 | Zhang et al. |
| 6,548,630 | B1 | 4/2003 | Zhang et al. |
| 6,663,655 | B2 | 12/2003 | Ginn |
| 6,711,879 | B2 | 3/2004 | Korteweg et al. |
| 6,800,116 | B2 | 10/2004 | Stevens et al. |
| 6,800,481 | B1 | 10/2004 | Holmes et al. |
| 6,844,324 | B1 | 1/2005 | Zhang et al. |
| 6,953,656 | B2 | 10/2005 | Jacobson et al. |
| 6,953,659 | B2 | 10/2005 | Jacobson et al. |
| 7,098,028 | B2 | 8/2006 | Holmes et al. |
| 7,179,784 | B2 | 2/2007 | Zhang et al. |
| 7,449,180 | B2 | 11/2008 | Kisiday et al. |
| 2002/0072074 | A1 | 6/2002 | Zhang et al. |
| 2002/0160471 | A1 | 10/2002 | Kisiday |
| 2003/0176335 | A1 | 9/2003 | Zhang et al. |
| 2004/0011201 | A1 | 1/2004 | Stevens |
| 2004/0023414 | A1 | 2/2004 | Zhang et al. |
| 2004/0087013 | A1 | 5/2004 | Holmes et al. |
| 2004/0204561 | A1 | 10/2004 | Ellison |
| 2004/0242469 | A1 | 12/2004 | Lee et al. |
| 2005/0287186 | A1 | 12/2005 | Ellis-Behnke et al. |
| 2006/0019309 | A1 | 1/2006 | Zhang et al. |
| 2006/0025524 | A1 | 2/2006 | Schneider et al. |
| 2006/0084607 | A1* | 4/2006 | Spirio ............... A61K 9/0019 514/21.4 |
| 2006/0088510 | A1 | 4/2006 | Lee et al. |
| 2006/0148703 | A1 | 7/2006 | Lee et al. |
| 2006/0199778 | A1 | 9/2006 | Ellis-Behnke et al. |
| 2006/0211615 | A1 | 9/2006 | Zhang et al. |
| 2007/0203062 | A1 | 8/2007 | Ellis-Behnke |
| 2007/0287741 | A1* | 12/2007 | Herzberg et al. ............. 514/420 |
| 2008/0032934 | A1 | 2/2008 | Ellis-Behnke et al. |
| 2008/0091233 | A1 | 4/2008 | Ellis-Behnke et al. |

(Continued)

FOREIGN PATENT DOCUMENTS

| | | |
|---|---|---|
| WO | WO 95/09659 | 4/1995 |
| WO | WO 98/58967 | 12/1998 |

(Continued)

OTHER PUBLICATIONS

Adler, "Self-assembling gel stops bleeding in seconds", *New Scientist Tech*, 1(3):117 (Oct. 10, 2006).
AlertNet, "Researches study liquid as tool to stop bleeding", www.alertnet.org, pp. 1, (Oct. 10, 2006).
Ball, "Brain Knitting", materials@nature.com, pp. 1-2 (2006).
Bansal, "Scientists develop liquid that could revolutionize bleeding control", *All Headline News*, pp. 1 (2006).
Barone, "Nanoliquid stops bleeding practically in a nanosecond", *Discover Magazine*, pp. 1 (Feb. 25, 2007), accessed Dec. 22, 2007.
BBC News, "Liquid to seal open wounds fast", www.newsvote.bbc.co.uk, pp. 1-3, (Oct. 14, 2006), accessed Jul. 10, 2009.
Benita, et al., "Characterization of drug-loaded poly(d,l-lactide) microspheres", *J. Pharm. Sci.*, 73(12):1721-4 (1984).

(Continued)

*Primary Examiner* — Maury Audet
(74) *Attorney, Agent, or Firm* — Pabst Patent Group LLP

(57) ABSTRACT

Self assembling peptides and peptidomimetics can be utilized for the treatment and support of disorders associated with leaky or damaged tight junction and weak, diseased, or injured extracellular matrix. The self-assembling materials generally have alternating hydrophilic or hydrophobic residues or hydrophobic and/or hydrophilic sections which allow the material to react or interact with the glycoproteins found in the ECM. Diseases in which treatment with these materials applied to or near the site in need of treatment include diabetic retinopathy, sepsis, burns, and certain neurodegenerative diseases such as Parkinson's and Alzheimer's. The formulations can be administered by injection, spraying, topically or by catheter or via a wound dressing or other material to which it is applied and then applied to the site in need of treatment.

14 Claims, 5 Drawing Sheets

(56) References Cited

U.S. PATENT DOCUMENTS

| | | | |
|---|---|---|---|
| 2009/0111734 A1 | 4/2009 | Ellis-Behnke et al. | |
| 2012/0085262 A1 | 4/2012 | Klimov | |

FOREIGN PATENT DOCUMENTS

| | | |
|---|---|---|
| WO | WO 99/52574 | 10/1999 |
| WO | WO 02/062969 | 8/2002 |
| WO | WO 03/006043 | 1/2003 |
| WO | WO 03/084980 | 10/2003 |
| WO | WO 03/096972 | 11/2003 |
| WO | WO 2004/007532 | 1/2004 |
| WO | WO 2005/014615 | 2/2005 |
| WO | 2005123760 | 12/2005 |
| WO | WO 2006/014570 | 2/2006 |
| WO | 2006036826 | 4/2006 |
| WO | WO 2006/116524 | 11/2006 |
| WO | WO 2007/142757 | 12/2007 |
| WO | WO 2008/134544 | 11/2008 |

OTHER PUBLICATIONS

Bokhari, et al., "The enhancement of osteoblast growth and differentiation in vitro on a peptide hydrogel-polyHIPE polymer hybrid material", *Biomaterials*, 26(25):5198-208 (2005).

Bullis, "Nanohealing", *Technology Review*, pp. 1-3 (Mar./Apr. 2007).

"Conform" definition from http://www.merriam-webster.com/dictionary/conform, pp. 1-2. accessed Aug. 4, 2009.

Caplan, et al., "Control of self-assembling oligopeptide matrix formation through systematic variation of amino acid sequence", *Biomaterials*, 23(1):219-227 (2002).

Caplan, et al., "Self-assembly of a beta-sheet protein governed by relief of electrostatic repulsion relative to van der Waals attraction", *Biomacromolecules*, 1(4):627-631 (2000).

Christie, "The nano-knitters", *Popular Science*, pp. 1, accessed Aug. 11, 2006.

Crowston, et al., "New Optic Nerve? *International Glaucoma Review*", *The Journal for the Glaucoma Society*, (Meeting) Reports, pp. 1-2, (IGR 9-1 Jun. 2007).

Dahlberg, "Surgical discovery promising", *The Sacramento Bee*, pp. 1-3 (Oct. 10, 2006), accessed (Oct. 10, 2006).

Daily India, "Study: Biodegradable liquids halt bleeding", www.dailyindia.com; pp. 1, accessed Oct. 10, 2006.

Davis, et al., "Injectable self-assembling peptide nanofibers create intramyocardial microenvironments for endothelial cells", *Circulation*, 111(4):442-50 (2005).

Deutschlandfunk, "Liquid plaster", www.dradio.de; pp. 1-2, (Oct. 11, 2006), accessed (Oct. 12, 2006).

EJ, "Closing the cns gap", *ACS Chemical Biology*, 1(3):117, (2006).

Ellis-Behnke, et al., "Crystal clear surgery with self-assembling molecules that act as a bio barrier in the brain and intetstine", *Nanomedicine: Nanotechnology Biology and Medicine* 1(3):269-270 (2005).

Ellis-Behnke, et al., "Molecular repair of the brain using self-assembling peptides", *Chim. Oggi.*, 24(4) 42-45 (2006).

Ellis-Behnke, et al., "Molecular Restoration of the Body: Nano neuro knitting for brain repair", *JEAAM & BAAMJ*, 4:35-37 (2006).

Ellis-Behnke, et al., "Nano hemostat solution: immediate hemostasis at the nanoscale", *Nanomedicine*, 2(4):207-15 (2006). Epub Oct. 12, 2006.

Ellis-Behnke, et al., "Nano neuro knitting: peptide nanofiber scaffold for brain repair and axon regeneration with functional return of vision", *Proc. Natl. Acad. Sci. U.S.A.* Mar. 28, 2006;103(13):5054-9 (2006). Epub Mar. 20, 2006. *Erratum in: Proc. Natl. Acad. Sci. U.S.A.* May 9, 2006;103(19):7530.

Ellis-Behnke, et al., "Nano neuro knitting: peptide nanofiber scaffold for brain repair and axon regeneration with functional return of vision", *Nature Reviews/Neuroscience, Research Highlights*, (7):1 (2006).

Ellis-Behnke, et al., "Using nanotechnology to design potential therapies for CNS regeneration", *Curr. Pharm. Des.*, 13(24):2519-28 (2007).

"Endometriosis" *Merck Manual Professional*, pp. 1-5, www.merck.com accessed Aug. 4, 2009.

Fox News, "New peptide salve could replace adhesive bandages", www.foxnews.com, pp. 1, (Oct. 10, 2006), accessed Oct. 10, 2006.

Frechet, "Dendrimers and supramolecular chemistry", *Proc. Natl. Acad. Sci. U.S.A.*, 99(8):4782-7 (2002).

Genove, et al., "The effect of functionalized self-assembling peptide scaffolds on human aortic endothelial cell function", *Biomaterials*, 26(16):3341-51 (2005).

Gibian, "Study: Biodegradable liquids halt bleeding", *United Press International*, Oct. 10, 2006.

Gill, "Pour-on nanotechnology stops bleeding in seconds", *Chemistry World*, pp. 1-2, (2006).

Guo, et al., "Reknitting the injured spinal cord by self-assembling peptide nanofiber scaffold", *Nanomedicine*, 3(41:311-21 (2007).

Hampton, et al., Healing power found in "nano knitting", *JAMA*, 3;297(1):31 (2007).

Hartgerink, et al., "Nanomedicine: New material stops bleeding in a hurry", *Nature Nanomedicine*, 1(3): 166-167 (2006).

Hill, et al., "A field guide to foldamers", *Chem. Rev.*, 101(12):3893-4012 (2001).

Holmes, et al., "Extensive neurite outgrowth and active synapse formation on self-assembling peptide scaffolds", *Proc. Natl. Acad. Sci. USA*, 97(12):6728-6733 (2000).

"Intestinal Obstruction" *Merck Manual Professional*, pp. 1-4. www.merck.com accessed Aug. 4, 2009.

Iran Daily, "Brain-healing bridges", www.iran-daily.com, pp. 1-2, accessed Apr. 25, 2006.

"Keloids," *Merck Manual Professional*, pp. 1, www.merck.com accessed Aug. 4, 2009.

"Keloid and Hypertrophic Scar: Treatment & Medication," from, http://emedicine.medscape.com/article/l057599-treatment, pp. 1-16, accessed Aug. 4, 2009.

Kendhale, et al., "Isotactic N-alkyl acrylamide oligomers assume self-assembled sheet structure: first unequivocal evidence from crystal structure", *Chem Comm.* (Camb), 26:2756-2758 (2006).

Knudsen, "Nanosolution halts bleeding", *Technology Review*, accessed Oct. 10, 2006.

Leon, et al., "Mechanical properties of a self-assembling oligopeptide matrix", *J. Biomater. Sci. Polym. Ed.*, 9(3):297-312 (1998).

Ma, et al., "Supramolecular polymer chemistry: self-assembling dendrimers using the DDA.AAD (GC-like) hydrogen bonding motif", *J. Am. Chem. Soc.*, 124(461:13757-69 (2002).

Marks, "Optic nerve regrown", *New Scientist* on www.stemcellschina.com, (Mar. 15, 2006), updated Jun. 29, 2006, accessed Aug. 11, 2006.

Mathiowitz and Langer, "Polyanhydride microspheres as drug carriers I. Hot-melt microencapsulation", *J. Controlled Release*, 5(1):13-22 (1987).

Mathiowitz, et al., "Morphology of polyanhydride microsphere delivery systems", *Scanning Microscopy*, 4(2):329-340 (1990).

Mathiowitz, et al., "Novel microcapsules for delivery systems", *Reactive Polymers*, 6:275-83 (1987).

Mathiowitz, et al., "Polyanhydride microspheres as drug carriers. II. microencapsulation by solvent removal", *J. Appl. Polymer Sci.*, 35, 755-774 (1988).

Mathiowitz, et al., "Polyanhydride microspheres. IV: Morphology and characterization of systems made by spray drying", *J. Appl. Polymer Sci.*, 45:125-134 (1992).

MIT News, "MIT material stops bleeding in seconds", www.web.mit.edu, pp. 1-2, Oct. 10, 2006, accessed Jul. 10, 2009.

Mumbai Mirror, "New Solution to stop bleeding", www.mumbaimirror.com; pp. 1 accessed Oct. 17, 2006.

Nano China, "Stop bleeding", www.nanochina.cn, pp. 1-3, (Oct. 27, 2006), accessed Nov. 11, 2006.

Narmoneva, et al., "Self-assembling short oligopeptides and the promotion of angiogenesis", *Biomaterials*, 26(23):4837-46 (2005).

Newindpress, "New nano-gel that stops bleeding within seconds", www.newindpress.com, pp. 1, accessed Oct. 11, 2006.

News in Science, "Liquid stops bleeding during surgery", *Reuters*, pp. 1-2, accessed Oct. 10, 2006.

(56) References Cited

OTHER PUBLICATIONS

Palmer, "Peptide soup halts blood loss", *Science NOW Daily News*, pp. 1, Oct. 10, 2006.

Penland, "Recently discovered by researchers, a new liquid can stop bleeding faster than you can slap on a band-aid", *Discover Magazine*, Oct. 19, 2006.

"Residue" definition from http://dictionary.reference.com/browse/residue, pp. 1-4. accessed Jul. 13, 2009.

Sawhney, et al., "Bioerodible hydrogels based on photopolymerized poly(ethylene glycol)-co-poly(αhydroxy acid) diacrylate macromers", *Macromolecules*, 26(4):581.587 (1993).

Schneider, et al., "Behavioral testing and preliminary analysis of the hamster visual system", *Nat. Protoc.*, 1(4):1898-905 (2006).

Science, Engineering and Technology, "Nanomaterial stops bleeding in seconds", www.scenta.co.uk, pp. 1-2, accessed Oct. 10, 2006.

Scientific American, "Protein gels stops bleeding in unknown way", www.sciam.com, pp. 1-2, accessed Oct. 10, 2006.

Scrivener, "Bleeding? Here's a simple solution", Toronto Star, (Oct. 15, 2006).

Teather, et al., "Differential induction of c-Jun and Fos-like proteins in rat hippocampus and dorsal striatum after training in two water maze tasks", *Neurobiol. Learn Mem.*, 84(2):75-84 (2005).

Thomas, et al., "Nano neuro knitting repairs injured brain", *Lancet Neurol.*, 5(5):386 (2006).

Trafton, et al., "New material halts bleeding", *MIT Tech Talk*, 51(5):1-3 (2006).

Tu and Tirrell, "Bottom-up design of biomimetic assemblies", *Adv. Drug Deliv. Rev.*, 56(11):1537-63 (2004).

"Tubal Dysfunction and Pelvic Lesions," *Merck Manual Professional*, pp. 1-2, www.merck.com accessed Aug. 4, 2009.

What's Next in Science & Technology, "Biodegradable liquids can stop bleeding almost instantly—could significantly impact medicine", (Oct. 10, 2006), accessed Oct. 15, 2006.

Wilson, "Nano neuro-kit", *Drug Discovery & Development*, accessed Sep. 22, 2006.

Yung, et al., "Scientists discover new way to control bleeding", *The Standard*, pp. 1-2, (Oct. 11, 2006), accessed Oct. 10, 2006.

Zhang, et al., "Designer self-assembling peptide nanofiber scaffolds for 3D tissue cell cultures", *Semin. Cancer Biol.*, 15(5):413-20 (2005).

Zhang, et al., "Peptide self-assembly in functional polymer science and engineering", *Reactive & Functional Polymers*, 41:91-102 (1999).

Zhang, et al., "Self-complementary oligopeptide matrices support mammalian cell attachment", *Biomaterials*, 16(18):1385-1393 (1995).

Zhang, et al., "Spontaneous assembly of a self-complementary oligopeptide to form a stable macroscopic membrane", *Proc. Natl. Acad. Sci. USA*, 90(8):3334-3338 (1993).

Zimmerman, et al., "Self-assembling dendrimers", *Science*, 271(5252):1095-8 (1996).

Chen, et al., "A hybrid silk/RADA-Based fibrous scaffold with triple hierarch for ligament regeneration", Tissue Eng, 18(13-14):1399-409 (2012).

Mishra, et al., "Ultrasmall natural peptides self-assemble to strong temperature-resistant helical fibers in scaffolds suitable for tissue engineering", Nano Today, 6(3):232-9 (2011).

Osterman, et al., "Design and characterization of peptides with amphiphilic $^2$-strand structures", J Cellular Biochem., 29-57-72 (1985), vbTab.

\* cited by examiner

SEQUENCE LISTING

```
<160> NUMBER OF SEQ ID NOS: 410

<210> SEQ ID NO 1
<211> LENGTH: 4
<212> TYPE: PRT
<213> ORGANISM: Artificial Sequence
<220> FEATURE:
<223> OTHER INFORMATION: Synthetic self-assembling peptide

<400> SEQUENCE: 1

Gly Gln Gly Gln
1

<210> SEQ ID NO 2
<211> LENGTH: 6
<212> TYPE: PRT
<213> ORGANISM: Artificial Sequence
<220> FEATURE:
<223> OTHER INFORMATION: Synthetic self-assembling peptide
```

```
<400> SEQUENCE: 2

Gly Gly Gln Gln Gly Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic self-assembling peptide

<400> SEQUENCE: 3

Gly Gln Gln Gly Gln Gln Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic self-assembling peptide

<400> SEQUENCE: 4

Gly Gly Gln Gly Gly Gln Gly Gly
1               5

<210> SEQ ID NO 5
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 5

Ser Gly Ser Gly Ser Gly Ser Gly Ser Gly Ser Gly Ser Gly Ser Gly
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 6

Ser Ala Ser Ala Ser Ala Ser Ala Ser Ala Ser Ala Ser Ala Ser Ala
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 7

Ser Val Ser Val Ser Val Ser Val Ser Val Ser Val Ser Val Ser Val
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic self-assembling peptide
```

```
<400> SEQUENCE: 8

Ser Leu Ser Leu Ser Leu Ser Leu Ser Leu Ser Leu Ser Leu Ser Leu
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 9

Ser Ile Ser Ile Ser Ile Ser Ile Ser Ile Ser Ile Ser Ile Ser Ile
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 10

Ser Met Ser Met Ser Met Ser Met Ser Met Ser Met Ser Met Ser Met
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 11

Ser Phe Ser Phe Ser Phe Ser Phe Ser Phe Ser Phe Ser Phe Ser Phe
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic self-assembling peptide

<400> SEQUENCE: 12

Trp Ser Trp Ser Trp Ser Trp Ser Trp Ser Trp Ser Trp Ser Trp
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 13

Ser Pro Ser Pro Ser Pro Ser Pro Ser Pro Ser Pro Ser Pro Ser Pro
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 14
```

```
Thr Gly Thr Gly Thr Gly Thr Gly Thr Gly Thr Gly Thr Gly Thr Gly
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 15

Thr Ala Thr Ala Thr Ala Thr Ala Thr Ala Thr Ala Thr Ala Thr Ala
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 16

Thr Val Thr Val Thr Val Thr Val Thr Val Thr Val Thr Val Thr Val
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 17

Thr Leu Thr Leu Thr Leu Thr Leu Thr Leu Thr Leu Thr Leu Thr Leu
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 18

Thr Ile Thr Ile Thr Ile Thr Ile Thr Ile Thr Ile Thr Ile Thr Ile
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 19

Thr Met Thr Met Thr Met Thr Met Thr Met Thr Met Thr Met Thr Met
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 20
```

Thr Phe Thr Phe Thr Phe Thr Phe Thr Phe Thr Phe Thr Phe Thr Phe
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 21

Thr Trp Thr Trp Thr Trp Thr Trp Thr Trp Thr Trp Thr Trp Thr Trp
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 22

Thr Pro Thr Pro Thr Pro Thr Pro Thr Pro Thr Pro Thr Pro Thr Pro
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 23

Cys Gly Cys Gly Cys Gly Cys Gly Cys Gly Cys Gly Cys Gly Cys Gly
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 24

Cys Ala Cys Ala Cys Ala Cys Ala Cys Ala Cys Ala Cys Ala Cys Ala
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 25

Cys Val Cys Val Cys Val Cys Val Cys Val Cys Val Cys Val Cys Val
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 26

Cys Leu Cys Leu Cys Leu Cys Leu Cys Leu Cys Leu Cys Leu Cys Leu

```
1               5                   10                  15
```

<210> SEQ ID NO 27
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 27

```
Cys Ile Cys Ile Cys Ile Cys Ile Cys Ile Cys Ile Cys Ile Cys Ile
1               5                   10                  15
```

<210> SEQ ID NO 28
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 28

```
Cys Met Cys Met Cys Met Cys Met Cys Met Cys Met Cys Met Cys Met
1               5                   10                  15
```

<210> SEQ ID NO 29
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 29

```
Cys Phe Cys Phe Cys Phe Cys Phe Cys Phe Cys Phe Cys Phe Cys Phe
1               5                   10                  15
```

<210> SEQ ID NO 30
<211> LENGTH: 15
<212> TYPE: PRT
<213> ORGANISM: Artificial Sequence
<220> FEATURE:
<223> OTHER INFORMATION: Synthetic self-assembling peptide

<400> SEQUENCE: 30

```
Cys Trp Cys Trp Cys Trp Cys Trp Cys Trp Cys Trp Cys Trp Cys
1               5                   10                  15
```

<210> SEQ ID NO 31
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 31

```
Cys Pro Cys Pro Cys Pro Cys Pro Cys Pro Cys Pro Cys Pro Cys Pro
1               5                   10                  15
```

<210> SEQ ID NO 32
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 32

```
Tyr Gly Tyr Gly Tyr Gly Tyr Gly Tyr Gly Tyr Gly Tyr Gly Tyr Gly
1               5                   10                  15
```

<210> SEQ ID NO 33
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 33

Tyr Ala Tyr Ala Tyr Ala Tyr Ala Tyr Ala Tyr Ala Tyr Ala Tyr Ala
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 34

Tyr Val Tyr Val Tyr Val Tyr Val Tyr Val Tyr Val Tyr Val Tyr Val
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 35

Tyr Leu Tyr Leu Tyr Leu Tyr Leu Tyr Leu Tyr Leu Tyr Leu Tyr Leu
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 36

Tyr Ile Tyr Ile Tyr Ile Tyr Ile Tyr Ile Tyr Ile Tyr Ile Tyr Ile
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 37

Tyr Met Tyr Met Tyr Met Tyr Met Tyr Met Tyr Met Tyr Met Tyr Met
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 38

Tyr Phe Tyr Phe Tyr Phe Tyr Phe Tyr Phe Tyr Phe Tyr Phe Tyr Phe
1               5                   10                  15

```
<210> SEQ ID NO 39
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 39

Tyr Trp Tyr Trp Tyr Trp Tyr Trp Tyr Trp Tyr Trp Tyr Trp Tyr Trp
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 40

Tyr Pro Tyr Pro Tyr Pro Tyr Pro Tyr Pro Tyr Pro Tyr Pro Tyr Pro
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 41

Asn Gly Asn Gly Asn Gly Asn Gly Asn Gly Asn Gly Asn Gly Asn Gly
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 42

Asn Ala Asn Ala Asn Ala Asn Ala Asn Ala Asn Ala Asn Ala Asn Ala
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 43

Asn Val Asn Val Asn Val Asn Val Asn Val Asn Val Asn Val Asn Val
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 44

Asn Leu Asn Leu Asn Leu Asn Leu Asn Leu Asn Leu Asn Leu Asn Leu
1               5                   10                  15
```

```
<210> SEQ ID NO 45
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 45

Asn Ile Asn Ile Asn Ile Asn Ile Asn Ile Asn Ile Asn Ile Asn Ile
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 46

Asn Met Asn Met Asn Met Asn Met Asn Met Asn Met Asn Met Asn Met
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 47

Asn Phe Asn Phe Asn Phe Asn Phe Asn Phe Asn Phe Asn Phe Asn Phe
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 48

Asn Trp Asn Trp Asn Trp Asn Trp Asn Trp Asn Trp Asn Trp Asn Trp
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 49

Asn Pro Asn Pro Asn Pro Asn Pro Asn Pro Asn Pro Asn Pro Asn Pro
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 50

Gln Gly Gln Gly Gln Gly Gln Gly Gln Gly Gln Gly Gln Gly Gln Gly
1               5                   10                  15

<210> SEQ ID NO 51
```

```
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 51

Gln Ala Gln Ala Gln Ala Gln Ala Gln Ala Gln Ala Gln Ala Gln Ala
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 52

Gln Val Gln Val Gln Val Gln Val Gln Val Gln Val Gln Val Gln Val
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 53

Gln Leu Gln Leu Gln Leu Gln Leu Gln Leu Gln Leu Gln Leu Gln Leu
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 54

Gln Ile Gln Ile Gln Ile Gln Ile Gln Ile Gln Ile Gln Ile Gln Ile
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 55

Gln Met Gln Met Gln Met Gln Met Gln Met Gln Met Gln Met Gln Met
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 56

Gln Phe Gln Phe Gln Phe Gln Phe Gln Phe Gln Phe Gln Phe Gln Phe
1               5                   10                  15

<210> SEQ ID NO 57
<211> LENGTH: 16
```

```
<212> TYPE: PRT
<213> ORGANISM: Artificial Sequence
<220> FEATURE:
<223> OTHER INFORMATION: Synthetic self-assembling peptide

<400> SEQUENCE: 57

Gln Trp Gln Trp Gln Trp Gln Trp Gln Trp Gln Trp Gln Trp Gln Trp
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 58

Gln Pro Gln Pro Gln Pro Gln Pro Gln Pro Gln Pro Gln Pro Gln Pro
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 59

Ala Glu Ala Lys Ala Glu Ala Lys Ala Glu Ala Lys Ala Glu Ala Lys
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 60

Arg Ala Asp Ala Arg Ala Asp Ala Arg Ala Asp Ala Arg Ala Asp Ala
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 61

Arg Ala Glu Ala Arg Ala Glu Ala Arg Ala Glu Ala Arg Ala Glu Ala
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 62

Lys Ala Asp Ala Lys Ala Asp Ala Lys Ala Asp Ala Lys Ala Asp Ala
1               5                   10                  15

<210> SEQ ID NO 63
<211> LENGTH: 8
<212> TYPE: PRT
```

```
<213> ORGANISM: Artificial Sequence
<220> FEATURE:
<223> OTHER INFORMATION: Synthetic chemically modified peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MISC_FEATURE
<222> LOCATION: (1)..(1)
<223> OTHER INFORMATION: Modified with pyridoxamine phosphate
<220> FEATURE:
<221> NAME/KEY: MISC_FEATURE
<222> LOCATION: (7)..(7)
<223> OTHER INFORMATION: X is ornithine
<220> FEATURE:
<221> NAME/KEY: MOD_RES
<222> LOCATION: (8)..(8)
<223> OTHER INFORMATION: Amidation

<400> SEQUENCE: 63

Tyr Ile Thr Asn Cys Pro Xaa Tyr
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: 3-mercaptopropionyl modification

<400> SEQUENCE: 64

Tyr Phe Gln Asn Cys Pro Arg
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MOD_RES
<222> LOCATION: (9)..(9)
<223> OTHER INFORMATION: Amidation

<400> SEQUENCE: 65

Cys Tyr Phe Gln Asn Cys Pro Arg Gly
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic peptide

<400> SEQUENCE: 66

Cys Tyr Phe Gln Asn Cys Pro Arg
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic chemically modified peptide
```

```
<220> FEATURE:
<221> NAME/KEY: MOD_RES
<222> LOCATION: (9)..(9)
<223> OTHER INFORMATION: AMIDATION

<400> SEQUENCE: 67

Cys Tyr Ile Gln Asn Cys Pro Arg Gly
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (4)..(5)
<223> OTHER INFORMATION: Aminosuccinyl modification
<220> FEATURE:
<221> NAME/KEY: MOD_RES
<222> LOCATION: (7)..(7)
<223> OTHER INFORMATION: AMIDATION

<400> SEQUENCE: 68

Tyr Phe Gln Asn Pro Arg Gly
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (4)..(5)
<223> OTHER INFORMATION: Aminosuccinyl modification
<220> FEATURE:
<221> NAME/KEY: MOD_RES
<222> LOCATION: (7)..(7)
<223> OTHER INFORMATION: AMIDATION

<400> SEQUENCE: 69

Tyr Ile Gln Asn Pro Arg Gly
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: 3-mercaptopropionyl-D-Pyridylanine modification
<220> FEATURE:
<221> NAME/KEY: MOD_RES
<222> LOCATION: (7)..(7)
<223> OTHER INFORMATION: AMIDATION

<400> SEQUENCE: 70

Phe Gln Asn Cys Pro Arg Gly
1               5

<210> SEQ ID NO 71
<211> LENGTH: 9
<212> TYPE: PRT
<213> ORGANISM: Artificial Sequence
<220> FEATURE:
```

```
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: Deamino penicillamine modification
<220> FEATURE:
<221> NAME/KEY: MOD_RES
<222> LOCATION: (9)..(9)
<223> OTHER INFORMATION: AMIDATION

<400> SEQUENCE: 71

Tyr Phe Val Asn Cys Pro Asp Arg Gly
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: 3-mercaptopropionyl modification
<220> FEATURE:
<221> NAME/KEY: MOD_RES
<222> LOCATION: (8)..(8)
<223> OTHER INFORMATION: AMIDATION

<400> SEQUENCE: 72

Tyr Phe Gln Asn Cys Pro Arg Gly
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: 3-mercaptopropionyl modification
<220> FEATURE:
<221> NAME/KEY: MOD_RES
<222> LOCATION: (9)..(9)
<223> OTHER INFORMATION: AMIDATION

<400> SEQUENCE: 73

Tyr Phe Gln Asn Cys Pro Asp Arg Gly
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: 3-mercaptopropionyl modification

<400> SEQUENCE: 74

Tyr Phe Gln Asn Cys Pro Lys
1               5

<210> SEQ ID NO 75
<211> LENGTH: 9
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 75

Cys Tyr Phe Gln Asn Cys Pro Lys Gly
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic peptide

<400> SEQUENCE: 76

Cys Tyr Phe Gln Asn Cys Pro Lys
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: 3-mercaptopropionyl modification
<220> FEATURE:
<221> NAME/KEY: MOD_RES
<222> LOCATION: (1)..(1)
<223> OTHER INFORMATION: AMIDATION

<400> SEQUENCE: 77

Tyr Phe Val Asn Cys Pro Asp Arg Gly
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (7)..(7)
<223> OTHER INFORMATION: X is ornithine
<220> FEATURE:
<221> NAME/KEY: MOD_RES
<222> LOCATION: (8)..(8)
<223> OTHER INFORMATION: AMIDATION

<400> SEQUENCE: 78

Cys Phe Ile Gln Asn Cys Pro Xaa Gly
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: pyridoxamine phosphate modification
<220> FEATURE:
```

```
<221> NAME/KEY: MISC_FEATURE
<222> LOCATION: (2)..(2)
<223> OTHER INFORMATION: ethoxy modification
<220> FEATURE:
<221> NAME/KEY: MISC_FEATURE
<222> LOCATION: (8)..(8)
<223> OTHER INFORMATION: X is citrulline
<220> FEATURE:
<221> NAME/KEY: MOD_RES
<222> LOCATION: (9)..(9)
<223> OTHER INFORMATION: AMIDATION

<400> SEQUENCE: 79

Asp Tyr Phe Val Asn Cys Pro Xaa Gly
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: pyridoxamine phosphate modification
<220> FEATURE:
<221> NAME/KEY: MISC_FEATURE
<222> LOCATION: (1)..(1)
<223> OTHER INFORMATION: ethoxy modification
<220> FEATURE:
<221> NAME/KEY: MOD_RES
<222> LOCATION: (8)..(8)
<223> OTHER INFORMATION: AMIDATION

<400> SEQUENCE: 80

Tyr Phe Val Asn Cys Pro Arg Gly
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: pyridoxamine phosphate modification
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (8)..(8)
<223> OTHER INFORMATION: AMIDATION

<400> SEQUENCE: 81

Tyr Phe Gln Asn Cys Pro Arg Gly
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(1)
<223> OTHER INFORMATION: pyridoxamine phosphate modification
<220> FEATURE:
```

```
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (1)..(1)
<223> OTHER INFORMATION: AMIDATION
<220> FEATURE:
<221> NAME/KEY: MISC_FEATURE
<222> LOCATION: (7)..(7)
<223> OTHER INFORMATION: X is ornithine

<400> SEQUENCE: 82

Tyr Ile Gln Asn Cys Pro Xaa Gly
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide

<400> SEQUENCE: 83

Gly Asp Arg Gly Asp Ser Pro
1               5

<210> SEQ ID NO 84
<211> LENGTH: 11
<212> TYPE: PRT
<213> ORGANISM: Artificial Sequence
<220> FEATURE:
<223> OTHER INFORMATION: Synthetic peptide

<400> SEQUENCE: 84

Gly Asp Arg Gly Asp Ser Pro Ala Ser Ser Lys
1               5                   10

<210> SEQ ID NO 85
<211> LENGTH: 9
<212> TYPE: PRT
<213> ORGANISM: Artificial Sequence
<220> FEATURE:
<223> OTHER INFORMATION: Synthetic chemically modified peptide
<220> FEATURE:
<221> NAME/KEY: MISC_FEATURE
<222> LOCATION: (1)..(2)
<223> OTHER INFORMATION: penicillamine modification

<400> SEQUENCE: 85

Gly Gly Arg Gly Asp Ser Pro Cys Ala
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic peptide

<400> SEQUENCE: 86

Gly Arg Ala Asp Ser Pro
1               5

<210> SEQ ID NO 87
<211> LENGTH: 7
<212> TYPE: PRT
<213> ORGANISM: Artificial Sequence
<220> FEATURE:
```

<223> OTHER INFORMATION: Synthetic peptide

<400> SEQUENCE: 87

Gly Arg Gly Asp Ser Pro
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic peptide

<400> SEQUENCE: 88

Gly Arg Gly Asp Asn Pro
1               5

<210> SEQ ID NO 89
<211> LENGTH: 5
<212> TYPE: PRT
<213> ORGANISM: Artificial Sequence
<220> FEATURE:
<223> OTHER INFORMATION: Synthetic peptide

<400> SEQUENCE: 89

Gly Arg Gly Asp Ser
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic peptide

<400> SEQUENCE: 90

Gly Arg Gly Asp Ser Pro
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide

<400> SEQUENCE: 91

Gly Arg Gly Asp Ser Pro Cys
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide

<400> SEQUENCE: 92

Gly Arg Gly Asp Ser Pro Lys
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic peptide

<400> SEQUENCE: 93

Gly Arg Gly Asp Thr Pro
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic peptide

<400> SEQUENCE: 94

Gly Arg Gly Glu Ser
1               5

<210> SEQ ID NO 95
<211> LENGTH: 6
<212> TYPE: PRT
<213> ORGANISM: Artificial Sequence
<220> FEATURE:
<223> OTHER INFORMATION: Synthetic peptide

<400> SEQUENCE: 95

Gly Arg Gly Glu Ser Pro
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic peptide

<400> SEQUENCE: 96

Gly Arg Gly Glu Thr Pro
1               5

<210> SEQ ID NO 97
<211> LENGTH: 4
<212> TYPE: PRT
<213> ORGANISM: Artificial Sequence
<220> FEATURE:
<223> OTHER INFORMATION: Synthetic peptide

<400> SEQUENCE: 97

Lys Gly Asp Ser
1

<210> SEQ ID NO 98
<211> LENGTH: 6
<212> TYPE: PRT
<213> ORGANISM: Artificial Sequence
<220> FEATURE:
<223> OTHER INFORMATION: Synthetic peptide

<400> SEQUENCE: 98

Gly Ala Val Ser Thr Ala
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic peptide

```
<400> SEQUENCE: 99

Trp Thr Val Pro Thr Ala
1               5

<210> SEQ ID NO 100
<211> LENGTH: 11
<212> TYPE: PRT
<213> ORGANISM: Artificial Sequence
<220> FEATURE:
<223> OTHER INFORMATION: Synthetic peptide

<400> SEQUENCE: 100

Thr Asp Val Asn Gly Asp Gly Arg His Asp Leu
1               5                   10

<210> SEQ ID NO 101
<211> LENGTH: 4
<212> TYPE: PRT
<213> ORGANISM: Artificial Sequence
<220> FEATURE:
<223> OTHER INFORMATION: Synthetic peptide

<400> SEQUENCE: 101

Arg Glu Asp Val
1

<210> SEQ ID NO 102
<211> LENGTH: 4
<212> TYPE: PRT
<213> ORGANISM: Artificial Sequence
<220> FEATURE:
<223> OTHER INFORMATION: Synthetic peptide

<400> SEQUENCE: 102

Arg Gly Asp Cys
1

<210> SEQ ID NO 103
<211> LENGTH: 4
<212> TYPE: PRT
<213> ORGANISM: Artificial Sequence
<220> FEATURE:
<223> OTHER INFORMATION: Synthetic peptide

<400> SEQUENCE: 103

Arg Gly Asp Ser
1

<210> SEQ ID NO 104
<211> LENGTH: 10
<212> TYPE: PRT
<213> ORGANISM: Artificial Sequence
<220> FEATURE:
<223> OTHER INFORMATION: Synthetic peptide

<400> SEQUENCE: 104

Arg Gly Asp Ser Pro Ala Ser Ser Lys Pro
1               5                   10

<210> SEQ ID NO 105
<211> LENGTH: 4
<212> TYPE: PRT
<213> ORGANISM: Artificial Sequence
<220> FEATURE:
<223> OTHER INFORMATION: Synthetic peptide

<400> SEQUENCE: 105
```

```
Arg Gly Asp Thr
1

<210> SEQ ID NO 106
<211> LENGTH: 4
<212> TYPE: PRT
<213> ORGANISM: Artificial Sequence
<220> FEATURE:
<223> OTHER INFORMATION: Synthetic peptide

<400> SEQUENCE: 106

Arg Gly Asp Val
1

<210> SEQ ID NO 107
<211> LENGTH: 4
<212> TYPE: PRT
<213> ORGANISM: Artificial Sequence
<220> FEATURE:
<223> OTHER INFORMATION: Synthetic peptide

<400> SEQUENCE: 107

Arg Gly Glu Ser
1

<210> SEQ ID NO 108
<211> LENGTH: 4
<212> TYPE: PRT
<213> ORGANISM: Artificial Sequence
<220> FEATURE:
<223> OTHER INFORMATION: Synthetic peptide

<400> SEQUENCE: 108

Ser Asp Gly Arg
1

<210> SEQ ID NO 109
<211> LENGTH: 5
<212> TYPE: PRT
<213> ORGANISM: Artificial Sequence
<220> FEATURE:
<223> OTHER INFORMATION: Synthetic peptide

<400> SEQUENCE: 109

Ser Asp Gly Arg Gly
1               5

<210> SEQ ID NO 110
<211> LENGTH: 5
<212> TYPE: PRT
<213> ORGANISM: Artificial Sequence
<220> FEATURE:
<223> OTHER INFORMATION: Synthetic peptide

<400> SEQUENCE: 110

Tyr Arg Gly Asp Ser
1               5

<210> SEQ ID NO 111
<211> LENGTH: 14
<212> TYPE: PRT
<213> ORGANISM: Artificial Sequence
<220> FEATURE:
<223> OTHER INFORMATION: Synthetic peptide

<400> SEQUENCE: 111
```

```
Glu Gly Val Asn Asp Asn Glu Glu Gly Phe Phe Ser Ala Arg
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Synthetic peptide

<400> SEQUENCE: 112

Tyr Ala Asp Ser Gly Glu Gly Asp Phe Leu Ala Glu Gly Gly Gly Val
1               5                   10                  15

Arg

<210> SEQ ID NO 113
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Glp modification

<400> SEQUENCE: 113

Gly Val Asn Asp Asn Glu Glu Gly Phe Phe Ser Ala Arg Tyr
1               5                   10

<210> SEQ ID NO 114
<211> LENGTH: 16
<212> TYPE: PRT
<213> ORGANISM: Artificial Sequence
<220> FEATURE:
<223> OTHER INFORMATION: Synthetic peptide

<400> SEQUENCE: 114

Glu Ala Lys Ala Glu Ala Lys Ala Glu Ala Lys Ala Glu Ala Lys Ala
1               5                   10                  15

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118
<211> LENGTH: 12
<212> TYPE: PRT
<213> ORGANISM: Artificial Sequence
<220> FEATURE:
<223> OTHER INFORMATION: Synthetic peptide

<400> SEQUENCE: 118
```

Arg Ala Arg Ala Arg Ala Asp Ala Asp Ala Asp Ala
1               5                   10

<210> SEQ ID NO 119
<211> LENGTH: 8
<212> TYPE: PRT
<213> ORGANISM: Artificial Sequence
<220> FEATURE:
<223> OTHER INFORMATION: Synthetic self-assembling peptide

<400> SEQUENCE: 119

Arg Arg Arg Arg Asp Asp Asp Asp
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic self-assembling peptide

<400> SEQUENCE: 120

Gly Gly Gly Gly Ser Ser Ser Ser
1               5

<210> SEQ ID NO 121
<211> LENGTH: 4
<212> TYPE: PRT
<213> ORGANISM: Artificial Sequence
<220> FEATURE:
<223> OTHER INFORMATION: Synthetic self-assembling peptide

<400> SEQUENCE: 121

Lys Lys Lys Lys
1

<210> SEQ ID NO 122
<211> LENGTH: 4
<212> TYPE: PRT
<213> ORGANISM: Artificial Sequence
<220> FEATURE:
<223> OTHER INFORMATION: Synthetic self-assembling peptide

<400> SEQUENCE: 122

Arg Arg Arg Arg
1

<210> SEQ ID NO 123
<211> LENGTH: 4
<212> TYPE: PRT
<213> ORGANISM: Artificial Sequence
<220> FEATURE:
<223> OTHER INFORMATION: Synthetic self-assembling peptide

<400> SEQUENCE: 123

His His His His
1

<210> SEQ ID NO 124
<211> LENGTH: 4
<212> TYPE: PRT
<213> ORGANISM: Artificial Sequence
<220> FEATURE:
<223> OTHER INFORMATION: Synthetic self-assembling peptide

<400> SEQUENCE: 124

Asp Asp Asp Asp

```
<210> SEQ ID NO 125
<211> LENGTH: 4
<212> TYPE: PRT
<213> ORGANISM: Artificial Sequence
<220> FEATURE:
<223> OTHER INFORMATION: Synthetic self-assembling peptide

<400> SEQUENCE: 125

Glu Glu Glu Glu
1

<210> SEQ ID NO 126
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 126

Gly Gly Gly Gly Gly Asp Gly Asp Gly Asp Gly Asp Gly Asp Gly Asp
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 127

Gly Gly Gly Gly Gly Glu Gly Glu Gly Glu Gly Glu Gly Glu Gly Glu
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 128

Gly Gly Gly Gly Gly Lys Gly Lys Gly Lys Gly Lys Gly Lys Gly Lys
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 129

Gly Gly Gly Gly Gly Arg Gly Arg Gly Arg Gly Arg Gly Arg Gly Arg
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 130

Gly Gly Gly Gly Gly His Gly His Gly His Gly His Gly His Gly His
1               5                   10                  15
```

```
<210> SEQ ID NO 131
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 131

Ala Ala Ala Ala Ala Asp Ala Asp Ala Asp Ala Asp Ala Asp Ala Asp
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 132

Ala Ala Ala Ala Ala Glu Ala Glu Ala Glu Ala Glu Ala Glu Ala Glu
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 133

Lys Ala Ala Ala Ala Ala Lys Ala Lys Ala Lys Ala Lys Ala Lys Ala
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 134

Ala Ala Ala Ala Ala Arg Ala Arg Ala Arg Ala Arg Ala Arg Ala Arg
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 135

Ala Ala Ala Ala Ala His Ala His Ala His Ala His Ala His Ala His
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 136

Val Val Val Val Val Asp Val Asp Val Asp Val Asp Val Asp Val Asp
1               5                   10                  15
```

<210> SEQ ID NO 137
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 137

Val Val Val Val Val Glu Val Glu Val Glu Val Glu Val Glu Val Glu
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 138

Val Val Val Val Val Lys Val Lys Val Lys Val Lys Val Lys Val Lys
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 139

Val Val Val Val Val Arg Val Arg Val Arg Val Arg Val Arg Val Arg
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 140

Val Val Val Val Val His Val His Val His Val His Val His Val His
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 141

Leu Leu Leu Leu Leu Asp Leu Asp Leu Asp Leu Asp Leu Asp Leu Asp
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 142

Leu Leu Leu Leu Leu Glu Leu Glu Leu Glu Leu Glu Leu Glu Leu Glu
1               5                   10                  15

```
<210> SEQ ID NO 143
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 143

Leu Leu Leu Leu Leu Lys Leu Lys Leu Lys Leu Lys Leu Lys Leu Lys
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 144

Leu Leu Leu Leu Leu Arg Leu Arg Leu Arg Leu Arg Leu Arg Leu Arg
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 145

Leu Leu Leu Leu Leu His Leu His Leu His Leu His Leu His Leu His
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 146

Ile Ile Ile Ile Ile Asp Ile Asp Ile Asp Ile Asp Ile Asp Ile Asp
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 147

Ile Ile Ile Ile Ile Glu Ile Glu Ile Glu Ile Glu Ile Glu Ile Glu
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 148

Ile Ile Ile Ile Ile Lys Ile Lys Ile Lys Ile Lys Ile Lys Ile Lys
1               5                   10                  15

<210> SEQ ID NO 149
```

```
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 149

Ile Ile Ile Ile Ile Arg Ile Arg Ile Arg Ile Arg Ile Arg Ile Arg
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 150

Ile Ile Ile Ile Ile His Ile His Ile His Ile His Ile His Ile His
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 151

Met Met Met Met Met Asp Met Asp Met Asp Met Asp Met Asp Met Asp
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 152

Met Met Met Met Met Glu Met Glu Met Glu Met Glu Met Glu Met Glu
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 153

Met Met Met Met Met Lys Met Lys Met Lys Met Lys Met Lys Met Lys
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 154

Met Met Met Met Met Arg Met Arg Met Arg Met Arg Met Arg Met Arg
1               5                   10                  15

<210> SEQ ID NO 155
<211> LENGTH: 16
```

```
<212> TYPE: PRT
<213> ORGANISM: Artificial Sequence
<220> FEATURE:
<223> OTHER INFORMATION: Synthetic hydrophobic tail

<400> SEQUENCE: 155

Met Met Met Met Met His Met His Met His Met His Met His Met His
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 156

Phe Phe Phe Phe Phe Asp Phe Asp Phe Asp Phe Asp Phe Asp Phe Asp
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 157

Phe Phe Phe Phe Phe Glu Phe Glu Phe Glu Phe Glu Phe Glu Phe Glu
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 158

Phe Phe Phe Phe Phe Lys Phe Lys Phe Lys Phe Lys Phe Lys Phe Lys
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 159

Phe Phe Phe Phe Phe Arg Phe Arg Phe Arg Phe Arg Phe Arg Phe Arg
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 160

Phe Phe Phe Phe Phe His Phe His Phe His Phe His Phe His Phe His
1               5                   10                  15

<210> SEQ ID NO 161
<211> LENGTH: 16
<212> TYPE: PRT
```

```
<213> ORGANISM: Artificial Sequence
<220> FEATURE:
<223> OTHER INFORMATION: Synthetic hydrophobic tail

<400> SEQUENCE: 161

Trp Trp Trp Trp Trp Asp Trp Asp Trp Asp Trp Asp Trp Asp Trp Asp
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 162

Trp Trp Trp Trp Trp Glu Trp Glu Trp Glu Trp Glu Trp Glu Trp Glu
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 163

Trp Trp Trp Trp Trp Lys Trp Lys Trp Lys Trp Lys Trp Lys Trp Lys
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 164

Trp Trp Trp Trp Trp Arg Trp Arg Trp Arg Trp Arg Trp Arg Trp Arg
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 165

Trp Trp Trp Trp Trp His Trp His Trp His Trp His Trp His Trp His
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 166

Pro Pro Pro Pro Pro Asp Pro Asp Pro Asp Pro Asp Pro Asp Pro Asp
1               5                   10                  15

<210> SEQ ID NO 167
<211> LENGTH: 16
<212> TYPE: PRT
<213> ORGANISM: Artificial Sequence
```

```
<220> FEATURE:
<223> OTHER INFORMATION: Synthetic hydrophobic tail

<400> SEQUENCE: 167

Pro Pro Pro Pro Pro Glu Pro Glu Pro Glu Pro Glu Pro Glu
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 168

Pro Pro Pro Pro Pro Lys Pro Lys Pro Lys Pro Lys Pro Lys
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 169

Pro Pro Pro Pro Pro Arg Pro Arg Pro Arg Pro Arg Pro Arg
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 170

Pro Pro Pro Pro Pro His Pro His Pro His Pro His Pro His
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 171

Ala Ala Ala Ala Ala Arg Ala Asp Ala Arg Ala Asp Ala Arg Ala Asp
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 172

Ala Ala Ala Ala Ala Arg Ala Arg Ala Asp Ala Asp Ala Arg Ala Arg
1               5                   10                  15

<210> SEQ ID NO 173
<211> LENGTH: 16
<212> TYPE: PRT
<213> ORGANISM: Artificial Sequence
<220> FEATURE:
```

-continued

<223> OTHER INFORMATION: Synthetic hydrophobic tail

<400> SEQUENCE: 173

Ala Ala Ala Ala Ala Glu Ala Lys Ala Glu Ala Lys Ala Glu Ala Lys
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 174

Ala Ala Ala Ala Ala Glu Ala Glu Ala Lys Ala Lys Ala Glu Ala Glu
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 175

Ala Ala Ala Ala Ala Arg Ala Glu Ala Arg Ala Glu Ala Arg Ala Glu
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 176

Ala Ala Ala Ala Ala Arg Ala Arg Ala Glu Ala Glu Ala Arg Ala Glu
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 177

Ala Ala Ala Ala Ala Lys Ala Asp Ala Lys Ala Asp Ala Lys Ala Asp
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 178

Ala Ala Ala Ala Ala Glu Ala His Ala Glu Ala His Ala Glu Ala His
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Synthetic hydrophobic tail

```
<400> SEQUENCE: 179

Ala Ala Ala Ala Ala Glu Ala Glu Ala His Ala His Ala Glu Ala Glu
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 180

Ala Ala Ala Ala Ala Arg Ala Arg Ala Arg Ala Arg Ala Arg Ala Arg
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 181

Ala Ala Ala Ala Ala Arg Ala Arg Ala Arg Ala Arg Ala Asp Ala Asp
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 182

Ala Ala Ala Ala Ala Arg Ala Arg Ala Arg Ala Asp Ala Asp Ala Asp
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 183

Ala Ala Ala Ala Ala His Ala Asp Ala His Ala Asp Ala His Ala Asp
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 184

Ala Ala Ala Ala Ala His Ala His Ala His Ala His Ala His Ala His
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Synthetic hydrophobic tail
```

```
<400> SEQUENCE: 185

Ala Ala Ala Ala Ala His Ala Asp Ala Asp Ala His Ala Asp Ala Asp
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 186

Ala Ala Ala Ala Ala His Ala Glu Ala Glu Ala His Ala Glu Ala Glu
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 187

Gly Gly Gly Gly Gly Arg Gly Asp Gly Arg Gly Asp Gly Arg Gly Asp
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 188

Gly Gly Gly Gly Gly Arg Gly Arg Gly Asp Gly Asp Gly Arg Gly Arg
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 189

Gly Gly Gly Gly Gly Glu Gly Lys Gly Glu Gly Lys Gly Glu Gly Lys
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 190

Gly Gly Gly Gly Gly Glu Gly Glu Gly Lys Gly Lys Gly Glu Gly Glu
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 191
```

Gly Gly Gly Gly Gly Arg Gly Glu Gly Glu Gly Arg Gly Glu
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 192

Gly Gly Gly Gly Gly Arg Gly Arg Gly Glu Gly Glu Gly Arg Gly Glu
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 193

Gly Gly Gly Gly Gly Lys Gly Asp Gly Lys Gly Asp Gly Lys Gly Asp
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 194

Gly Gly Gly Gly Gly Glu Gly His Gly Glu Gly His Gly Glu Gly His
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 195

Gly Gly Gly Gly Gly Glu Gly Glu Gly His Gly His Gly Glu Gly Glu
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 196

Gly Gly Gly Gly Gly Arg Gly Arg Gly Arg Gly Arg Gly Arg Gly Arg
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 197

```
Gly Gly Gly Gly Gly Arg Gly Arg Gly Arg Gly Asp Gly Asp Gly Asp
1               5                   10                  15
```

<210> SEQ ID NO 198
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 198

```
Gly Gly Gly Gly Gly Arg Gly Arg Gly Arg Gly Asp Gly Asp Gly Asp
1               5                   10                  15
```

<210> SEQ ID NO 199
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 199

```
Gly Gly Gly Gly Gly His Gly Asp Gly His Gly Asp Gly His Gly Asp
1               5                   10                  15
```

<210> SEQ ID NO 200
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 200

```
Gly Gly Gly Gly Gly His Gly His Gly His Gly His Gly His Gly His
1               5                   10                  15
```

<210> SEQ ID NO 201
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 201

```
Gly Gly Gly Gly Gly His Gly Asp Gly Asp Gly His Gly Asp Gly Asp
1               5                   10                  15
```

<210> SEQ ID NO 202
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 202

```
Gly Gly Gly Gly Gly His Gly Glu Gly Glu Gly His Gly Glu Gly Glu
1               5                   10                  15
```

<210> SEQ ID NO 203
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 203

```
Val Val Val Val Val Arg Val Asp Val Arg Val Asp Val Arg Val Asp
```

```
<210> SEQ ID NO 204
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 204

Val Val Val Val Val Arg Val Arg Val Asp Val Asp Val Arg Val Arg
1               5                   10                  15

<210> SEQ ID NO 205
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 205

Val Val Val Val Val Glu Val Lys Val Glu Val Lys Val Glu Val Lys
1               5                   10                  15

<210> SEQ ID NO 206
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 206

Val Val Val Val Val Glu Val Glu Val Lys Val Lys Val Glu Val Glu
1               5                   10                  15

<210> SEQ ID NO 207
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 207

Val Val Val Val Val Arg Val Glu Val Arg Val Glu Val Arg Val Glu
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 208

Val Val Val Val Val Arg Val Arg Val Glu Val Glu Val Arg Val Glu
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 209

Val Val Val Val Val Lys Val Asp Val Lys Val Asp Val Lys Val Asp
1               5                   10                  15
```

<210> SEQ ID NO 210
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 210

Val Val Val Val Val Glu Val His Val Glu Val His Val Glu Val His
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 211

Val Val Val Val Val Glu Val Glu Val His Val His Val Glu Val Glu
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 212

Val Val Val Val Val Arg Val Arg Val Arg Val Arg Val Arg Val Arg
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 213

Val Val Val Val Val Arg Val Arg Val Arg Val Arg Val Asp Val Asp
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 214

Val Val Val Val Val Arg Val Arg Val Arg Val Asp Val Asp Val Asp
1               5                   10                  15

<210> SEQ ID NO 215
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 215

Val Val Val Val Val His Val Asp Val His Val Asp Val His Val Asp
1               5                   10                  15

<210> SEQ ID NO 216
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 216

Val Val Val Val Val His Val His Val His Val His Val His Val His
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 217

Val Val Val Val Val His Val Asp Val Asp Val His Val Asp Val Asp
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 218

Val Val Val Val Val His Val Glu Val Glu Val His Val Glu Val Glu
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 219

Leu Leu Leu Leu Leu Arg Leu Asp Leu Arg Leu Asp Leu Arg Leu Asp
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 220

Leu Leu Leu Leu Leu Arg Leu Arg Leu Asp Leu Asp Leu Arg Leu Arg
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 221

Leu Leu Leu Leu Leu Glu Leu Lys Leu Glu Leu Lys Leu Glu Leu Lys
1               5                   10                  15

```
<210> SEQ ID NO 222
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 222

Leu Leu Leu Leu Leu Glu Leu Glu Leu Lys Leu Lys Leu Glu Leu Glu
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 223

Leu Leu Leu Leu Leu Arg Leu Glu Leu Arg Leu Glu Leu Arg Leu Glu
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 224

Leu Leu Leu Leu Leu Arg Leu Arg Leu Glu Leu Glu Leu Arg Leu Glu
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 225

Leu Leu Leu Leu Leu Lys Leu Asp Leu Lys Leu Asp Leu Lys Leu Asp
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 226

Leu Leu Leu Leu Leu Glu Leu His Leu Glu Leu His Leu Glu Leu His
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 227

Leu Leu Leu Leu Leu Glu Leu Glu Leu His Leu His Leu Glu Leu Glu
1               5                   10                  15

<210> SEQ ID NO 228
```

```
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 228

Leu Leu Leu Leu Leu Arg Leu Arg Leu Arg Leu Arg Leu Arg Leu Arg
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 229

Leu Leu Leu Leu Leu Arg Leu Arg Leu Arg Leu Arg Leu Asp Leu Asp
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 230

Leu Leu Leu Leu Leu Arg Leu Arg Leu Arg Leu Asp Leu Asp Leu Asp
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 231

Leu Leu Leu Leu Leu His Leu Asp Leu His Leu Asp Leu His Leu Asp
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 232

Leu Leu Leu Leu Leu His Leu His Leu His Leu His Leu His Leu His
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 233

Leu Leu Leu Leu Leu His Leu Asp Leu Asp Leu His Leu Asp Leu Asp
1               5                   10                  15

<210> SEQ ID NO 234
<211> LENGTH: 16
```

```
<212> TYPE: PRT
<213> ORGANISM: Artificial Sequence
<220> FEATURE:
<223> OTHER INFORMATION: Synthetic hydrophobic tail

<400> SEQUENCE: 234

Leu Leu Leu Leu Leu His Leu Glu Leu Glu Leu His Leu Glu Leu Glu
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 235

Ile Ile Ile Ile Ile Arg Ile Asp Ile Arg Ile Asp Ile Arg Ile Asp
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 236

Ile Ile Ile Ile Ile Arg Ile Arg Ile Asp Ile Asp Ile Arg Ile Arg
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 237

Ile Ile Ile Ile Ile Glu Ile Lys Ile Glu Ile Lys Ile Glu Ile Lys
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 238

Ile Ile Ile Ile Ile Glu Ile Glu Ile Lys Ile Lys Ile Glu Ile Glu
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 239

Ile Ile Ile Ile Ile Arg Ile Glu Ile Arg Ile Glu Ile Arg Ile Glu
1               5                   10                  15

<210> SEQ ID NO 240
<211> LENGTH: 16
<212> TYPE: PRT
```

```
<213> ORGANISM: Artificial Sequence
<220> FEATURE:
<223> OTHER INFORMATION: Synthetic hydrophobic tail

<400> SEQUENCE: 240

Ile Ile Ile Ile Ile Arg Ile Arg Ile Glu Ile Glu Ile Arg Ile Glu
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 241

Ile Ile Ile Ile Ile Lys Ile Asp Ile Lys Ile Asp Ile Lys Ile Asp
1               5                   10                  15

<210> SEQ ID NO 242
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 242

Ile Ile Ile Ile Ile Glu Ile His Ile Glu Ile His Ile Glu Ile His
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 243

Ile Ile Ile Ile Ile Glu Ile Glu Ile His Ile His Ile Glu Ile Glu
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 244

Ile Ile Ile Ile Ile Arg Ile Arg Ile Arg Ile Arg Ile Arg Ile Arg
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 245

Ile Ile Ile Ile Ile Arg Ile Arg Ile Arg Ile Arg Ile Asp Ile Asp
1               5                   10                  15

<210> SEQ ID NO 246
<211> LENGTH: 16
<212> TYPE: PRT
<213> ORGANISM: Artificial Sequence
```

<220> FEATURE:
<223> OTHER INFORMATION: Synthetic hydrophobic tail

<400> SEQUENCE: 246

Ile Ile Ile Ile Ile Arg Ile Arg Ile Arg Ile Asp Ile Asp Ile Asp
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 247

Ile Ile Ile Ile Ile His Ile Asp Ile His Ile Asp Ile His Ile Asp
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 248

Ile Ile Ile Ile Ile His Ile His Ile His Ile His Ile His Ile His
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 249

Ile Ile Ile Ile Ile His Ile Asp Ile Asp Ile His Ile Asp Ile Asp
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 250

Ile Ile Ile Ile Ile His Ile Glu Ile Glu Ile His Ile Glu Ile Glu
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 251

Met Met Met Met Met Arg Met Asp Met Arg Met Asp Met Arg Met Asp
1               5                   10                  15

<210> SEQ ID NO 252
<211> LENGTH: 16
<212> TYPE: PRT
<213> ORGANISM: Artificial Sequence
<220> FEATURE:

<223> OTHER INFORMATION: Synthetic hydrophobic tail

<400> SEQUENCE: 252

Met Met Met Met Met Arg Met Arg Met Asp Met Asp Met Arg Met Arg
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 253

Met Met Met Met Met Glu Met Lys Met Glu Met Lys Met Glu Met Lys
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 254

Met Met Met Met Met Glu Met Glu Met Lys Met Lys Met Glu Met Glu
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 255

Met Met Met Met Met Arg Met Glu Met Arg Met Glu Met Arg Met Glu
1               5                   10                  15

<210> SEQ ID NO 256
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 256

Met Met Met Met Met Arg Met Arg Met Glu Met Glu Met Arg Met Glu
1               5                   10                  15

<210> SEQ ID NO 257
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 257

Met Met Met Met Met Lys Met Asp Met Lys Met Asp Met Lys Met Asp
1               5                   10                  15

<210> SEQ ID NO 258
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 258

Met Met Met Met Met Glu Met His Met Glu Met His Met Glu Met His
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 259

Met Met Met Met Met Glu Met Glu Met His Met His Met Glu Met Glu
1               5                   10                  15

<210> SEQ ID NO 260
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 260

Met Met Met Met Met Arg Met Arg Met Arg Met Arg Met Arg Met Arg
1               5                   10                  15

<210> SEQ ID NO 261
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 261

Met Met Met Met Met Arg Met Arg Met Arg Met Arg Met Asp Met Asp
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 262

Met Met Met Met Met Arg Met Arg Met Arg Met Asp Met Asp Met Asp
1               5                   10                  15

<210> SEQ ID NO 263
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 263

Met Met Met Met Met His Met Asp Met His Met Asp Met His Met Asp
1               5                   10                  15

<210> SEQ ID NO 264
<211> LENGTH: 16
<212> TYPE: PRT
<213> ORGANISM: Artificial Sequence
<220> FEATURE:
<223> OTHER INFORMATION: Synthetic hydrophobic tail

```
<400> SEQUENCE: 264

Met Met Met Met Met His Met His Met His Met His Met His Met His
1               5                   10                  15

<210> SEQ ID NO 265
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 265

Met Met Met Met Met His Met Asp Met Asp Met His Met Asp Met Asp
1               5                   10                  15

<210> SEQ ID NO 266
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 266

Met Met Met Met Met His Met Glu Met Glu Met His Met Glu Met Glu
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 267

Phe Phe Phe Phe Phe Arg Phe Asp Phe Arg Phe Asp Phe Arg Phe Asp
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 268

Phe Phe Phe Phe Phe Arg Phe Arg Phe Asp Phe Asp Phe Arg Phe Arg
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 269

Phe Phe Phe Phe Phe Glu Phe Lys Phe Glu Phe Lys Phe Glu Phe Lys
1               5                   10                  15

<210> SEQ ID NO 270
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 270
```

Phe Phe Phe Phe Phe Glu Phe Glu Phe Lys Phe Lys Phe Glu Phe Glu
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 271

Phe Phe Phe Phe Phe Arg Phe Glu Phe Arg Phe Glu Phe Arg Phe Glu
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 272

Phe Phe Phe Phe Phe Arg Phe Arg Phe Glu Phe Glu Phe Arg Phe Glu
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 273

Phe Phe Phe Phe Phe Lys Phe Asp Phe Lys Phe Asp Phe Lys Phe Asp
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 274

Phe Phe Phe Phe Phe Glu Phe His Phe Glu Phe His Phe Glu Phe His
1               5                   10                  15

<210> SEQ ID NO 275
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 275

Phe Phe Phe Phe Phe Glu Phe Glu Phe His Phe His Phe Glu Phe Glu
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 276

```
Phe Phe Phe Phe Phe Arg Phe Arg Phe Arg Phe Arg Phe Arg Phe Arg
1               5                   10                  15

<210> SEQ ID NO 277
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 277

Phe Phe Phe Phe Phe Arg Phe Arg Phe Arg Phe Arg Phe Asp Phe Asp
1               5                   10                  15

<210> SEQ ID NO 278
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 278

Phe Phe Phe Phe Phe Arg Phe Arg Phe Arg Phe Asp Phe Asp Phe Asp
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 279

Phe Phe Phe Phe Phe His Phe Asp Phe His Phe Asp Phe His Phe Asp
1               5                   10                  15

<210> SEQ ID NO 280
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 280

Phe Phe Phe Phe Phe His Phe His Phe His Phe His Phe His Phe His
1               5                   10                  15

<210> SEQ ID NO 281
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 281

Phe Phe Phe Phe Phe His Phe Asp Phe Asp Phe His Phe Asp Phe Asp
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 282

Phe Phe Phe Phe Phe His Phe Glu Phe Glu Phe His Phe Glu Phe Glu
```

```
1               5                   10                  15
```

<210> SEQ ID NO 283
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 283

```
Trp Trp Trp Trp Trp Arg Trp Asp Trp Arg Trp Asp Trp Arg Trp Asp
1               5                   10                  15
```

<210> SEQ ID NO 284
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 284

```
Trp Trp Trp Trp Trp Arg Trp Arg Trp Asp Trp Asp Trp Arg Trp Arg
1               5                   10                  15
```

<210> SEQ ID NO 285
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 285

```
Trp Trp Trp Trp Trp Glu Trp Lys Trp Glu Trp Lys Trp Glu Trp Lys
1               5                   10                  15
```

<210> SEQ ID NO 286
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 286

```
Trp Trp Trp Trp Trp Glu Trp Glu Trp Lys Trp Lys Trp Glu Trp Glu
1               5                   10                  15
```

<210> SEQ ID NO 287
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 287

```
Trp Trp Trp Trp Trp Arg Trp Glu Trp Arg Trp Glu Trp Arg Trp Glu
1               5                   10                  15
```

<210> SEQ ID NO 288
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 288

```
Trp Trp Trp Trp Trp Arg Trp Arg Trp Glu Trp Glu Trp Arg Trp Glu
1               5                   10                  15
```

<210> SEQ ID NO 289
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 289

Trp Trp Trp Trp Trp Lys Trp Asp Trp Lys Trp Asp Trp Lys Trp Asp
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 290

Trp Trp Trp Trp Trp Glu Trp His Trp Glu Trp His Trp Glu Trp His
1               5                   10                  15

<210> SEQ ID NO 291
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 291

Trp Trp Trp Trp Trp Glu Trp Glu Trp His Trp His Trp Glu Trp Glu
1               5                   10                  15

<210> SEQ ID NO 292
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 292

Trp Trp Trp Trp Trp Arg Trp Arg Trp Arg Trp Arg Trp Arg Trp Arg
1               5                   10                  15

<210> SEQ ID NO 293
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 293

Trp Trp Trp Trp Trp Arg Trp Arg Trp Arg Trp Arg Trp Asp Trp Asp
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 294

Trp Trp Trp Trp Trp Arg Trp Arg Trp Arg Trp Asp Trp Asp Trp Asp
1               5                   10                  15

```
<210> SEQ ID NO 295
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 295

Trp Trp Trp Trp Trp His Trp Asp Trp His Trp Asp Trp His Trp Asp
1               5                   10                  15

<210> SEQ ID NO 296
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 296

Trp Trp Trp Trp Trp His Trp His Trp His Trp His Trp His Trp His
1               5                   10                  15

<210> SEQ ID NO 297
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 297

Trp Trp Trp Trp Trp His Trp Asp Trp Asp Trp His Trp Asp Trp Asp
1               5                   10                  15

<210> SEQ ID NO 298
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 298

Trp Trp Trp Trp Trp His Trp Glu Trp Glu Trp His Trp Glu Trp Glu
1               5                   10                  15

<210> SEQ ID NO 299
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 299

Pro Pro Pro Pro Pro Arg Pro Asp Pro Arg Pro Asp Pro Arg Pro Asp
1               5                   10                  15

<210> SEQ ID NO 300
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 300

Pro Pro Pro Pro Pro Arg Pro Arg Pro Asp Pro Asp Pro Arg Pro Arg
1               5                   10                  15
```

```
<210> SEQ ID NO 301
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 301

Pro Pro Pro Pro Pro Glu Pro Lys Pro Glu Pro Lys Pro Glu Pro Lys
1               5                   10                  15

<210> SEQ ID NO 302
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 302

Pro Pro Pro Pro Pro Glu Pro Glu Pro Lys Pro Lys Pro Glu Pro Glu
1               5                   10                  15

<210> SEQ ID NO 303
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 303

Pro Pro Pro Pro Pro Arg Pro Glu Pro Arg Pro Glu Pro Arg Pro Glu
1               5                   10                  15

<210> SEQ ID NO 304
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 304

Pro Pro Pro Pro Pro Arg Pro Arg Pro Glu Pro Glu Pro Arg Pro Glu
1               5                   10                  15

<210> SEQ ID NO 305
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 305

Pro Pro Pro Pro Pro Lys Pro Asp Pro Lys Pro Asp Pro Lys Pro Asp
1               5                   10                  15

<210> SEQ ID NO 306
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 306

Pro Pro Pro Pro Pro Glu Pro His Pro Glu Pro His Pro Glu Pro His
1               5                   10                  15

<210> SEQ ID NO 307
```

```
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 307

Pro Pro Pro Pro Pro Glu Pro Glu Pro His Pro His Pro Glu Pro Glu
1               5                   10                  15

<210> SEQ ID NO 308
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 308

Pro Pro Pro Pro Pro Arg Pro Arg Pro Arg Pro Arg Pro Arg Pro Arg
1               5                   10                  15

<210> SEQ ID NO 309
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 309

Pro Pro Pro Pro Pro Arg Pro Arg Pro Arg Pro Arg Pro Asp Pro Asp
1               5                   10                  15

<210> SEQ ID NO 310
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 310

Pro Pro Pro Pro Pro Arg Pro Arg Pro Arg Pro Asp Pro Asp Pro Asp
1               5                   10                  15

<210> SEQ ID NO 311
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 311

Pro Pro Pro Pro Pro His Pro Asp Pro His Pro Asp Pro His Pro Asp
1               5                   10                  15

<210> SEQ ID NO 312
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 312

Pro Pro Pro Pro Pro His Pro His Pro His Pro His Pro His Pro His
1               5                   10                  15

<210> SEQ ID NO 313
<211> LENGTH: 16
```

```
<212> TYPE: PRT
<213> ORGANISM: Artificial Sequence
<220> FEATURE:
<223> OTHER INFORMATION: Synthetic hydrophobic tail

<400> SEQUENCE: 313

Pro Pro Pro Pro Pro His Pro Asp Pro Asp Pro His Pro Asp Pro Asp
1               5                   10                  15

<210> SEQ ID NO 314
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 314

Pro Pro Pro Pro Pro His Pro Glu Pro Glu Pro His Pro Glu Pro Glu
1               5                   10                  15

<210> SEQ ID NO 315
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 315

Ser Ser Ser Ser Ser Arg Ser Asp Ser Arg Ser Asp Ser Arg Ser Asp
1               5                   10                  15

<210> SEQ ID NO 316
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 316

Ser Ser Ser Ser Ser Arg Ser Arg Ser Asp Ser Asp Ser Arg Ser Arg
1               5                   10                  15

<210> SEQ ID NO 317
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 317

Ser Ser Ser Ser Ser Glu Ser Lys Ser Glu Ser Lys Ser Glu Ser Lys
1               5                   10                  15

<210> SEQ ID NO 318
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 318

Ser Ser Ser Ser Ser Glu Ser Glu Ser Lys Ser Lys Ser Glu Ser Glu
1               5                   10                  15

<210> SEQ ID NO 319
<211> LENGTH: 16
<212> TYPE: PRT
```

```
<213> ORGANISM: Artificial Sequence
<220> FEATURE:
<223> OTHER INFORMATION: Synthetic hydrophobic tail

<400> SEQUENCE: 319

Ser Ser Ser Ser Ser Arg Ser Glu Ser Arg Ser Glu Ser Arg Ser Glu
1               5                   10                  15

<210> SEQ ID NO 320
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 320

Ser Ser Ser Ser Ser Arg Ser Arg Ser Glu Ser Glu Ser Arg Ser Glu
1               5                   10                  15

<210> SEQ ID NO 321
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 321

Ser Ser Ser Ser Ser Lys Ser Asp Ser Lys Ser Asp Ser Lys Ser Asp
1               5                   10                  15

<210> SEQ ID NO 322
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 322

Ser Ser Ser Ser Ser Glu Ser His Ser Glu Ser His Ser Glu Ser His
1               5                   10                  15

<210> SEQ ID NO 323
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 323

Ser Ser Ser Ser Ser Glu Ser Glu Ser His Ser His Ser Glu Ser Glu
1               5                   10                  15

<210> SEQ ID NO 324
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 324

Ser Ser Ser Ser Ser Arg Ser Arg Ser Arg Ser Arg Ser Arg Ser Arg
1               5                   10                  15

<210> SEQ ID NO 325
<211> LENGTH: 16
<212> TYPE: PRT
<213> ORGANISM: Artificial Sequence
```

-continued

```
<220> FEATURE:
<223> OTHER INFORMATION: Synthetic hydrophobic tail

<400> SEQUENCE: 325

Ser Ser Ser Ser Ser Arg Ser Arg Ser Arg Ser Asp Ser Asp
1               5                   10                  15

<210> SEQ ID NO 326
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 326

Ser Ser Ser Ser Ser Arg Ser Arg Ser Arg Ser Asp Ser Asp Ser Asp
1               5                   10                  15

<210> SEQ ID NO 327
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 327

Ser Ser Ser Ser Ser His Ser Asp Ser His Ser Asp Ser His Ser Asp
1               5                   10                  15

<210> SEQ ID NO 328
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 328

Ser Ser Ser Ser Ser His Ser His Ser His Ser His Ser His Ser His
1               5                   10                  15

<210> SEQ ID NO 329
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 329

Ser Ser Ser Ser Ser His Ser Asp Ser Asp Ser His Ser Asp Ser Asp
1               5                   10                  15

<210> SEQ ID NO 330
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 330

Ser Ser Ser Ser Ser His Ser Glu Ser Glu Ser His Ser Glu Ser Glu
1               5                   10                  15

<210> SEQ ID NO 331
<211> LENGTH: 16
<212> TYPE: PRT
<213> ORGANISM: Artificial Sequence
<220> FEATURE:
```

<223> OTHER INFORMATION: Synthetic hydrophobic tail

<400> SEQUENCE: 331

Thr Thr Thr Thr Thr Arg Thr Asp Thr Arg Thr Asp Thr Arg Thr Asp
1               5                   10                  15

<210> SEQ ID NO 332
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 332

Thr Thr Thr Thr Thr Arg Thr Arg Thr Asp Thr Asp Thr Arg Thr Arg
1               5                   10                  15

<210> SEQ ID NO 333
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 333

Thr Thr Thr Thr Thr Glu Thr Lys Thr Glu Thr Lys Thr Glu Thr Lys
1               5                   10                  15

<210> SEQ ID NO 334
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 334

Thr Thr Thr Thr Thr Glu Thr Glu Thr Lys Thr Lys Thr Glu Thr Glu
1               5                   10                  15

<210> SEQ ID NO 335
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 335

Thr Thr Thr Thr Thr Arg Thr Glu Thr Arg Thr Glu Thr Arg Thr Glu
1               5                   10                  15

<210> SEQ ID NO 336
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 336

Thr Thr Thr Thr Thr Arg Thr Arg Thr Glu Thr Glu Thr Arg Thr Glu
1               5                   10                  15

<210> SEQ ID NO 337
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 337

Thr Thr Thr Thr Thr Lys Thr Asp Thr Lys Thr Asp Thr Lys Thr Asp
1               5                   10                  15

<210> SEQ ID NO 338
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 338

Thr Thr Thr Thr Thr Glu Thr His Thr Glu Thr His Thr Glu Thr His
1               5                   10                  15

<210> SEQ ID NO 339
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 339

Thr Thr Thr Thr Thr Glu Thr Glu Thr His Thr His Thr Glu Thr Glu
1               5                   10                  15

<210> SEQ ID NO 340
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 340

Thr Thr Thr Thr Thr Arg Thr Arg Thr Arg Thr Arg Thr Arg Thr Arg
1               5                   10                  15

<210> SEQ ID NO 341
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 341

Thr Thr Thr Thr Thr Arg Thr Arg Thr Arg Thr Arg Thr Asp Thr Asp
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 342

Thr Thr Thr Thr Thr Arg Thr Arg Thr Arg Thr Asp Thr Asp Thr Asp
1               5                   10                  15

<210> SEQ ID NO 343
<211> LENGTH: 16
<212> TYPE: PRT
<213> ORGANISM: Artificial Sequence
<220> FEATURE:
<223> OTHER INFORMATION: Synthetic hydrophobic tail

```
<400> SEQUENCE: 343

Thr Thr Thr Thr Thr His Thr Asp Thr His Thr Asp Thr His Thr Asp
1               5                   10                  15

<210> SEQ ID NO 344
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 344

Thr Thr Thr Thr Thr His Thr His Thr His Thr His Thr His Thr His
1               5                   10                  15

<210> SEQ ID NO 345
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 345

Thr Thr Thr Thr Thr His Thr Asp Thr Asp Thr His Thr Asp Thr Asp
1               5                   10                  15

<210> SEQ ID NO 346
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 346

Thr Thr Thr Thr Thr His Thr Glu Thr Glu Thr His Thr Glu Thr Glu
1               5                   10                  15

<210> SEQ ID NO 347
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 347

Cys Cys Cys Cys Cys Arg Cys Asp Cys Arg Cys Asp Cys Arg Cys Asp
1               5                   10                  15

<210> SEQ ID NO 348
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 348

Cys Cys Cys Cys Cys Arg Cys Arg Cys Asp Cys Asp Cys Arg Cys Arg
1               5                   10                  15

<210> SEQ ID NO 349
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 349
```

Cys Cys Cys Cys Cys Glu Cys Lys Cys Glu Cys Lys Cys Glu Cys Lys
1               5                   10                  15

<210> SEQ ID NO 350
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 350

Cys Cys Cys Cys Cys Glu Cys Glu Cys Lys Cys Lys Cys Glu Cys Glu
1               5                   10                  15

<210> SEQ ID NO 351
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 351

Cys Cys Cys Cys Cys Arg Cys Glu Cys Arg Cys Glu Cys Arg Cys Glu
1               5                   10                  15

<210> SEQ ID NO 352
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 352

Cys Cys Cys Cys Cys Arg Cys Arg Cys Glu Cys Glu Cys Arg Cys Glu
1               5                   10                  15

<210> SEQ ID NO 353
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 353

Cys Cys Cys Cys Cys Lys Cys Asp Cys Lys Cys Asp Cys Lys Cys Asp
1               5                   10                  15

<210> SEQ ID NO 354
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 354

Cys Cys Cys Cys Cys Glu Cys His Cys Glu Cys His Cys Glu Cys His
1               5                   10                  15

<210> SEQ ID NO 355
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 355

Cys Cys Cys Cys Cys Glu Cys Glu Cys His Cys His Cys Glu Cys Glu
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 356

Cys Cys Cys Cys Cys Arg Cys Arg Cys Arg Cys Arg Cys Arg Cys Arg
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 357

Cys Cys Cys Cys Cys Arg Cys Arg Cys Arg Cys Arg Cys Asp Cys Asp
1               5                   10                  15

<210> SEQ ID NO 358
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 358

Cys Cys Cys Cys Cys Arg Cys Arg Cys Arg Cys Asp Cys Asp Cys Asp
1               5                   10                  15

<210> SEQ ID NO 359
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 359

Cys Cys Cys Cys Cys His Cys Asp Cys His Cys Asp Cys His Cys Asp
1               5                   10                  15

<210> SEQ ID NO 360
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 360

Cys Cys Cys Cys Cys His Cys His Cys His Cys His Cys His Cys His
1               5                   10                  15

<210> SEQ ID NO 361
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 361

Cys Cys Cys Cys Cys His Cys Asp Cys Asp Cys His Cys Asp Cys Asp

```
<210> SEQ ID NO 362
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 362

Cys Cys Cys Cys Cys His Cys Glu Cys Glu Cys His Cys Glu Cys Glu
1               5                   10                  15

<210> SEQ ID NO 363
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 363

Tyr Tyr Tyr Tyr Tyr Arg Tyr Asp Tyr Arg Tyr Asp Tyr Arg Tyr Asp
1               5                   10                  15

<210> SEQ ID NO 364
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 364

Tyr Tyr Tyr Tyr Tyr Arg Tyr Arg Tyr Asp Tyr Asp Tyr Arg Tyr Arg
1               5                   10                  15

<210> SEQ ID NO 365
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 365

Tyr Tyr Tyr Tyr Tyr Glu Tyr Lys Tyr Glu Tyr Lys Tyr Glu Tyr Lys
1               5                   10                  15

<210> SEQ ID NO 366
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 366

Tyr Tyr Tyr Tyr Tyr Glu Tyr Glu Tyr Lys Tyr Lys Tyr Glu Tyr Glu
1               5                   10                  15

<210> SEQ ID NO 367
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 367

Tyr Tyr Tyr Tyr Tyr Arg Tyr Glu Tyr Arg Tyr Glu Tyr Arg Tyr Glu
1               5                   10                  15
```

```
<210> SEQ ID NO 368
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 368

Tyr Tyr Tyr Tyr Tyr Arg Tyr Arg Tyr Glu Tyr Glu Tyr Arg Tyr Glu
1               5                   10                  15

<210> SEQ ID NO 369
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 369

Tyr Tyr Tyr Tyr Tyr Glu Tyr His Tyr Glu Tyr His Tyr Glu Tyr His
1               5                   10                  15

<210> SEQ ID NO 370
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 370

Tyr Tyr Tyr Tyr Tyr Glu Tyr Glu Tyr His Tyr His Tyr Glu Tyr Glu
1               5                   10                  15

<210> SEQ ID NO 371
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 371

Tyr Tyr Tyr Tyr Tyr Arg Tyr Arg Tyr Arg Tyr Arg Tyr Arg Tyr Arg
1               5                   10                  15

<210> SEQ ID NO 372
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 372

Tyr Tyr Tyr Tyr Tyr Arg Tyr Arg Tyr Arg Tyr Arg Tyr Asp Tyr Asp
1               5                   10                  15

<210> SEQ ID NO 373
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 373

Tyr Tyr Tyr Tyr Tyr Arg Tyr Arg Tyr Arg Tyr Asp Tyr Asp Tyr Asp
1               5                   10                  15
```

<210> SEQ ID NO 374
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 374

Tyr Tyr Tyr Tyr Tyr His Tyr Asp Tyr His Tyr Asp Tyr His Tyr Asp
1               5                   10                  15

<210> SEQ ID NO 375
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 375

Tyr Tyr Tyr Tyr Tyr His Tyr His Tyr His Tyr His Tyr His Tyr His
1               5                   10                  15

<210> SEQ ID NO 376
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 376

Tyr Tyr Tyr Tyr Tyr His Tyr Asp Tyr Asp Tyr His Tyr Asp Tyr Asp
1               5                   10                  15

<210> SEQ ID NO 377
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 377

Tyr Tyr Tyr Tyr Tyr His Tyr Glu Tyr Glu Tyr His Tyr Glu Tyr Glu
1               5                   10                  15

<210> SEQ ID NO 378
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 378

Asn Asn Asn Asn Asn Arg Asn Asp Asn Arg Asn Asp Asn Arg Asn Asp
1               5                   10                  15

<210> SEQ ID NO 379
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 379

Asn Asn Asn Asn Asn Arg Asn Arg Asn Asp Asn Asp Asn Arg Asn Arg
1               5                   10                  15

```
<210> SEQ ID NO 380
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 380

Asn Asn Asn Asn Asn Glu Asn Lys Asn Glu Asn Lys Asn Glu Asn Lys
1               5                   10                  15

<210> SEQ ID NO 381
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 381

Asn Asn Asn Asn Asn Glu Asn Glu Asn Lys Asn Lys Asn Glu Asn Glu
1               5                   10                  15

<210> SEQ ID NO 382
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 382

Asn Asn Asn Asn Asn Arg Asn Glu Asn Arg Asn Glu Asn Arg Asn Glu
1               5                   10                  15

<210> SEQ ID NO 383
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 383

Asn Asn Asn Asn Asn Arg Asn Arg Asn Glu Asn Glu Asn Arg Asn Glu
1               5                   10                  15

<210> SEQ ID NO 384
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 384

Asn Asn Asn Asn Asn Lys Asn Asp Asn Lys Asn Asp Asn Lys Asn Asp
1               5                   10                  15

<210> SEQ ID NO 385
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 385

Asn Asn Asn Asn Asn Glu Asn His Asn Glu Asn His Asn Glu Asn His
1               5                   10                  15

<210> SEQ ID NO 386
```

```
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 386

Asn Asn Asn Asn Asn Glu Asn Glu Asn His Asn His Asn Glu Asn Glu
1               5                   10                  15

<210> SEQ ID NO 387
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 387

Asn Asn Asn Asn Asn Arg Asn Arg Asn Arg Asn Arg Asn Arg Asn Arg
1               5                   10                  15

<210> SEQ ID NO 388
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 388

Asn Asn Asn Asn Asn Arg Asn Arg Asn Arg Asn Arg Asn Asp Asn Asp
1               5                   10                  15

<210> SEQ ID NO 389
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 389

Asn Asn Asn Asn Asn Arg Asn Arg Asn Arg Asn Asp Asn Asp Asn Asp
1               5                   10                  15

<210> SEQ ID NO 390
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 390

Asn Asn Asn Asn Asn His Asn Asp Asn His Asn Asp Asn His Asn Asp
1               5                   10                  15

<210> SEQ ID NO 391
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 391

Asn Asn Asn Asn Asn His Asn His Asn His Asn His Asn His Asn His
1               5                   10                  15

<210> SEQ ID NO 392
<211> LENGTH: 16
```

<212> TYPE: PRT
<213> ORGANISM: Artificial Sequence
<220> FEATURE:
<223> OTHER INFORMATION: Synthetic hydrophobic tail

<400> SEQUENCE: 392

Asn Asn Asn Asn Asn His Asn Asp Asn Asp Asn His Asn Asp Asn Asp
1               5                   10                  15

<210> SEQ ID NO 393
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 393

Asn Asn Asn Asn Asn His Asn Glu Asn Glu Asn His Asn Glu Asn Glu
1               5                   10                  15

<210> SEQ ID NO 394
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 394

Gln Gln Gln Gln Gln Arg Gln Asp Gln Arg Gln Asp Gln Arg Gln Asp
1               5                   10                  15

<210> SEQ ID NO 395
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 395

Gln Gln Gln Gln Gln Arg Gln Arg Gln Asp Gln Asp Gln Arg Gln Arg
1               5                   10                  15

<210> SEQ ID NO 396
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 396

Gln Gln Gln Gln Gln Glu Gln Lys Gln Glu Gln Lys Gln Glu Gln Lys
1               5                   10                  15

<210> SEQ ID NO 397
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 397

Gln Gln Gln Gln Gln Glu Gln Glu Gln Lys Gln Lys Gln Glu Gln Glu
1               5                   10                  15

<210> SEQ ID NO 398
<211> LENGTH: 16
<212> TYPE: PRT

<213> ORGANISM: Artificial Sequence
<220> FEATURE:
<223> OTHER INFORMATION: Synthetic hydrophobic tail

<400> SEQUENCE: 398

Gln Gln Gln Gln Gln Arg Gln Glu Gln Arg Gln Glu Gln Arg Gln Glu
1               5                   10                  15

<210> SEQ ID NO 399
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 399

Gln Gln Gln Gln Gln Arg Gln Arg Gln Glu Gln Glu Gln Arg Gln Glu
1               5                   10                  15

<210> SEQ ID NO 400
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 400

Gln Gln Gln Gln Gln Lys Gln Asp Gln Lys Gln Asp Gln Lys Gln Asp
1               5                   10                  15

<210> SEQ ID NO 401
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 401

Gln Gln Gln Gln Gln Glu Gln His Gln Glu Gln His Gln Glu Gln His
1               5                   10                  15

<210> SEQ ID NO 402
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 402

Gln Gln Gln Gln Gln Glu Gln Glu Gln His Gln His Gln Glu Gln Glu
1               5                   10                  15

<210> SEQ ID NO 403
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 403

Gln Gln Gln Gln Gln Arg Gln Arg Gln Arg Gln Arg Gln Arg Gln Arg
1               5                   10                  15

<210> SEQ ID NO 404
<211> LENGTH: 16
<212> TYPE: PRT
<213> ORGANISM: Artificial Sequence

```
<220> FEATURE:
<223> OTHER INFORMATION: Synthetic hydrophobic tail

<400> SEQUENCE: 404

Gln Gln Gln Gln Gln Arg Gln Arg Gln Arg Gln Asp Gln Asp
1               5                   10                  15

<210> SEQ ID NO 405
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 405

Gln Gln Gln Gln Gln Arg Gln Arg Gln Arg Gln Asp Gln Asp Gln Asp
1               5                   10                  15

<210> SEQ ID NO 406
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 406

Gln Gln Gln Gln Gln His Gln Asp Gln His Gln Asp Gln His Gln Asp
1               5                   10                  15

<210> SEQ ID NO 407
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 407

Gln Gln Gln Gln Gln His Gln His Gln His Gln His Gln His Gln His
1               5                   10                  15

<210> SEQ ID NO 408
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 408

Gln Gln Gln Gln Gln His Gln Asp Gln Asp Gln His Gln Asp Gln Asp
1               5                   10                  15

<210> SEQ ID NO 409
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 409

Gln Gln Gln Gln Gln His Gln Glu Gln Glu Gln His Gln Glu Gln Glu
1               5                   10                  15
```

```
<210> SEQ ID NO 410
<211> LENGTH: 16
<212> TYPE: PRT
<213> ORGANISM: Artificial Sequence
<220> FEATURE:
<223> OTHER INFORMATION: Synthetic hydrophobic tail

<400> SEQUENCE: 410

Tyr Tyr Tyr Tyr Tyr Lys Tyr Asp Tyr Lys Tyr Asp Tyr Lys Tyr Asp
1               5                  10                  15
```

TREATMENT OF LEAKY OR DAMAGED TIGHT JUNCTIONS AND ENHANCING EXTRACELLULAR MATRIX

CROSS-REFERENCE TO RELATED APPLICATIONS

This application claims priority to U.S. Ser. No. 60/894,872, filed on Mar. 14, 2007.

FIELD OF THE INVENTION

The present application is in the field of materials to alter or enhance cell matrix deposition around tissues, especially blood vessels, connective tissue and tissues with tight junctions.

BACKGROUND OF THE INVENTION

There are a number of disorders associated with leakage around blood vessels and within the tight junctions between cells. Such leakage can lead to fluid invading the tissues, causing a loss in blood pressure, organ dysfunction or failure, and death. Many of these disorders are a result of massive cell death, such as that associated with chemotherapy of a large tumor, sepsis following systemic bacterial infection, inflammation associated with burns, and large surgical resections.

Severe sepsis results from the body's systemic over-response to infection. This over-response disrupts homeostasis through an uncontrolled cascade of inflammation, coagulation, and impaired fibrinolysis. Deranged micro-circulatory function leads to global tissue hypoxia and direct tissue damage. This ultimately results in organ failure, and often, death. Anti-infectives, resuscitation, and supportive care do not necessarily prevent the progressive organ dysfunction that occurs in many patients. Microcirculatory dysfunction may persist despite adequate global values of oxygen delivery, making resuscitation procedures ineffective.

The "leaky gut" hypothesis proposes that leakage of enteric bacteria into the body resulting from disruption of the epithelial barrier is a critical step in the pathophysiology of various disorders such as inflammatory bowel disease and sepsis.

One third of women undergoing mastectomy with axillary evacuation for primary breast cancer suffer from postoperative seromas leading to unnecessary costs and complications such as infections and new operations. Different methods to prevent seroma formation have been tried without permanent success.

Another condition for which there are insufficient treatments is the loss of fluid which occurs due to sepsis or burns, where the junctions between cells begin to leak interstitial fluid, causing dehydration, electrolyte imbalance, and cell death.

These disorders can lead to further complications when the release of inflammatory molecules from the damaged tissue elicits further tissue damage.

U.S. Pat. Nos. 5,670,483, 6,548,630, and 7,098,028 by Zhang et al. describe amphiphilic peptides having alternating hydrophobic and hydrophilic residues. Zhang alleges that the membranes are potentially useful in biomaterial applications such as slow-diffusion drug delivery systems, artificial skin, and separation matrices, and as experimental models for Alzheimer's disease and scrapie infection. However, Zhang does not disclose the use of such materials for treatment and support of disorders associated with leaky, damaged tight junction and weak, diseased, or injured extracellular matrix.

WO 2007/142757 and U.S. Ser. No. 11/411,745 describe compositions including peptides with alternating hydrophilic and hydrophobic monomers that allow them to self-assemble under physiological conditions are formulated for application to wounds. However, these applications do not describe the use of such materials for treatment and support of disorders associated with leaky, damaged tight junction and weak, diseased, or injured extracellular matrix.

It is therefore an object of the present invention to provide a methods and compositions for treating conditions involving not just fluid leakage but pathophysiology of the junctions between cells.

It is another object of the present invention to provide methods and compositions for increasing extracellular matrix around vascular cells.

It is still a further object of the present invention to provide methods and compositions for repairing or strengthening tight-junctions.

SUMMARY OF THE INVENTION

Self assembling peptides and peptidomimetics can be utilized for the treatment and support of disorders associated with leaky, damaged tight junction and weak, diseased, or injured extracellular matrix. The self-assembling materials can anchor or interact with the structural extracellular matrix (ECM) at the edges of blood vessels and/or tissues.

The self-assembling materials generally have alternating hydrophilic or hydrophobic residues or hydrophobic and/or hydrophilic sections which allow the material to react or interact with the glycoproteins found in the ECM. For example, the self-assembling peptides can have a segment of residues having a positive charge under physiological conditions joined to a segment of residues having a negative charge under physiological conditions.

In another embodiment, the self-assembling peptide has a first hydrophobic region operably linked to a first hydrophilic region. The first hydrophobic region can include a segment of amino acid residues that have hydrophobic side chains under physiological conditions and the first hydrophilic region can include a segment of amino acid residues that have hydrophilic side chains under physiological conditions.

In yet another embodiment, the self-assembling material is formed by mixing together a segment of residues having positive charges under physiological conditions with a segment of residues having negative charges under physiological conditions. In certain embodiments, strings of positively charged amino acids will alternate with strings of negatively charged amino acids to form a multilayered structure.

In still another embodiment, the self-assembling peptides contain hydrophilic polar amino acid residues and hydrophobic non-polar amino acid residues under physiological conditions. The one or more hydrophilic residues can alternate with one or more hydrophobic residues. For example, the amino acid sequence of a representative self-assembling peptide can be GQGQ (SEQ ID NO: 1), GGQQGG (SEQ ID NO: 2), GQQGQQG (SEQ ID NO: 3), GGQGGQGG (SEQ ID NO: 4), etc. It will be appreciated that the partitioning of the self-assembling peptide into a polar or non-polar environment can be controlled by altering the ratio of hydrophobic amino acid residues to hydrophilic amino acid residues, wherein a ratio greater than 1:1 indicates that the peptide partitions more in hydrophobic conditions compared to hydrophilic conditions. A ratio of less than 1:1 indicates that the peptide partitions more in hydrophilic conditions compared to hydrophobic conditions.

The materials described above can be administered alone, or in combination with each other, or other self-assembling materials.

The self-assembling materials preferably do not cause any secondary toxicity when degraded in the body. Further, the break down product of the self-assembling materials may enhance growth and repair of the surrounding tissues.

The formulations can be administered by injection, spraying, topically or by catheter or via a wound dressing or other material to which it is applied and then applied to the site in need of treatment.

DETAILED DESCRIPTION OF THE INVENTION

I. Definitions

Figure 1:
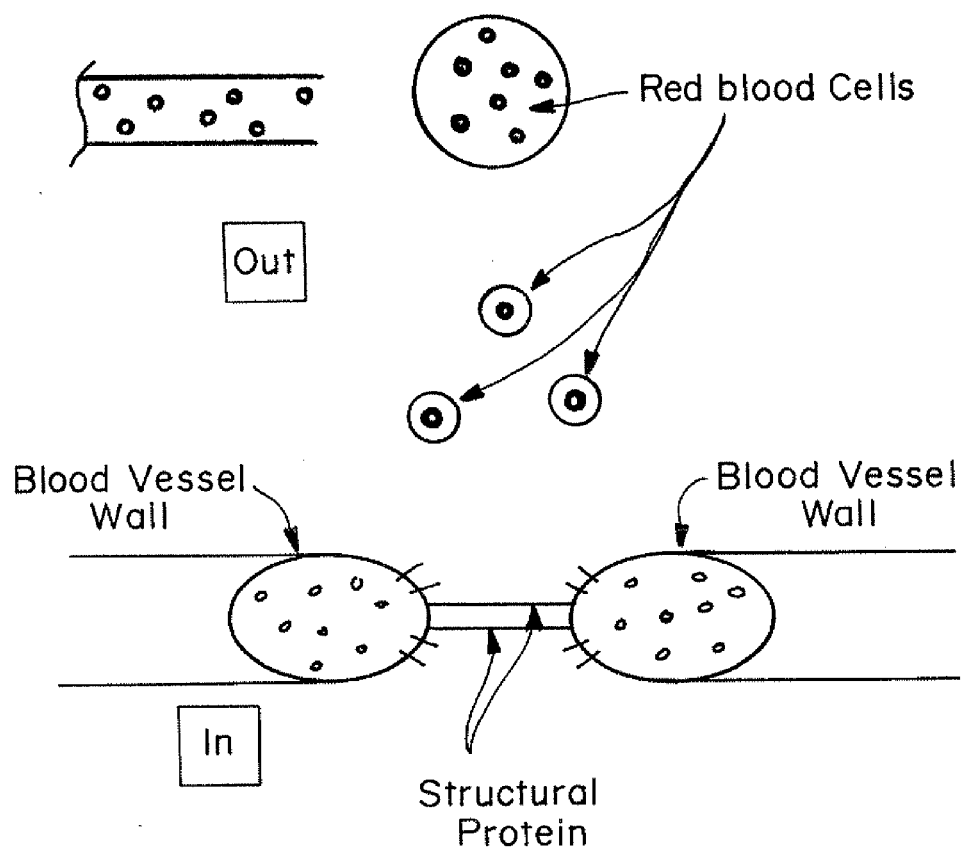
FIG. 1 shows the extension of extracellular matrix using self-assembling peptides. The peptides contain one or more tail moieties that bind to or interact with the extracellular matrix of a vessel or tissue, such as a blood vessel, thus anchoring the peptides to the vessel.

"Biocompatible", as used herein, refers to compatibility with living tissue or a living system by not being toxic, injurious, or physiologically reactive and not causing immunological rejection.

"Complementary" means having the capability of forming ionic or hydrogen bonding interactions between hydrophilic residues from adjacent peptides in a structure. Each hydrophilic reside in a peptide either hydrogen bonds or ionically pairs with a hydrophilic residue on an adjacent peptide, or is exposed to solvent. Pairing may also involve van der Waals forces.

"Effective amount", in reference to an active agent such as a self-assembling peptide or biomolecule, pharmaceutical agent, etc. refers to the amount necessary to elicit a desired biological response. As will be appreciated by those of ordinary skill in this art, the effective amount of an agent may vary depending on such factors as the desired biological endpoint, the agent to be delivered, the nature of the site to which the agent is delivered, the nature of the conditions for which the agent is administered, etc. For example, the effective amount of a composition for treatment of diabetic retinopathy may be an amount sufficient to promote recovery to a greater extent than would occur in the absence of the composition.

"Hemostasis" refers to the cessation of bleeding.

"Preventing" refers to causing a condition, state, or disease, or symptom or manifestation of such, or worsening of the severity of such, not to occur. Preventing includes reducing the risk that a condition, state, or disease, or symptom or manifestation of such, or worsening of the severity of such, will occur.

"Repair", as used in reference to the repair of tissue in various embodiments, may include any aspect of anatomical or functional restoration of the condition of the tissue prior to an injury, deterioration, or other damage. For example, it may include restoration of physical continuity between portions of tissue that were separated by injury, deterioration, or other damage. Preferably such restoration of physical continuity includes reposition or reconnection of the portions of tissue without appreciable separation by tissue of a type that was not present prior to the injury, such as scar tissue. Repair may, but need not, include growth or development of new tissue. "Repair" and "Healing" are used interchangeably herein.

II. Self-Assembling Materials

Self-assembling materials that can anchor or interact with the structural extracellular matrix (ECM) at the edges of blood vessels and/or tissues are described herein. These self-assembling materials typically have hydrophobic and/or hydrophilic residues or sections which allow the material to react or interact with the glycoproteins found in the ECM.

Preferably, the self-assembling materials do not cause any secondary toxicity when they break down. Further, the break down product of the self-assembling materials may enhance growth and repair of the surrounding tissues.

These materials may form nanoparticles. It is important to keep the size of the nanoparticles smaller than 10-20 nm to avoid unwanted immune response.

A. Self-Assembling Peptides

In one embodiment, the self-assembling material is a self-assembling peptide. The term "peptide," as used herein includes "polypeptide," "oligopeptide," and "protein," and refers to a chain of at least two α-amino acid residues linked together by covalent bonds (e.g., peptide bonds). Useful peptides can vary in length so long as they retain the ability to self-assemble to an extent useful for one or more of the purposes described herein. The number of amino acid residues in the peptide may range from as few as two α-amino acid residues to about 200 residues. Typically, peptides which self-assemble have from about 6 to about 200 residues, preferably from about 6 to about 64 residues, more preferably from about 8 to about 36 residues, most preferably from about 8 to about 24 residues. Peptides that are less than 100 amino acid residues long, more preferably less than approximately 50 amino acids in length, may assemble more readily. In one embodiment, the peptide has from about 8 to about 16 residues. In another embodiment, the peptide has from about 12 to about 20 residues. In yet another embodiment, the peptide has from about 16 to about 20 residues. "Peptide" may refer to an individual peptide or to a collection of peptides having the same or different sequences, any of which may contain naturally occurring α-amino acid residues, non-naturally occurring α-amino acid residues, and combinations thereof. α-Amino acid analogs are also known in the art and may alternatively be employed. In particular, D-α-amino acid residues may be used.

In addition, one or more of the amino acid residues in a self-assembling peptide can be altered or derivatized by the addition of one or more chemical entities including, but not limited to, acyl groups, carbohydrate groups, carbohydrate chains, phosphate groups, farnesyl groups, isofarnesyl groups, fatty acid groups, or a linker which allows for conjugation or functionalization of the peptide. For example, either or both ends of a given peptide can be modified. For example, the carboxyl and/or amino groups of the carboxyl- and amino-terminal residues, respectively can be protected or not protected. The charge at a terminus can also be modified. For example, a group or radical such as an acyl group (RCO—, where R is an organic group (e.g., an acetyl group ($CH_3CO$—)) can be present at the N-terminus of a peptide to neutralize an "extra" positive charge that may otherwise be present (e.g., a charge not resulting from the side chain of the N-terminal amino acid). Similarly, a group such as an amine group (RNH—, where R is an organic group (e.g., an amino group —$NH_2$)) can be used to neutralize an "extra" negative charge that may otherwise be present at the C-terminus (e.g., a charge not resulting from the side chain of the C-terminal amino acid residue). Where an amine is used, the C-terminus bears an amide (—CONHR). The neutralization of charges on a terminus may facilitate self-assembly. One of ordinary skill in the art will be able to select other suitable groups.

Useful peptides can also be branched, in which case they will contain at least two amino acid polymers, each of which consists of at least three amino acid residues joined by peptide bonds. The two amino acid polymers may be linked by a bond other than a peptide bond.

While the sequences of the peptides can vary, useful sequences include those that convey an amphiphilic nature to the peptides (e.g., the peptides can contain approximately equal numbers of hydrophobic and hydrophilic amino acid residues), and the peptides can be complementary and structurally compatible. Any naturally occurring or non-naturally occurring hydrophilic or hydrophobic residue can be used. Hydrophilic residues are those residues that typically contain a polar functional group or a functional group that is charged at physiological conditions. Exemplary functional groups include, but are not limited to, carboxylic acid groups, amino groups, sulfate groups, hydroxy groups, halogen groups, nitro groups, phosphate groups, etc. Hydrophobic residues are those residues that contain non-polar functional groups. Exemplary functional groups include, but are not limited to, alkyl groups, alkene groups, alkyne groups, and phenyl groups.

In one embodiment, the hydrophilic residue has the formula —NH—CH(X)—COO—, wherein X has the formula $(CH_2)_y Z$, wherein y=0-8, preferably 1-6, more preferably 1-4 and most preferably 1-3, and Z is a polar or charged functional group such as a carboxylic acid group, amino groups, sulfate group, hydroxy group, halogen group, nitro group, phosphate groups, or functional groups containing a quaternary amine. The alkyl chain can be in a linear, branched, or cyclic arrangement. X may also contain one or more heteroatoms within the alkyl chain and/or X may be substituted with one or more additional substituents. In a preferred embodiment, Z is a carboxylic acid group or an amino group. In one embodiment, the hydrophobic residue has the formula —NH—CH(X)—COO—, wherein X has the formula $(CH_2)_y Z$, wherein y 0-8, preferably 1-6, more preferably 1-4, and more preferably 1-3, and Z is a non-polar functional group such as an alkyl group, alkylene group, alkyne group, or a phenyl group. The alkyl chain can be in a linear, branched, or cyclic arrangement. X may also contain one or more heteroatoms within the alkyl chain and/or X may be substituted with one or more additional substituents. In a preferred embodiment, X is an alkyl group, such as a methyl group.

Complementary peptides have the ability to form ionic or hydrogen bonds between residues (e.g., hydrophilic residues) on adjacent peptides in a structure. For example, one or more hydrophilic residues in a peptide can either hydrogen bond or ionically pair with one or more hydrophilic residues on an adjacent peptide. Unpaired residues can interact (e.g. form hydrogen bonds, etc,) with the solvent. Peptide-peptide interactions may also involve van der Waals forces and/or forces that do not constitute covalent bonds. The peptides are structurally compatible when they are capable of maintaining a sufficiently constant intrapeptide distance to allow self-assembly and structure formation. The intrapeptide distance can vary. "Intrapeptide distance", as used herein, refers to the average of a representative number of distances between adjacent amino acid residues. In one embodiment, the intrapeptide distance is less than about 4 angstroms, preferably less than about 3, more preferably less than about 2 angstroms, and most preferably less than about 1 angstrom. The intrapeptide distance may be larger than this, however. These distances can be calculated based on molecular modeling or based on a simplified procedure described in U.S. Pat. No. 5,670,483 to Zhang et al.

The structures described herein can be formed through self-assembly of the peptides described in U.S. Pat. Nos. 5,670,483; 5,955,343; 6,548,630; and 6,800,481 to Zhang et al.; Holmes et al., *Proc. Natl. Acad. Sci. USA*, 97:6728-6733 (2000); Zhang et al., *Proc. Natl. Acad. Sci. USA*, 90:3334-3338 (1993); Zhang et al., *Biomaterials*, 16:1385-1393 (1995); Caplan et al., *Biomaterials*, 23:219-227 (2002); Leon et al., *J. Biomater. Sci. Polym. Ed.*, 2:297-312 (1998); and Caplan et al., *Biomacromolecules*, 1:627-631 (2000).

Self-assembling peptides containing alternating hydrophobic and hydrophilic amino residues can be used. Examples of representative hydrophobic and hydrophilic peptides are listed in Table 1.

TABLE 1

Representative Self-Assembling Peptides

| No. | Sequence (N → C) | |
|---|---|---|
| 1. | n-SGSGSGSGSGSGSGSG-c | (SEQ ID NO: 5) |
| 2. | n-SASASASASASASASA-c | (SEQ ID NO: 6) |
| 3. | n-SVSVSVSVSVSVSVSV-c | (SEQ ID NO: 7) |
| 4. | n-SLSLSLSLSLSLSLSL-c | (SEQ ID NO: 8) |
| 5. | n-SISISISISISISISI-c | (SEQ ID NO: 9) |
| 6. | n-SMSMSMSMSMSMSMSM-c | (SEQ ID NO: 10) |
| 7. | n-SFSFSFSFSFSFSFSF-c | (SEQ ID NO: 11) |
| 8. | n-SWSWSWSWSWSWSWSW-c | (SEQ ID NO: 12) |
| 9. | n-SPSPSPSPSPSPSPSP-c | (SEQ ID NO: 13) |
| 10. | n-TGTGTGTGTGTGTGTG-c | (SEQ ID NO: 14) |
| 11. | n-TATATATATATATATA-c | (SEQ ID NO: 15) |
| 12. | n-TVTVTVTVTVTVTVTV-c | (SEQ ID NO: 16) |
| 13. | n-TLTLTLTLTLTLTLTL-c | (SEQ ID NO: 17) |
| 14. | n-TITITITITITITITI-c | (SEQ ID NO: 18) |
| 15. | n-TMTMTMTMTMTMTMTM-c | (SEQ ID NO: 19) |
| 16. | n-TFTFTFTFTFTFTFTF-c | (SEQ ID NO: 20) |
| 17. | n-TWTWTWTWTWTWTWTW-c | (SEQ ID NO: 21) |
| 18. | n-TPTPTPTPTPTPTPTP-c | (SEQ ID NO: 22) |
| 19. | n-CGCGCGCGCGCGCGCG-c | (SEQ ID NO: 23) |
| 20. | n-CACACACACACACACA-c | (SEQ ID NO: 24) |
| 21. | n-CVCVCVCVCVCVCVCV-c | (SEQ ID NO: 25) |
| 22. | n-CLCLCLCLCLCLCLCL-c | (SEQ ID NO: 26) |
| 23. | n-CICICICICICICICI-c | (SEQ ID NO: 27) |
| 24. | n-CMCMCMCMCMCMCMCM-c | (SEQ ID NO: 28) |
| 25. | n-CFCFCFCFCFCFCFCF-c | (SEQ ID NO: 29) |
| 26. | n-CWCWCWCWCWCWCWC-c | (SEQ ID NO: 30) |
| 27. | n-CPCPCPCPCPCPCPCP-c | (SEQ ID NO: 31) |
| 28. | n-YGYGYGYGYGYGYGYG-c | (SEQ ID NO: 32) |
| 29. | n-YAYAYAYAYAYAYAYA-c | (SEQ ID NO: 33) |
| 30. | n-YVYVYVYVYVYVYVYV-c | (SEQ ID NO: 34) |
| 31. | n-YLYLYLYLYLYLYLYL-c | (SEQ ID NO: 35) |

TABLE 1-continued

Representative Self-Assembling Peptides

| No. | Sequence (N → C) | |
|---|---|---|
| 32. | n-YIYIYIYIYIYIYIYI-c | (SEQ ID NO: 36) |
| 33. | n-YMYMYMYMYMYMYMYM-c | (SEQ ID NO: 37) |
| 34. | n-YFYFYFYFYFYFYFYF-c | (SEQ ID NO: 38) |
| 35. | n-YWYWYWYWYWYWYWYW-c | (SEQ ID NO: 39) |
| 36. | n-YPYPYPYPYPYPYPYP-c | (SEQ ID NO: 40) |
| 37. | n-NGNGNGNGNGNGNGNG-c | (SEQ ID NO: 41) |
| 38. | n-NANANANANANANANA-c | (SEQ ID NO: 42) |
| 39. | n-NVNVNVNVNVNVNVNV-c | (SEQ ID NO: 43) |
| 40. | n-NLNLNLNLNLNLNLNL-c | (SEQ ID NO: 44) |
| 41. | n-NININININININI-c | (SEQ ID NO: 45) |
| 42. | n-NMNMNMNMNMNMNMNM-c | (SEQ ID NO: 46) |
| 43. | n-NFNFNFNFNFNFNFNF-c | (SEQ ID NO: 47) |
| 44. | n-NWNWNWNWNWNWNWNW-c | (SEQ ID NO: 48) |
| 45. | n-NPNPNPNPNPNPNPNP-c | (SEQ ID NO: 49) |
| 46. | n-QGQGQGQGQGQGQGQG-c | (SEQ ID NO: 50) |
| 47. | n-QAQAQAQAQAQAQAQA-c | (SEQ ID NO: 51) |
| 48. | n-QVQVQVQVQVQVQVQV-c | (SEQ ID NO: 52) |
| 49. | n-QLQLQLQLQLQLQLQL-c | (SEQ ID NO: 53) |
| 50. | n-QIQIQIQIQIQIQIQI-c | (SEQ ID NO: 54) |
| 51. | n-QMQMQMQMQMQMQMQM-c | (SEQ ID NO: 55) |
| 52. | n-QFQFQFQFQFQFQFQF-c | (SEQ ID NO: 56) |
| 53. | n-QWQWQWQWQWQWQWQW-c | (SEQ ID NO: 57) |
| 54. | n-QPQPQPQPQPQPQPQP-c | (SEQ ID NO: 58) |
| 55. | n-AEAKAEAKAEAKAEAK-c | (SEQ ID NO: 59) |
| 56. | n-RADARADARADARADA-c | (SEQ ID NO: 60) |
| 57. | n-RAEARAEARAEARAEA-c | (SEQ ID NO: 61) |
| 58. | n-KADAKADAKADAKADA-c | (SEQ ID NO: 62) |

Other peptides or proteins can be used in combination or alternation with the disclosed self-assembling peptides or compositions. It will be appreciated that the additional peptides can include other self-assembling peptides or proteins. Alternatively, the peptide may be peptides that do not self-assemble. Representative additional peptides, proteins, or chemically modified variants thereof include, but are not limited to the peptides provided in Table 2.

TABLE 2

Additional Peptides

| | | |
|---|---|---|
| 1. | Pmp-Y(Me)-I-T-N-C-P-Orn-Y-NH₂ | (SEQ ID NO: 63) |
| 2. | Mpr-Y-F-Q-N-C-P-R | (SEQ ID NO: 64) |
| 3. | C-Y-F-Q-N-C-P-R-G-NH₂ | (SEQ ID NO: 65) |
| 4. | C-Y-F-Q-N-C-P-R | (SEQ ID NO: 66) |
| 5. | C-Y-Ile-Q-N-C-P-R-G-NH₂ | (SEQ ID NO: 67) |
| 6. | Y-F-Q-N-Asu-P-R-G-NH₂ | (SEQ ID NO: 68) |
| 7. | Y-Ile-Q-N-Asu-P-R-G-NH₂ | (SEQ ID NO: 69) |
| 8. | Mpr-D-PyridylAnine-F-Q-N-C-P-R-G-NH₂ | (SEQ ID NO: 70) |
| 9. | Deamino-Pen-Y-F-V-N-C-P-DR-G-NH₂ | (SEQ ID NO: 71) |
| 10. | Mpr-Y-F-Q-N-C-P-R-G-NH₂ | (SEQ ID NO: 72) |
| 11. | Mpr-Y-F-Q-N-C-P-DR-G-NH₂ | (SEQ ID NO: 73) |
| 12. | Mpr-Y-F-Q-N-C-P-K | (SEQ ID NO: 74) |
| 13. | C-Y-F-Q-N-C-P-K-G-NH₂ | (SEQ ID NO: 75) |
| 14. | C-Y-F-Q-N-C-P-K | (SEQ ID NO: 76) |
| 15. | Mpr-Y-F-V-N-C-P-DR-G-NH₂ | (SEQ ID NO: 77) |
| 16. | C-F-Ile-Q-N-C-P-Orn-G-NH₂ | (SEQ ID NO: 78) |
| 17. | Pmp-DY(OEt)-F-V-N-C-P-Cit-G-NH₂ | (SEQ ID NO: 79) |
| 18. | Pmp-Y(OEt)-F-V-N-C-P-R-G-NH₂ | (SEQ ID NO: 80) |
| 19. | Pmp-Y(Me)-F-Q-N-C-P-R-G-NH₂ | (SEQ ID NO: 81) |
| 20. | Pmp-Y(Me)-Ile-Q-N-C-P-Orn-G-NH₂ | (SEQ ID NO: 82) |
| 21. | G-DR-G-D-S-P | (SEQ ID NO: 83) |
| 22. | G-DR-G-D-S-P-A-S-S-K | (SEQ ID NO: 84) |
| 23. | G-P-R | |
| 24. | G-Pen-G-R-G-D-S-P-C-A | (SEQ ID NO: 85) |
| 25. | GRADSP | (SEQ ID NO: 86) |
| 26. | GRGD-DS-P | (SEQ ID NO: 87) |
| 27. | GRGDNP | (SEQ ID NO: 88) |
| 28. | GRGDS | (SEQ ID NO: 89) |
| 29. | GRGDSP | (SEQ ID NO: 90) |
| 30. | GRGDSPC | (SEQ ID NO: 91) |
| 31. | GRGDSPK | (SEQ ID NO: 92) |
| 32. | GRGDTP | (SEQ ID NO: 93) |
| 33. | GRGES | (SEQ ID NO: 94) |
| 34. | GRGESP | (SEQ ID NO: 95) |
| 35. | GRGETP | (SEQ ID NO: 96) |
| 36. | KGDS | (SEQ ID NO: 97) |
| 37. | GAVSTA | (SEQ ID NO: 98) |
| 38. | WTVPTA | (SEQ ID NO: 99) |
| 39. | TDVNGDGRHDL | (SEQ ID NO: 100) |

TABLE 2-continued

Additional Peptides

| | | |
|---|---|---|
| 40. | REDV | (SEQ ID NO: 101) |
| 41. | RGDC | (SEQ ID NO: 102) |
| 42. | RGDS | (SEQ ID NO: 103) |
| 43. | RGDSPASSKP | (SEQ ID NO: 104) |
| 44. | RGDT | (SEQ ID NO: 105) |
| 45. | RGDV | (SEQ ID NO: 106) |
| 46. | RGES | (SEQ ID NO: 107) |
| 47. | SDGR | (SEQ ID NO: 108) |
| 48. | SDGRG | (SEQ ID NO: 109) |
| 49. | YRGDS | (SEQ ID NO: 110) |
| 50. | EGVNDNEEGFFSAR | (SEQ ID NO: 111) |
| 51. | YADSGEGDFLAEGGGVR | (SEQ ID NO: 112) |
| 52. | Glp-GVNDNEEGFFSARY | (SEQ ID NO: 113) |

Pmp = pyridoxamine phosphate
Mpr = 3-mercaptopropionyl
Deamino-Pen = deamino penicillamine
Pen = penicillamine
Asu = amino succinyl
OEt = ethoxy Other useful self-assembling peptides can be generated, for example, which differ from those exemplified by a single amino acid residue or by multiple amino acid residues (e.g., by inclusion or exclusion of a repeating quartet). For example, one or more cysteine residues may be incorporated into the peptides, and these residues may bond with one another through the formation of disulfide bonds. Structures bonded in this manner may have increased mechanical strength relative to structures made with comparable peptides that do not include cysteine residues and thus are unable to form disulfide bonds.

The amino acid residues in the self-assembling peptides can be naturally occurring or non-naturally occurring amino acid residues. Naturally occurring amino acids can include amino acid residues encoded by the standard genetic code as well as non-standard amino acids (e.g., amino acids having the D-configuration instead of the L-configuration), as well as those amino acids that can be formed by modifications of standard amino acids (e.g. pyrrolysine or selenocysteine). Non-naturally occurring amino acids are not been found in nature, but can be incorporated into a peptide chain. Suitable non-naturally occurring amino acids include, but are not limited to, D-alloisoleucine(2R,3S)-2-amino-3-methylpentanoic acid, L-cyclopentyl glycine (S)-2-amino-2-cyclopentyl acetic acid. Other examples of non-naturally occurring amino acids can be found in textbooks or on the worldwide web (e.g., a site is maintained by the California Institute of Technology which displays structures of non-natural amino acids that have been successfully incorporated into functional proteins). Non-natural amino acid residues and amino acid derivatives are described in U.S. Patent Application Publication No. 2004/0204561 to Ellison.

Self-assembling peptides can be chemically synthesized or purified from natural or recombinantly-produced sources by methods well known in the art. For example, peptides can be synthesized using standard f-moc chemistry and purified using high pressure liquid chromatography (HPLC).

Where self-assembling peptides are used, it is thought that their side-chains (or R groups) partition into two faces, a polar face with side chains that have polar groups (e.g., side chains containing —OH, —NH, —CO$_2$H, or —SH groups) and a nonpolar face with side chains containing non-polar groups (e.g., the side chain of an alanine residue or residues having other hydrophobic groups).

Self-complementary peptides such as EAKA16-I (SEQ ID NO: 114), RADA16-I (SEQ ID NO: 60), RAEA16-I (SEQ ID NO: 61), and KADA16-I (SEQ ID NO: 62) are described in Zhang, S., et al. ((1999) Peptide self-assembly in functional polymer science and engineering. Reactive & Functional Polymers, 41, 91-102). The self-assembling peptides comprise a sequence of amino acid residues conforming to one or more of Formulas I-IV:

$$((Xaa^{neu}-Xaa^+)_x(Xaa^{neu}-Xaa^-)_y)_n \quad (I)$$

$$((Xaa^{neu}-Xaa^-)_x(Xaa^{neu}-Xaa^+)_y)_n \quad (II)$$

$$((Xaa^+-Xaa^{neu})_x(Xaa^--Xaa^{neu})_y)_n \quad (III)$$

$$((Xaa^--Xaa_{neu})_x((Xaa^+-Xaa^{neu})_y)_n \quad (IV)$$

Xaa$^{neu}$ represents an amino acid residue having a neutral charge; Xaa$^+$ represents an amino acid residue having a positive charge; Xaa$^-$ represents an amino acid residue having a negative charge; x and y are integers having a value of 1, 2, 3, or 4, independently; and n is an integer having a value of 1-5. Peptides with modulus I (i.e., peptides having alternate positively and negatively charged R groups on one side (e.g., the polar face of the β-sheet) are described by each of Formulas I-IV, where x and y are 1. Peptides of modulus II (i.e., peptides having two residues bearing one type of charge (e.g., a positive charge) followed by two residues bearing another type of charge (e.g., a negative charge)) are described by the same formulas where both x and y are 2. Examples of peptides of modulus III (i.e. peptides having three residues bearing one type of charge (e.g., a positive charge) followed by three residues bearing another type of charge (e.g., a negative charge)) include, but are not limited to, RARARADADADA (SEQ ID NO: 118).

Other hydrophilic residues that form hydrogen bonds including, but not limited to, asparagine and glutamine, may be incorporated into the peptides. If the alanine residues in the peptides are changed to more hydrophobic residues, such as leucine, isoleucine, phenylalanine or tyrosine, the resulting peptides have a greater tendency to self-assemble and form peptide matrices with enhanced strength. Some peptides that have similar amino acids compositions and lengths as the peptides described here form alpha-helices and random-coils rather than beta-sheets and do not form macroscopic structures. Thus, in addition to self-complementarity, other factors are likely to be important for the formation of macroscopic structures, such as the peptide length, the degree of intermolecular interaction, and the ability to form staggered arrays.

Peptide-based structures can be formed of heterogeneous mixtures of peptides (i.e., mixtures containing more than one type of peptide conforming to a given formula or to two or more of the formulas). In some embodiments, each of the types of peptides in the mixture is able to self-assemble alone. In other embodiments, one or more of each type of peptide would not, alone, self-assemble but the combination of heterogeneous peptides may self-assemble (i.e., peptides in the mixture are complementary and structurally compatible with each other). Thus, either a homogeneous mixture of self-complementary and self-compatible peptides of the same sequence or containing the same repeating subunit, or a heterogeneous mixture of different peptides which are complementary and structurally compatible to each other, can be used.

The compositions described herein regardless of the precise form (e.g., whether in a liquid form or molded) and regardless of the overall compositions (e.g., whether combined with another agent, contained within a device, or packaged in a kit) can include a mixture of one or more peptide chains.

Self-assembled structures can be formed that have varying degrees of stiffness or elasticity. The structures typically have a low elastic modulus (e.g., a modulus in the range of 0.01-1000 kPa, preferably from 1-10 kPa as measured by standard methods, such as in a standard cone-plate rheometer). Low values may be preferable, as they permit structure deformation as a result of movement, in response to pressure, in the event of cell contraction. More specifically, stiffness can be controlled in a variety of ways, including by changing the length, sequence, and/or concentration of the precursor molecules (e.g., self-assembling peptides). Other methods for increasing stiffness can also be employed. For example, one can attach, to the precursors, biotin molecules or any other molecules that can be subsequently cross-linked or otherwise bonded to one another. The molecules (e.g., biotin) can be included at an N- or C-terminus of a peptide or attached to one or more residues between the termini. Where biotin is used, cross-linking can be achieved by subsequent addition of avidin. Biotin-containing peptides or peptides containing other cross-linkable molecules are representative of cross-linkable peptides. For example, amino acid residues with polymerizable groups, such as vinyl groups may be incorporated and cross-linked by exposure to UV light. The extent of crosslinking can be precisely controlled by applying the radiation for a predetermined length of time to peptides of known sequence and concentration. The extent of crosslinking can be determined by light scattering, gel filtration, or scanning electron microscopy using standard methods. Furthermore, crosslinking can be examined by HPLC or mass spectrometry analysis of the structure after digestion with a protease, such as matrix metalloproteases. Material strength may be determined before and after cross-linking. Regardless of whether cross-linking is achieved by a chemical agent or light energy, the molecules may be cross-linked in the course of creating a mold or when peptide-containing solutions are applied to the body. Further, self-assembling peptide chains can be crosslinked to form a spider web-type pattern to reinforce the material in vivo. The crosslinks serve to reinforce the material providing increased rigidity and strength. For example, the self-assembling material can be applied to a wound, wherein the periphery of the material is functionalized with polymerizable groups. Upon crosslinking, the periphery of the material becomes more rigid, anchoring the material to the wound site, while the interior of material remains flexible to move as the body moves.

The half-life (e.g., the in vivo half-life) of the structures can also be modulated by incorporating protease or peptidase cleavage sites into the precursors that subsequently form a given structure. Proteases or peptidases that occur naturally in vivo or that are introduced (e.g., by a surgeon) can then promote degradation by cleaving their cognate substrates. The half-life can also be modulated by crosslinking (e.g., polymerization) of the material via functional groups within the material. These functional groups may be groups typically found in peptides or additional functional groups added to the peptides. Introducing crosslinks into the material typically increases the degradation time and can provide different cleavage sites/bonds within the material.

1. Other Self-Assembling Peptides

Another embodiment provides self-assembling peptides having a segment of residues having a positive charge under physiological conditions joined to a segment of residues having a negative charge under physiological conditions. The segment of positively or negatively charged residues can include about 2 to about 50 amino acid residues, typically about 3 to about 30 residues, more typically about 10 to about 20 amino acid residues. In another embodiment, about half of the residues of the self-assembling peptide are positively charged and the other half of the self-assembling peptide has negatively charged amino acid residues. A combination of these peptides can self-assemble by matching the positive end of a first self-assembling peptide to the negative end of a second self-assembling peptide. The negative end of the first self-assembling peptide will match up or align with the positive end of the second self-assembling peptide. The self-assembling peptides will stack-up or aggregate based on opposite ends of the self-assembling peptides being attacked based on charge at physiological compositions. One representative embodiment provides a self-assembling peptide having the following sequence RRRR-DDDD (SEQ ID NO: 119) or GGGG-SSSS (SEQ ID NO: 120).

In still another embodiment, the self-assembling peptide has a first hydrophobic region operably linked to a first hydrophilic region. The first hydrophobic region can include a segment of amino acid residues that have hydrophobic side chains under physiological conditions. The first hydrophilic region can include a segment of amino acid residues that have hydrophilic side chains under physiological conditions. In this embodiment, the hydrophobic ends of the self-assembling peptides would aggregate with other hydrophobic ends and the hydrophilic ends would aggregate with other hydrophilic ends. Aggregation can be controlled by altering the environment of the peptides. Such materials could be used to coat the inside of a lumen. The hydrophobic ends would likely interact with the ECM of the lumen surface sealing the surface while the hydrophilic ends extend out towards the center of the lumen. Fluids would continue to flow through the lumen. As the material degrades and/or is removed from the lumen surface, material would flow in from other areas and again anchor to the lumen surface, thus the composition acts a reservoir providing new material as needed. Alternatively, additional material could be administered to replace material that has worn or been degraded. In another embodiment, the material can be used as dynamic patches, for example, in the treatment of ulcers or for use in the intestine.

Another embodiment provides a self-assembling peptide that contains a segment of residues that have either a positive or negative charge under physiological conditions. Representative amino acid sequences for positively charged self-assembling peptides include, but are not limited to, KKKK (SEQ ID NO: 121), RRRR (SEQ ID NO: 122), or HHHH (SEQ ID NO: 123). Representative amino acid sequences for negatively charged self-assembling peptides include, but are not limited to, DDDD (SEQ ID NO: 124) or EEEE (SEQ ID NO: 125). When combined, a string of positively charged amino acid residues will align parallel and opposite with a string of negatively charged amino acid residues. In certain embodiments, strings of positively charged amino acids will alternate with strings of negatively charged amino acids to for a multilayered structure.

Still another embodiment provides self-assembling peptides that have a combination of hydrophilic polar amino acid residues and hydrophobic non-polar amino acid residues under physiological conditions. The one or more hydrophilic residues can alternate with one or more hydrophobic residues. For example, the amino acid sequence of a representative self-assembling peptide can be GQGQ (SEQ ID NO: 1), GGQQGG (SEQ ID NO: 2), GQQGQQG (SEQ ID NO: 3), GGQGGQGG (SEQ ID NO: 4), etc. It will be appreciated that the partitioning of the self-assembling peptide into a polar or non-polar environment can be controlled by altering the ratio of hydrophobic amino acid residues to hydrophilic amino acid residues, wherein a ratio greater than 1:1 indicates that the peptide partitions more in hydrophobic conditions compared to hydrophilic conditions. A ratio of less than 1:1 indicates that the peptide partitions more in hydrophilic conditions compared to hydrophobic conditions.

Combinations of any of the modifications described here can be made. For example, self-assembling peptides that include a protease cleavage site and a cysteine residue and/or a cross-linking agent, kits and devices containing them, and methods of using them can be utilized. The compositions can be used to prevent or limit movement of a bodily fluid, to stabilize tissue or cells, or to prevent contamination when administered to a site in need thereof. The compositions can be in the form of a dry powder, a wafer, a disk, a tablet, a capsule, a liquid, a gel, a cream, a foam, an ointment, an emulsion, a coating on a stent, catheter or other medical implant, the peptides incorporated into a microparticle, a polymeric matrix, a hydrogel, a fabric, a bandages, a suture, or a sponge.

B. Non-Peptide Materials which Self-Assemble

1. Peptidomimetics and Oligomers Having Backbone Which can Adopt Helical or Sheet Confirmations Another class of materials that can self assemble are peptidomimetics. Peptidomimetics, as used herein, refers to molecules which mimic peptide structures. Peptidomimetics have general features analogous to their parent structures, polypeptides, such as amphiphilicity. Examples of such peptidomimetic materials are described in Moore et al., *Chem. Rev.* 101(12), 3893-4012 (2001). The peptidomimetic materials can be classified into five categories: α-peptides, β-peptides, γ-peptides, δ-peptides, and oligomers having backbones which can adopt helical or sheet conformations. Copolymers of these peptides can also be used.

Examples of α-peptide peptidomimetics include, but are not limited to, N,N'-linked oligoureas, oligopyrrolinones, oxazolidin-2-ones, azatides and azapeptides.

Examples of β-peptides include, but are not limited to, peptide foldamers, aminoxy acids, sulfur-containing peptide analogues, and hydrazino peptides.

Examples of γ-peptides include, but are not limited to, peptide foldamers, oligoureas, oligocarbamates, and phosphodiesters.

Examples of δ-peptides include, but are not limited to, alkene-based amino acids and carbopeptoids, such as pyranose-based carbopeptoids and furanose-based carbopeptoids.

Another class of compounds includes oligomers having backbones which can adopt helical or sheet conformations. Example of such compounds include, but are not limited to, compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination.

Examples of compounds containing backbones utilizing bipyridine segments include, but are not limited to, oligo (pyridine-pyrimidines), oligo(pyridine-pyrimidines) with hydrazal linkers, and pyridine-pyridazines.

Examples of compounds containing backbones utilizing solvophobic interactions include, but are not limited to, oligoguanidines, aedamers (structures which take advantage of the stacking properties of aromatic electron donor-acceptor interactions of covalently linked subunits) such as oligomers containing 1,4,5,8-naphthalene-tetracarboxylic diimide rings and 1,5-dialkoxynaphthalene rings, and cyclophanes such as substituted N-benzyl phenylpyridinium cyclophanes.

Examples of compounds containing backbones utilizing side chain interactions include, but are not limited to, oligothiophenes such as oligothiophenes with chiral p-phenyloxazoline side chains, and oligo(m-phenylene-ethynylene)s.

Examples of compounds containing backbones utilizing hydrogen bonding interactions include, but are not limited to, aromatic amide backbones such as oligo(acylated 2,2'-bipyridine-3,3'-diamine)s and oligo(2,5-bis[2-aminophenyl] pyrazine)s, diaminopyridine backbones templated by cyanurate, and phenylene-pyridine-pyrimidine ethynylene backbones templated by isophthalic acid.

Examples of compounds containing backbones utilizing metal coordination include, but are not limited to, zinc bilinones, oligopyridines complexed with Co(II), Co(III), Cu(II), Ni(II), Pd(II), Cr(III), or Y(III), oligo(m-phenylene ethynylene)s containing metal-coordinating cyano groups, and hexapyrrins.

2. Nucleotidomimetics

Another class of molecules which can self assemble are nucleotidomimetics. Examples of nucleotidomimetics include, but are not limited to, isomeric oligonucleotides, modified carbohydrates, nucleotides with modified nucleotide linkages, and nucleotides with alternative nucleobases.

Examples of isomeric nucleotides include, but are not limited to, iso-RNA, iso-DNA, α-DNA (change in the anomeric configuration from β to α), alt-DNA, and 1-DNA.

Examples of modified carbohydrates include, but are not limited to, backbones with C1'-bases connectivities such as tetrofuranosyl oligonucleotides, pentopyranosyl oligonucleotides, and hexopyranosyl oligonucleotides; backbones with C2'-base connectivities such as isonucleotides (repositioning of the base sugar connection from C1 to the C2 position), HNAs (insertion of an additional methylene group between the O4' and C1' position of a furanose), ANAs (incorporation of a C3'-(S)-hydroxyl group), MAs (inversion of the C3'-OH configuration from (S) in ANAs to (R)), CNAs (replacement of the O of the hexose with a methylene group), CeNAs (introduction of a 5'-6' alkene within the analogous ring), as well as other ring systems, torsionally restricted oligonucleotides such as bicyclic oligonucleotides, LNAs (restriction of the pentofuranose backbone to the 3'-endo configuration), torsionally flexible oligonucleotides such as base sugar extensions (insertion of methylene and ethylene groups into both α- and β-deoxynucleotides) and acyclic backbones (glycerol derivatives incorporating phosphodiester linkages).

Examples of nucleotides with modified nucleotide linkages include, but are not limited to, PNAs (peptide nucleic acids), NDPs (nucleo-δ-peptides), fused sugar-base backbones, and cationic linkages.

Examples of alternative nucleobases include, but are not limited to, nucleotides with alternative aromatic nucleobases.

3. Other Materials

Other materials which can self assemble include N-alkylacrylamide oligomers and di- and tri-block co-polymers. N-alkylacrylamides can assume self-assembled sheet-like structures (see Kendhale et al., *Chem Comm*. (*Camb*), 26:2756-2758 (2006)). Examples of block copolymers include copolypeptides, polypeptide-PEGs, PEO-polybutadienes, PEG-polysaccharides, etc.

The structures formed from any self-assembling materials made by any process can be characterized using various biophysical and optical techniques, such as circular dichroism (CD), dynamic light scattering, Fourier transform infrared (FTIR), atomic force (tension) microscopy (ATM), scanning electron microscopy (SEM), and transmission electron microscopy (TEM). For example, biophysical methods can be used to determine the degree of beta-sheet secondary structure in a peptide or peptidomimetic structure. Filament and pore size, fiber diameter, length, elasticity, and volume fraction can be determined using quantitative image analysis of scanning and/or transmission electron micrographs. The structures can also be examined using several standard mechanical testing techniques to measure the extent of swelling, the effect of pH and ion concentration on structure formation, the level of hydration under various conditions, the tensile strength, as well as the manner in which various characteristics change over the period of time required for the structures to form and degrade. These methods allow one of ordinary skill in the art to determine which of the various alternatives and peptides described herein are most suitable for use in the various methods, and allow optimization of the various processes.

C. Components Enhancing or Inducing Formation of Self-Assembling Peptide Materials Prior to self-assembly, the peptides may be contained in (e.g., dissolved in) a solution that is substantially free of ions (e.g., monovalent ions) or that contains a sufficiently low concentration of ions to prevent significant self-assembly (e.g., a concentration of ions less than 10, 5, 1, or 0.1 mM). Self-assembly may be initiated or enhanced at any subsequent time by the addition of an ionic solute or diluent to a peptide solution or by a change in pH. For example, NaCl at a concentration of between approximately 5 mM and 5 M will induce the assembly of macroscopic structures within a short period of time (e.g., within a few minutes). Lower concentrations of NaCl may also induce assembly but at a slower rate. Alternatively, self-assembly may be initiated or enhanced by introducing the peptides (whether dry, in a semi-solid gel, or dissolved in a liquid solution that is substantially free of ions) into a fluid (e.g., a physiological fluid such as blood or gastric juice) or an area (e.g., a body cavity such as the nose or mouth or a cavity exposed by a surgical procedure, injury, trauma, disease, or disorder) comprising such ions. Generally, self-assembly is expected to occur upon contacting the peptides with such a solution in any manner. Assembly time may be decreased in order to allow the material to intermingle with the underlying tissue or vessel before the material assembles.

A wide variety of ions, including anions and cations (whether divalent, monovalent, or trivalent), can be used. For example, one can promote a phase transition by exposure to monovalent cations such as $Li^+$, $Na^+$, $K^+$, and $Cs^+$, and the concentration of such ions required to induce or enhance self-assembly is typically at least about 5 mM, preferably at least about 10 mM, more preferably at least about 20 mM, and most preferably about 50 mM. Lower concentrations may also facilitate assembly, though at a slower rate. When desired, self-assembling peptides can be delivered with a hydrophobic material (e.g. pharmaceutically acceptable oil) in a concentration that permits self-assembly, but at a slower rate. When self-assembling peptides are mixed with a hydrophobic agent such as an oil or lipid the assembly of the material forms different structures. The structures typically appear like ice on a layer of oil but in some cases when another material is added, the material will assemble into various other three dimensional structures that may be suitable for drug loading/delivery. The hydrophilic part of the molecule will assemble in such a way to minimize hydrophobic-hydrophilic interaction, thereby creating a barrier between the two environments. Several experiments have shown that the self-assembling peptides will align on the surface of the oil like ice on water with the hydrophobic part of the molecule toward the surface and the hydrophilic portion of the molecule facing away from the oil, or will form toroidal-like structures with the hydrophobic material contained inside. This type of behavior enables the encapsulation of therapeutics or other molecules of interested for delivery in the body.

Depending on the formulation and desired properties of the macroscopic structure (e.g., the stiffness of the scaffold or the rate of its formation), the concentration of precursors (e.g., self-assembling peptides) can vary from approximately 0.01% w/v (0.1 mg/ml) to approximately 99.99% w/v (999.9 mg/ml), inclusive. For example, the concentration prior to scaffold formation can be between approximately 0.1% (1 mg/ml) and 10% (100 mg/ml), inclusive (e.g., about 0.1%-5%; 0.5%-5%; 1.0%; 1.5%; 2.0%; 2.5%; 3.0%; or 4.0% or more). In some embodiments, the concentration may be less than 0.1%. The precursors (e.g., self-assembling peptides) can be formulated as powders and administered in a powder form or resuspended. If dry, the peptides can then self-assemble following contact with bodily fluids (e.g., at a site of injury). In one embodiment, the concentration of the self-assembling peptides in any given formulation can vary and can be between approximately 0.1% (1 mg/ml) and 10% (100 mg/ml), inclusive. For example, the concentration of the self-assembling peptides (e.g., in a liquid formulation) can be approximately 0.1-3.0% (1-30 mg/ml) (e.g., 0.1-1.0%; 1.0-2.0%; 2.0-3.0% or 1.0-3.0%). The concentration of self-assembling peptides can be higher in stock solutions and in solid (e.g., powdered) formulations. In solid preparations, the concentration of self-assembling peptides can approach 100% (e.g., the concentration of self-assembling peptides can be 95, 96, 97, 98, 99% or more (e.g., 99.99%) of the composition). Whether in liquid or solid form, the peptides can be brought to the desired concentration prior to use by addition of a diluent (e.g., deionized water), powder, wetting agent, or a therapeutic, diagnostic or prophylactic agent.

Peptide-based structures can be formed within regularly or irregularly-shaped molds, which may include a body cavity or a portion of the body (e.g., the lumen of a blood vessel) or which may be an inert material, including but not limited to, plastic or glass. The structures or scaffolds can be made to conform to a predetermined shape or to have a predetermined volume. To form a structure with a predetermined shape or volume (e.g., a desired geometry or dimension, including thin sheets or films), an aqueous peptide solution is placed in a pre-shaped casting mold, and the peptides are induced to self-assemble by the addition of a plurality of ions. Alternatively, the ions may be added to the peptide solution shortly before placing the solution into the mold, provided that care is taken to place the solution into the mold before substantial assembly occurs. Where the mold is a tissue (e.g., the lumen of a blood vessel or other compartment, whether in situ or not), the addition of an ionic solution may not be necessary. The resulting material characteristics, the time required for assembly, and the dimensions of the macroscopic structure that forms are governed by the concentration and amount of peptide solution that is applied, the concentration of ions used to induce assembly of the structure, and the dimensions of the casting apparatus. The scaffold can achieve a gel-like or substantially solid form at room temperature, and heat may be applied to facilitate the molding (e.g., one can heat a solution used in the molding process (e.g., a precursor-containing solution) to a temperature ranging up to about body temperature (approximately 37° C.)). Once the scaffold has reached the desired degree of firmness, it can be removed from the mold and used for a purpose described herein. The scaffold may be used to induce regeneration of tissues such as CNS (central nervous system), vessels, kidney, etc., The self-assembling material used for making scaffold for different tissues mimic the environment of the developing tissues and therefore can be different for each tissue.

Materials that assemble and/or undergo a phase transition (e.g., a transition from a liquid state to a semi-solid, gel, etc.) when they come in contact with the body are useful in preventing the movement of bodily substances. In the case of skin, the compositions may be administered with an ionic solution or oil in order to self assemble, in the absence of moisture or oil on the skim Self-assembly or phase transition is triggered by components found in a subject's body (e.g., ions) or by physiological pH and is assisted by physiological temperatures. Self-assembly or phase transition can begin when the compositions are exposed to or brought into contact with a subject's body and may be facilitated by the local application of heat to the area where the composition has been (or will be) deposited. The subject, for any indication described herein, can be a human. Based on studies to date, self-assembly occurs rapidly upon contact with internal bodily tissues without the application of additional heat. In one embodiment, the time required for effective assembly and/or phase transition can be 60 seconds or less following contact with a subject's internal tissues or to conditions similar to those found within the body (e.g., in 50, 40, 30, 20, or 10 seconds or less). In some circumstances, such as where the concentration of self-assembling agents in the composition is low or where the movement of the bodily substance is substantial, self-assembly or phase transition may take longer to achieve the desired effect, for example, up to a minute, 5 minutes, 10 minutes, 30 minutes, an hour, or longer. For example, a solution containing a self-assembling peptide applied to sites of blood vessel trans-section in the brain, liver, or muscle provides complete hemostasis within times as short as 10 seconds following application. Ion-containing solutions may be preferred when the compositions are used to protect a subject from contamination, as phase transitions do not occur, or do not readily occur, when non-ionic compositions contact intact skin.

The compositions can form structures that are substantially rigid (e.g., solid or nearly solid) or that assume a definite shape and volume (e.g., structures that conform to the shape and volume of the location to which a liquid composition was administered, whether in vivo or ex vivo). The solidified material may be somewhat deformable or compressible after assembly or phase transition, but will not substantially flow from one area to another, as compositions at a different point along the liquid to solid continuum may do, which may be due, at least in part, to their ability to undergo phase transitions. As a result, the compositions can be used to prevent the movement of a bodily substance in a subject in need thereof. Self-assembly can be achieved in vivo or ex vivo by exposure to conditions within a certain range of physiological values (e.g., conditions appropriate for cell or tissue culture) or non-physiological conditions. "Non-physiological conditions" refers to conditions within the body or at a particular site that deviate from normal physiological conditions at that site. Such conditions may result from trauma, surgery, injury, infection, or a disease, disorder, or condition. For example, a puncture wound in the stomach generally results in a decrease in the pH as stomach acid flows into the wound site. The materials described herein should self assemble under such conditions. While liquid formulations are readily dispensed, the compositions administered may also be in a gel form that may become stiffer upon contact with the subject's body.

Regardless of the precise nature of the self-assembling agents, upon exposure to conditions such as those described herein, the agents can form membranous two- or three-dimensional structures including a stable macroscopic porous matrix having ordered or unordered interwoven nanofibers (e.g., fibers approximately 10-20 nm in diameter, with a pore size of about 50-100 nm or larger in a linear dimension). Three-dimensional macroscopic matrices can have dimensions large enough to be visible under low magnification (e.g., about 10-fold or less), and the membranous structures can be visible to the naked eye, even if transparent. Although three-dimensional, the structures can be exceedingly thin, including a limited number of layers of molecules (e.g., 2, 3, or more layers of molecules). Typically, each dimension of a given structure will be at least 10 µm in size (e.g., two dimensions of at least 100-1000 µm in size (e.g., 1-10 mm, 10-100 mm, or more)). The relevant dimensions may be expressed as length, width, depth, breadth, height, radius, diameter, or circumference in the case of structures that have a substantially regular shape (e.g., where the structure is a sphere, cylinder, cube, or the like) or an approximation of any of the foregoing where the structures do not have a regular shape.

The self-assembling peptides can form a hydrated material when contacted with water under conditions such as those described herein (e.g., in the presence of a sufficient concentration (e.g., physiological concentrations) of ions (e.g., monovalent cations)). The materials may have a high water content (e.g., approximately 95% or more (e.g., approximately 97%, 98%, 99% or more)), and the compositions can be hydrated but not substantially self-assembled. A given value may be "approximate" in recognition of the fact that measurements can vary depending, for example, on the circumstances under which they are made and the skill of the person taking the measurement. Generally, a first value is approximately equal to a second when the first falls within 10% of the second (whether greater than or less than) unless it is otherwise clear from the context that a value is not approximate or where, for example, such value would exceed 100% of a possible value.

The properties and mechanical strength of the structures or scaffolds can be controlled as required through manipulation of the components therein. For example, the stiffness of an assembled gel can be increased by increasing the concentration of self-assembling agents (e.g., peptides) therein. Alternatively, it may be desirable for different parts of the material to have different mechanical properties. For example, it may be advantageous to decrease the stability of all or part of the material by manipulating the amino acid sequence. This may be desirable when the materials are used to fill a void, such that the edges of the material self-assemble to attach to the tissue site while the rest of the material flows out into the void.

The sequences, characteristics, and properties of the peptides and the structures formed by them upon self-assembly are discussed further below.

The compositions can be formulated as concentrated stocks or in dry form, and these can be diluted or dissolved to form compositions (e.g., biocompatible compositions), which are substantially non-toxic to biological cells in vitro or in vivo. For example, the compositions can contain materials in quantities that do not elicit a significant deleterious effect on the recipient's body (e.g., a prohibitively severe immunological or inflammatory reaction, or unacceptable scar tissue formation).

When a solution containing non-assembled peptides is laid down on a biological tissue, the peptides having sufficient proximity to the tissue assemble, causing the solution to gel. Any solution that remains distant from the tissue remains liquid, as the self-assembling peptides have not yet been exposed to conditions that promote their assembly. As the material is disturbed (e.g., by performing a surgical procedure), liquid material appears to gel as it comes into sufficient contact with the body. At times, the compositions can take on characteristics ranging from a liquid to those of a solid, appearing gel- or salve-like or as a slurry).

D. Modification of Self-Assembling Materials to Target Specific Tissues.

The self-assembling peptides can be modified to include a targeting agent.

Referring to FIG. 1, the self assembling material may further contain a tissue specific component to direct the self-assembling peptide to a specific location, cell, tissue, organ, or organelle. Representative targeting agents include, but are not limited to, nuclear localization signals, mitochondria localization signals, antibodies or antigen binding antibody fragments, single chain antibodies, sugar moieties, lipids, glycolipids, dyes, and glycoproteins. The targeting agents can be attached to the self-assembling peptides directly or through a linker. In some embodiments, the targeting agent is releasably attached to the self-assembling peptide for example through a cleavable bond or enzyme cleavage site. For example, cell surface carbohydrates are major components of the outer surface of mammalian cells and are very often characteristic of cell types. It is assumed that cell type-specific carbohydrates are involved in cell-cell interaction. The tissue specific component can therefore, target these cell specific surface carbohydrates. The targeting may be useful for specific locations in the body when the compositions are injected, Additionally, hydrophobic tails can be added to the self assembling material. Hydrophobic tails can interact with cell membrane, thus anchoring the self assembling material on to the cell surface. Table 3 shows a list of peptides with hydrophobic tails. Hydrophilic tails can also be added to the peptide, alone or in addition to hydrophobic tails, to facilitate interaction with the ECM of different vessels or tissues, such as the bladder.

TABLE 3

Hydrophobic Tails

| | |
|---|---|
| 1  G G G G D G D G D G D G D | (SEQ ID NO: 126) |
| 2  G G G G E G E G E G E G E | (SEQ ID NO: 127) |
| 3  G G G G K G K G K G K G K | (SEQ ID NO: 128) |
| 4  G G G G R G R G R G R G R | (SEQ ID NO: 129) |
| 5  G G G G H G H G H G H G H | (SEQ ID NO: 130) |
| 6  A A A A D A D A D A D A D | (SEQ ID NO: 131) |
| 7  A A A A E A E A E A E A E | (SEQ ID NO: 132) |
| 8  A A A A K A K A K A K A K | (SEQ ID NO: 133) |
| 9  A A A A R A R A R A R A R | (SEQ ID NO: 134) |
| 10 A A A A H A H A H A H A H | (SEQ ID NO: 135) |
| 11 V V V V D V D V D V D V D | (SEQ ID NO: 136) |
| 12 V V V V E V E V E V E V E | (SEQ ID NO: 137) |
| 13 V V V V K V K V K V K V K | (SEQ ID NO: 138) |
| 14 V V V V R V R V R V R V R | (SEQ ID NO: 139) |
| 15 V V V V H V H V H V H V H | (SEQ ID NO: 140) |
| 16 L L L L D L D L D L D L D | (SEQ ID NO: 141) |
| 17 L L L L E L E L E L E L E | (SEQ ID NO: 142) |
| 18 L L L L K L K L K L K L K | (SEQ ID NO: 143) |
| 19 L L L L R L R L R L R L R | (SEQ ID NO: 144) |
| 20 L L L L H L H L H L H L H | (SEQ ID NO: 145) |
| 21 I I I I D I D I D I D I D | (SEQ ID NO: 146) |
| 22 I I I I E I E I E I E I E | (SEQ ID NO: 147) |
| 23 I I I I K I K I K I K I K | (SEQ ID NO: 148) |
| 24 I I I I R I R I R I R I R | (SEQ ID NO: 149) |
| 25 I I I I H I H I H I H I H | (SEQ ID NO: 150) |
| 26 M M M M D M D M D M D M D | (SEQ ID NO: 151) |
| 27 M M M M E M E M E M E M E | (SEQ ID NO: 152) |
| 28 M M M M K M K M K M K M K | (SEQ ID NO: 153) |
| 29 M M M M R M R M R M R M R | (SEQ ID NO: 154) |
| 30 M M M M H M H M H M H M H | (SEQ ID NO: 155) |
| 31 F F F F D F D F D F D F D | (SEQ ID NO: 156) |
| 32 F F F F E F E F E F E F E | (SEQ ID NO: 157) |
| 33 F F F F K F K F K F K F K | (SEQ ID NO: 158) |
| 34 F F F F R F R F R F R F R | (SEQ ID NO: 159) |
| 35 F F F F H F H F H F H F H | (SEQ ID NO: 160) |

TABLE 3-continued

Hydrophobic Tails

```
 36 W W W W W D W D W D W D W D (SEQ ID NO: 161)
 37 W W W W E W E W E W E W E W E (SEQ ID NO: 162)
 38 W W W W W K W K W K W K W K (SEQ ID NO: 163)
 39 W W W W W R W R W R W R W R (SEQ ID NO: 164)
 40 W W W W W H W H W H W H W H (SEQ ID NO: 165)
 41 P P P P P D P D P D P D P D (SEQ ID NO: 166)
 42 P P P P P E P E P E P E P E (SEQ ID NO: 167)
 43 P P P P P K P K P K P K P K (SEQ ID NO: 168)
 44 P P P P P R P R P R P R P R (SEQ ID NO: 169)
 45 P P P P P H P H P H P H P H (SEQ ID NO: 170)
 46 A A A A A R A D A R A D A R A D (SEQ ID NO: 171)
 47 A A A A A R A R A D A D A R A R (SEQ ID NO: 172)
 48 A A A A A E A K A E A K A E A K (SEQ ID NO: 173)
 49 A A A A A E A E A K A K A E A E (SEQ ID NO: 174)
 50 A A A A A R A E A R A E A R A E (SEQ ID NO: 175)
 51 A A A A A R A E A E A R A E (SEQ ID NO: 176)
 52 A A A A A K A D A K A D A K A D (SEQ ID NO: 177)
 53 A A A A A E A H A E A H A E A H (SEQ ID NO: 178)
 54 A A A A A E A E A H A H A E A E (SEQ ID NO: 179)
 55 A A A A A R A R A R A R A R (SEQ ID NO: 180)
 56 A A A A A R A R A R A R A D A D (SEQ ID NO: 181)
 57 A A A A A R A R A R A D A D A D (SEQ ID NO: 182)
 58 A A A A A H A D A H A D A H A D (SEQ ID NO: 183)
 59 A A A A A H A H A H A H A H A H (SEQ ID NO: 184)
 60 A A A A A H A D A D A H A D (SEQ ID NO: 185)
 61 A A A A A H A E A E A H A E A E (SEQ ID NO: 186)
 62 G G G G G R G D G R G D G R G D (SEQ ID NO: 187)
 63 G G G G G R G R G D G D G R G R (SEQ ID NO: 188)
 64 G G G G G E G K G E G K G E G K (SEQ ID NO: 189)
 65 G G G G G E G E G K G K G E G E (SEQ ID NO: 190)
 66 G G G G G R G E G R G E G R G E (SEQ ID NO: 191)
 67 G G G G G R G R G E G E G R G E (SEQ ID NO: 192)
 68 G G G G G K G D G K G D G K G D (SEQ ID NO: 193)
 69 G G G G G E G H G E G H G E G H (SEQ ID NO: 194)
 70 G G G G G E G E G H G H G E G E (SEQ ID NO: 195)
 71 G G G G G R G R G R G R G R (SEQ ID NO: 196)
 72 G G G G G R G R G R G R G D G D (SEQ ID NO: 197)
 73 G G G G G R G R G R G D G D G D (SEQ ID NO: 198)
 74 G G G G G H G D G H G D G H G D (SEQ ID NO: 199)
 75 G G G G G H G H G H G H G H (SEQ ID NO: 200)
 76 G G G G H G D G H G D G H G D G D (SEQ ID NO: 201)
 77 G G G G H G E G E G H G E G E (SEQ ID NO: 202)
 78 V V V V R V D V R V D V R V D (SEQ ID NO: 203)
 79 V V V V R V R V D V D V R V R (SEQ ID NO: 204)
 80 V V V V E V K V E V K V E V K (SEQ ID NO: 205)
 81 V V V V E V E V K V K V E V E (SEQ ID NO: 206)
 82 V V V V R V E V R V E V R V E (SEQ ID NO: 207)
 83 V V V V R V R V E V E V P V E (SEQ ID NO: 208)
 84 V V V V K V D V K V D V K V D (SEQ ID NO: 209)
 85 V V V V E V H V E V H V E V H (SEQ ID NO: 210)
 86 V V V V E V E V H V H V E V E (SEQ ID NO: 211)
 87 V V V V R V R V R V P V R V R (SEQ ID NO: 212)
 88 V V V V R V R V R V R V D V D (SEQ ID NO: 213)
 89 V V V V R V R V R V D V D V D (SEQ ID NO: 214)
 90 V V V V H V D V H V D V H V D (SEQ ID NO: 215)
 91 V V V V H V H V H V H V H V H (SEQ ID NO: 216)
 92 V V V V H V D V D V H V D V D (SEQ ID NO: 217)
 93 V V V V H V E V E V H V E V E (SEQ ID NO: 218)
 94 L L L L R L D L R L D L R L D (SEQ ID NO: 219
 95 L L L L R L R L D L D L R L R (SEQ ID NO: 220)
 96 L L L L E L K L E L K L E L K (SEQ ID NO: 221)
 97 L L L L E L E L K L K L E L E (SEQ ID NO: 222)
 98 L L L L R L E L R L E L R L E (SEQ ID NO: 223)
 99 L L L L R L R L E L E L R L E (SEQ ID NO: 224)
100 L L L L K L D L K L D L K L D (SEQ ID NO: 225)
101 L L L L E L H L E L H L E L H (SEQ ID NO: 226)
102 L L L L E L E L H L H L E L E (SEQ ID NO: 227)
103 L L L L R L R L R L R L R L R (SEQ ID NO: 228)
104 L L L L R L R L R L R L D L D (SEQ ID NO: 229)
105 L L L L R L R L R L D L D L D (SEQ ID NO: 230)
106 L L L L H L D L H L D L H L D (SEQ ID NO: 231)
107 L L L L H L H L H L H L H L H (SEQ ID NO: 232)
108 L L L L H L D L D L H L D L D (SEQ ID NO: 233)
109 L L L L H L E L E L H L E L E (SEQ ID NO: 234)
110 I I I I R I D I R I D I R I D (SEQ ID NO: 235)
111 I I I I R I R I D I D I R I R (SEQ ID NO: 236)
112 I I I I E I K I E I K I E I K (SEQ ID NO: 237)
113 I I I I E I E I K I K I E I E (SEQ ID NO: 238)
```

TABLE 3-continued

Hydrophobic Tails

114 I I I I I R I E I R I E I R I E (SEQ ID NO: 239)
115 I I I I I R I R I E I E I R I E (SEQ ID NO: 240)
116 I I I I I K I D I K I D I K I D (SEQ ID NO: 241)
117 I I I I I E I H I E I H I E I H (SEQ ID NO: 242)
118 I I I I I E I E I H I H I E I E (SEQ ID NO: 243)
119 I I I I I R I R I R I R I R I R (SEQ ID NO: 244)
120 I I I I I R I R I R I R I D I D (SEQ ID NO: 245)
121 I I I I I R I R I R I D I D I D (SEQ ID NO: 246)
122 I I I I I H I D I H I D I H I D (SEQ ID NO: 247)
123 I I I I I H I H I H I H I H I H (SEQ ID NO: 248)
124 I I I I I H I D I D I H I D I D (SEQ ID NO: 249)
125 I I I I I H I E I E I H I E I E (SEQ ID NO: 250)
126 M M M M M R M D M R M D M R M D (SEQ ID NO: 251)
127 M M M M M R M R M D M D M R M R (SEQ ID NO: 252)
128 M M M M M E M K M E M K M E M K (SEQ ID NO: 253)
129 M M M M M E M E M K M K M E M E (SEQ ID NO: 254)
130 M M M M M R M E M R M E M R M E (SEQ ID NO: 255)
131 M M M M M R M R M E M E M R M E (SEQ ID NO: 256)
132 M M M M M K M D M K M D M K M D (SEQ ID NO: 257)
133 M M M M M E M H M E M H M E M H (SEQ ID NO: 258)
134 M M M M M E M E M H M H M E M E (SEQ ID NO: 259)
135 M M M M M R M R M R M R M R M R (SEQ ID NO: 260)
136 M M M M M R M R M R M R M D M D (SEQ ID NO: 261)
137 M M M M M R M R M R M D M D M D (SEQ ID NO: 262)
138 M M M M M H M D M H M D M H M D (SEQ ID NO: 263)
139 M M M M M H M H M H M H M H M H (SEQ ID NO: 264)
140 M M M M M H M D M D M H M D M D (SEQ ID NO: 265)
141 M M M M M H M E M E M H M E M E (SEQ ID NO: 266)
142 F F F F F R F D F R F D F R F D (SEQ ID NO: 267)
143 F F F F F R F R F D F D F R F R (SEQ ID NO: 268)
144 F F F F F E F K F E F K F E F K (SEQ ID NO: 269)
145 F F F F F E F E F K F K F E F E (SEQ ID NO: 270)
146 F F F F F R F E F R F E F R F E (SEQ ID NO: 271)
147 F F F F F R F R F E F E F R F E (SEQ ID NO: 272)
148 F F F F F K F D F K F D F K F D (SEQ ID NO: 273)
149 F F F F F E F H F E F H F E F H (SEQ ID NO: 274)
150 F F F F F E F E F H F H F E F E (SEQ ID NO: 275)
151 F F F F F R F R F R F R F R F R (SEQ ID NO: 276)
152 F F F F F R F R F R F R F D F D (SEQ ID NO: 277)
153 F F F F F R F R F R F D F D F D (SEQ ID NO: 278)
154 F F F F F H F D F H F D F H F D (SEQ ID NO: 279)
155 F F F F F H F H F H F H F H F H (SEQ ID NO: 280)
156 F F F F F H F D F D F H F D F D (SEQ ID NO: 281)
157 F F F F F H F E F F F H F E F F (SEQ ID NO: 282)
158 W W W W W R W D W R W D W R W D (SEQ ID NO: 283)
159 W W W W W R W R W D W D W R W R (SEQ ID NO: 284)
160 W W W W W E W K W E W K W E W K (SEQ ID NO: 285)
161 W W W W W E W E W K W K W E W E (SEQ ID NO: 286)
162 W W W W W R W E W R W E W R W E (SEQ ID NO: 287)
163 W W W W W R W R W E W E W R W E (SEQ ID NO: 288)
164 W W W W W K W D W K W D W K W D (SEQ ID NO: 289)
165 W W W W W E W H W E W H W E W H (SEQ ID NO: 290)
166 W W W W W E W E W H W H W E W E (SEQ ID NO: 291)
167 W W W W W R W R W R W R W R W R (SEQ ID NO: 292)
168 W W W W W R W R W R W R W D W D (SEQ ID NO: 293)
169 W W W W W R W R W R W D W D W D (SEQ ID NO: 294)
170 W W W W W H W D W H W D W H W D (SEQ ID NO: 295)
171 W W W W W H W H W H W H W H W H (SEQ ID NO: 296)
172 W W W W W H W D W D W H W D W D (SEQ ID NO: 297)
173 W W W W W H W E W E W H W E W E (SEQ ID NO: 298)
174 P P P P P R P D P R P D P R P D (SEQ ID NO: 299)
175 P P P P P R P R P D P D P R P R (SEQ ID NO: 300)
176 P P P P P E P K P E P K P E P K (SEQ ID NO: 301)
177 P P P P P E P E P K P K P E P E (SEQ ID NO: 302)
178 P P P P P R P E P R P E P R P E (SEQ ID NO: 303)
179 P P P P P R P R P E P E P R P E (SEQ ID NO: 304)
180 P P P P P K P D P K P D P K P D (SEQ ID NO: 305)
181 P P P P P E P H P E P H P E P H (SEQ ID NO: 306)
182 P P P P P E P E P H P H P E P E (SEQ ID NO: 307)
183 P P P P P R P R P R P R P R P R (SEQ ID NO: 308)
184 P P P P P R P R P R P R P D P D (SEQ ID NO: 309)
185 P P P P P R P R P R P D P D P D (SEQ ID NO: 310)
186 P P P P P H P D P H P D P H P D (SEQ ID NO: 311)
187 P P P P P H P H P H P H P H P H (SEQ ID NO: 312)
188 P P P P P H P D P D P H P D P D (SEQ ID NO: 313)
189 P P P P P H P E P E P H P E P E (SEQ ID NO: 314)
190 S S S S S R S D S R S D S R S D (SEQ ID NO: 315)
191 S S S S S R S R S D S D S R S R (SEQ ID NO: 316)

TABLE 3-continued

Hydrophobic Tails

192 S S S S S E S K S E S K S E S K (SEQ ID NO: 317)
193 S S S S S E S E S K S K S E S E (SEQ ID NO: 318)
194 S S S S S R S E S R S E S R S E (SEQ ID NO: 319)
195 S S S S S R S R S E S E S R S E (SEQ ID NO: 320)
196 S S S S S K S D S K S D S K S D (SEQ ID NO: 321)
197 S S S S S E S H S E S H S E S H (SEQ ID NO: 322)
198 S S S S S E S E S H S H S E S E (SEQ ID NO: 323)
199 S S S S S R S R S R S R S R S R (SEQ ID NO: 324)
200 S S S S S R S R S R S R S D S D (SEQ ID NO: 325)
201 S S S S S R S R S R S D S D S D (SEQ ID NO: 326)
202 S S S S S H S D S H S D S H S D (SEQ ID NO: 327)
203 S S S S S H S H S H S H S H S H (SEQ ID NO: 328)
204 S S S S S H S D S D S H S D S D (SEQ ID NO: 329)
205 S S S S S H S E S E S H S E S E (SEQ ID NO: 330)
206 T T T T T R T D T R T D T R T D (SEQ ID NO: 331)
207 T T T T T R T R T D T D T R T R (SEQ ID NO: 332)
208 T T T T T E T K T E T K T E T K (SEQ ID NO: 333)
209 T T T T T E T E T K T K T E T E (SEQ ID NO: 334)
210 T T T T T R T E T R T E T R T E (SEQ ID NO: 335)
211 T T T T T R T R T E T E T R T E (SEQ ID NO: 336)
212 T T T T T K T D T K T D T K T D (SEQ ID NO: 337)
213 T T T T T E T H T E T H T E T H (SEQ ID NO: 338)
214 T T T T T E T E T H T H T E T E (SEQ ID NO: 339)
215 T T T T T R T R T R T R T R T R (SEQ ID NO: 340)
216 T T T T T R T R T R T R T D T D (SEQ ID NO: 341)
217 T T T T T R T R T R T D T D T D (SEQ ID NO: 342)
218 T T T T T H T D T H T D T H T D (SEQ ID NO: 343)
219 T T T T T H T H T H T H T H T H (SEQ ID NO: 344)
220 T T T T T H T D T D T H T D T D (SEQ ID NO: 345)
221 T T T T T H T E T E T H T E T E (SEQ ID NO: 346)
222 C C C C C R C D C R C D C R C D (SEQ ID NO: 347)
223 C C C C C R C R C D C D C R C R (SEQ ID NO: 348)
224 C C C C C E C K C E C K C E C K (SEQ ID NO: 349)
225 C C C C C E C E C K C K C E C E (SEQ ID NO: 350)
226 C C C C C R C E C R C E C R C E (SEQ ID NO: 351)
227 C C C C C R C R C E C E C R C E (SEQ ID NO: 352)
228 C C C C C K C D C K C D C K C D (SEQ ID NO: 353)
229 C C C C C E C H C E C H C E C H (SEQ ID NO: 354)
230 C C C C C E C E C H C H C E C E (SEQ ID NO: 355)
231 C C C C C R C R C R C R C R C R (SEQ ID NO: 356)
232 C C C C C R C R C R C R C D C D (SEQ ID NO: 357)
233 C C C C C R C R C R C D C D C D (SEQ ID NO: 358)
234 C C C C C H C D C H C D C H C D (SEQ ID NO: 359)
235 C C C C C H C H C H C H C H C H (SEQ ID NO: 360)
236 C C C C C H C D C D C H C D C D (SEQ ID NO: 361)
237 C C C C C H C E C E C H C E C E (SEQ ID NO: 362)
238 Y Y Y Y R Y D Y R Y D Y R Y D (SEQ ID NO: 363)
239 Y Y Y Y R Y R Y D Y D Y R Y R (SEQ ID NO: 364)
240 Y Y Y Y E Y K Y E Y K Y E Y K (SEQ ID NO: 365)
241 Y Y Y Y E Y E Y K Y K Y E Y E (SEQ ID NO: 366)
242 Y Y Y Y R Y E Y R Y E Y R Y E (SEQ ID NO: 367)
243 Y Y Y Y R Y R Y E Y E Y R Y E (SEQ ID NO: 368)
244 Y Y Y Y K Y D Y K Y D Y K Y D (SEQ ID NO: 410)
245 Y Y Y Y E Y H Y E Y H Y E Y H (SEQ ID NO: 369)
246 Y Y Y Y E Y E Y H Y H Y E Y E (SEQ ID NO: 370)
247 Y Y Y Y R Y R Y R Y R Y R Y R (SEQ ID NO: 371)
248 Y Y Y Y R Y R Y R Y Y Y D Y D (SEQ ID NO: 372)
249 Y Y Y Y Y Y Y Y Y D Y D Y D (SEQ ID NO: 373)
250 Y Y Y Y H Y D Y H Y D Y H Y D (SEQ ID NO: 374)
251 Y Y Y Y H Y H Y H Y H Y H Y H (SEQ ID NO: 375)
252 Y Y Y Y H Y D Y D Y H Y D Y D (SEQ ID NO: 376)
253 Y Y Y Y H Y E Y E Y H Y E Y E (SEQ ID NO: 377)
254 N N N N R N D N R N D N R N D (SEQ ID NO: 378)
255 N N N N R N R N D N D N R N R (SEQ ID NO: 379)
256 N N N N E N K N E N K N E N K (SEQ ID NO: 380)
257 N N N N E N E N K N K N E N E (SEQ ID NO: 381)
258 N N N N N E N R N E N R N E (SEQ ID NO: 382)
259 N N N N R N R N E N E N R N E (SEQ ID NO: 383)
260 N N N N K N D N K N D N K N D (SEQ ID NO: 384)
261 N N N N E N H N E N H N E N H (SEQ ID NO: 385)
262 N N N N E N E N H N H N E N E (SEQ ID NO: 386)
263 N N N N R N R N R N R N R N R (SEQ ID NO: 387)
264 N N N N N R N N N R N D N D (SEQ ID NO: 388)
265 N N N N R N R N R N D N D N D (SEQ ID NO: 389)
266 N N N N H N D N H N D N H N D (SEQ ID NO: 390)
267 N N N N H N H N H N H N H N H (SEQ ID NO: 391)
268 N N N N H N D N D N H N D N D (SEQ ID NO: 392)
269 N N N N H N E N E N H N E N E (SEQ ID NO: 393)

TABLE 3-continued

Hydrophobic Tails

270 Q Q Q Q R Q D Q R Q D Q R Q D (SEQ ID NO: 394)

271 Q Q Q Q R Q R Q D Q D Q R Q R (SEQ ID NO: 395)

272 Q Q Q Q E Q K Q E Q K Q E Q K (SEQ ID NO: 396)

273 Q Q Q Q E Q E Q K Q K Q E Q E (SEQ ID NO: 397)

274 Q Q Q Q R Q E Q R Q E Q R Q E (SEQ ID NO: 398)

275 Q Q Q Q R Q R Q E Q E Q R Q E (SEQ ID NO: 399)

276 Q Q Q Q K Q D Q K Q D Q K Q D (SEQ ID NO: 400)

277 Q Q Q Q E Q H Q E Q H Q E Q H (SEQ ID NO: 401)

278 Q Q Q Q E Q E Q H Q H Q E Q E (SEQ ID NO: 402)

279 Q Q Q Q R Q R Q R Q R Q R Q R (SEQ ID NO: 403)

280 Q Q Q Q R Q R Q R Q R Q D Q D (SEQ ID NO: 404)

281 Q Q Q Q R Q R Q R Q D Q D Q D (SEQ ID NO: 405)

282 Q Q Q Q H Q D Q H Q D Q H Q D (SEQ ID NO: 406)

283 Q Q Q Q H Q H Q H Q H Q H Q H (SEQ ID NO: 407)

284 Q Q Q Q H Q D Q D Q H Q D Q D (SEQ ID NO: 408)

285 Q Q Q Q H Q E Q E Q H Q E Q E (SEQ ID NO: 409)

The sequences described in Table 3 are generally linear sequences. However, the materials can be in the form of nonlinear sequences containing hydrophobic or hydrophilic tails, which interact with the ECM. In one embodiment, the sequence is in the form of a "rake", wherein the tines of the rake are the hydrophilic and/or hydrophobic sequences which interact with the ECM to anchor the material to the tissue or vessel. The handle of rake contains a sequence that self-assembles.

E. Therapeutic, Prophylactic and Diagnostic Agents

The self-assembling peptide formulations may contain one or more therapeutic, prophylactic or diagnostic agents. The agents can be peptides or proteins, polysaccharides or saccharides, nucleic acids or nucleotides, proteoglycans, lipids, carbohydrates, or small molecules, typically organic compounds having multiple carbon-carbon bonds. Small molecules have relatively low molecular weights (e.g., less than about 1500 g/mol) and are not peptides or nucleic acids. The agent(s) may be naturally occurring or prepared via chemical synthesis. For example, a protein having a sequence that has not been found in nature (e.g., one that does not occur in a publicly available database of sequences) or that has a known sequence modified in an unnatural way by a human hand (e.g., a sequence modified by altering a post-translational process such as glycosylation) is a synthetic molecule. Nucleic acid molecules encoding such proteins (e.g., an oligonucleotide, optionally contained within an expression vector) can be incorporated into the compositions described herein. For example, a composition can include a plurality of self-assembling peptides and cells that express, or that are engineered to express, a protein (by virtue of containing a nucleic acid sequence that encodes the protein).

The one or more therapeutic, prophylactic or diagnostic agents can be added in combination or alternation with the self-assembling peptides. In certain embodiments, the one or more therapeutic, prophylactic or diagnostic agents can be covalently linked to the self-assembling peptides, for example, via a thio-linkage or other suitable linkages.

In one embodiment, these agents may be anti-inflammatories, vasoactive agents, coloring agents, anti-infectives, anesthetics, growth factors, and/or cells. Representative vasoconstrictors, any of which can be formulated with one or more self-assembling peptides (e.g., in a biocompatible composition in liquid, powder or gel form) include, but are not limited to, epinephrine and phenylephrine.

Representative anesthetic agents include, but are not limited to, benzocaine, bupivacaine, butamben picrate, chloroprocaine, cocaine, curare, dibucaine, dyclonine, etidocaine, lidocaine, mepivacaine, pramoxine, prilocalne, procaine, propoxycaine, ropivacaine, tetracaine, or combinations thereof. Local application of the anesthetic agent may be all that is required in some situations, for example, for a burn or other wound to the skin, including decubitus ulcers, or for minimally invasive surgeries. Combining local anesthetics with the self-assembling peptides, whether combined by virtue of being present in the same formulation or by virtue of co-administration, can help contain the anesthetic within the body and reduce the amount entering the circulation.

Vasoconstrictors such as phenylephrine can be included to prolong the effect of local anesthesia (e.g., 0.1-0.5% phenylephrine). Analgesic agents other than a local anesthetic agent, such as steroids, non-steroidal anti-inflammatory agents like indomethacin, platelet activating factor (PAF) inhibitors such as lexipafant, CV 3988, and/or PAF receptor inhibitors such as SRI 63-441.

An anti-infective or antimicrobial agent (e.g., an antibiotic, antibacterial, antiviral, or antifungal agent) can be included for either systemic or local administration. Examples include β-lactam antibiotics such as penicillins and cephalosporins and other inhibitors of cell wall synthesis such as vancomycin, chloramphenicol, tetracyclines, macrolides, clindarnyin, streptogramins, aminoglycosides, spectinomycin, sulfonamides, trimethoprim, quinolones, amphotericin B, flucytosine, azoles such as ketoconazole, itraconazole, fluconazole, clotrimazole, and miconazole, griseofulvin, terbinafine, and nystatin. The antimicrobial can be topically administered (e.g., to treat skin infections or burns, or to help prevent infection at a site of catheter insertion (e.g., an intravenous catheter), for example, kanamycin, neomycin, bacitracin, polymixin, topical sulfonamides such as mafenide acetate or silver sulfadiazine, or gentamicin sulfate. The antimicrobial can also be a broad spectrum agent. For example, a second, third, or fourth generation cephalosporin can be used. These agents may be active against a wide range of bacteria including both gram positive and gram negative species. Such antibacterial agents may be particularly appropriate where scaffolds are used to inhibit movement of intestinal contents such as during intestinal resection or other surgery that purposefully or accidentally disturbs the integrity of the intestinal wall. One of ordinary skill in the art will be able to select appropriate antimicrobial agents by considering factors such as the patient's history (e.g., any history of an allergic reaction to such agents), the location to which the peptides are to be applied, the type of infectious agent likely to be present, and so forth.

Suitable coloring agents include commercially available food colorings, natural and synthetic dyes, and fluorescent molecules. Preferably, the coloring agent is nontoxic or is included at such low concentrations as to minimize any undesirable effect (e.g., a toxic effect). The use of a coloring agent allows for improved visualization of an area that is covered by a structure or scaffold and can facilitate removal, if such removal is desired. The coloring agent can be one that changes color when it comes into contact with a contaminated area (e.g., a color change may be triggered by the contamination itself (e.g., by the blood or bacteria present at a wound site)). For example, a metabolic product of a bacterium may trigger a color change. Conditions such as pH or redox state induced by contaminants may also be detected. Exemplary coloring agents include, but are not limited to, azo red, azo yellow, arsenzazo III, chlorophosphonazo III, antipyrylazo III, murexide, Eriochrome Black T and Eriochrome Blue SE for $Mg^{2+}$, oxyacetazo I, carboxyazo II, tropolone, methylthymol blue, and Mordant Black 32. AlamarBlue, a redox indicator, and phenol red can also be used in the compositions and methods described herein.

One or more growth factors can also be included in the compositions to accelerate one or more aspects of healing (e.g., angiogenesis, cell migration, process extension, and cell proliferation). The one or more growth factors can be incorporated into the self-assembling material or may be co-administered with the self-assembling composition. Examples of growth factors include, but are not limited to, vascular endothelial growth factor (VEGF), a transforming growth factor (TGF) such as transforming growth factor β, a platelet derived growth factor (PDGF), an epidermal growth factor (EGF), a nerve growth factor (NGF), an insulin-like growth factor (e.g., insulin-like growth factor I), a glial growth factor (GGF), a fibroblast growth factor (FGF), etc. It will be appreciated that in many cases these terms refer to a variety of different molecular species. For example, several transforming growth factor β species are known in the art. One of ordinary skill in the art will be guided in the selection of an appropriate growth factor by considering, for example, the site at which the composition is to be administered. For example, an EGF can be included in compositions applied to the skin; an NGF and/or GGF can be included in compositions applied to nerves or the nervous system; and so forth.

The growth factor or another agent can be a chemotactic substance, which has the ability, in vivo or in cell culture, to recruit cells to a site at which the substance is present. The cells recruited may have the potential to contribute to the formation of new tissue or to repair existing, damaged tissue (e.g., by contributing structurally and/or functionally to the tissue (e.g., by providing growth factors or contributing to a desirable immune response)). Certain chemotactic substances can also function as proliferation agents (e.g., neurotropic factors such as NGF or BDNF).

Other suitable active agents include cyanoacrylates, oxidized cellulose, fibrin sealants, collagen gel, thrombin powder, microporous polysaccharide powders, clotting factors (e.g., Factor V, Factor VIII, fibrinogen, or prothrombin) and zeolite powders.

It will be understood that therapeutic molecules are generally administered in an effective amount in order to achieve a clinically significant result, and effective dosages and concentrations are known in the art. These dosages and concentrations can guide the selection of dosages and concentrations in the present context. Bioactive molecules can be provided at a variety of suitable concentrations and in suitable amounts (e.g., in the microgram or milligram range, or greater). For guidance, one can consult texts such as Goodman and Gilman's *The Pharmacological Basis of Therapeutics*, 10th Ed., and Katzung, *Basic and Clinical Pharmacology*.

Where cells are delivered to a patient (e.g., to promote tissue healing), autologous cells can be used. In one embodiment, the cells could be hematopoietic cells from the patient, dispersed in the material and implanted. In another embodiment, the cells can be cord blood cells.

Molded scaffolds as described above, liquid compositions, gels, solid (e.g. powders) or semi-solid embodiments may include one or more additional substances such as bioactive molecules or cells. In some instances, the cell may secrete the bioactive molecule either naturally or following genetic engineering (e.g., to express and/or secrete a recombinant protein). The structures (e.g., peptide-based structures) described herein are able to support cell attachment, viability, and growth; these have been observed when cells are cultured on the surface of a peptide-based structure or when cells grow within the material (e.g., when encapsulated). In addition, the structures are able to serve as substrates for neurite growth and synapse formation when neurons are grown on or within them. Thus, bioactive molecules and cells can be encapsulated within the peptide structures and maintain substantial function and viability when so encapsulated (see, e.g., U.S. Ser. No. 09/778,200 and 10/196,942).

F. Excipients, Carriers, and Devices

In the preferred embodiment, the formulation is a liquid or reconstitutable powder, applied topically. The formulation can include a pharmaceutically acceptable carrier or are provided as part of a medical device or coating. The formulations may also include other therapeutic, prophylactic or diagnostic agents.

In one embodiment, the formulation is provided as a dry or lyophilized powder which can be administered directly as a powder which hydrates at the site of application. Alternatively, the formulation is suspended or dissolved in a solvent, most preferably aqueous, and applied as a spray, paint, or injection. The formulation can also by administered in a hydrogel such as chitin, collagen, alginate, or a synthetic polymer. Any formulation suitable for application to the skin (e.g., a liquid, which can be applied as a spray or a powder) can be used. In another embodiment, the formulation is provided as a coating on a device, for example a stent or a catheter, which may be dissolved in an aqueous solution and dried on the device, or mixed with a polymeric carrier and applied to the device. In yet another embodiment, the formulation is provided in a bandage, foam or matrix, in which the peptides may be dispersed or absorbed. The formulation can also be in the form of sutures, tape, or adhesive. The formulation may be administered to a burn or ulcer, especially when formulated with anesthetics, anti-inflammatories, growth factors, and anti-infectives, in the form of a foam, matrix or bandage, to stop bleeding or loss of interstitial fluid.

One or more of the compositions described herein can be assembled in kits, together with instructions for use. The kit may also include one or more of a syringe (e.g., a barrel syringe or a bulb syringe), a needle, a pipette, gauze, sponges, or cotton, swabs, a bandage, a nosebleed plug, a disinfectant, surgical thread, scissors, a scalpel, a sterile fluid, a spray canister, including those in which a liquid solution is sprayed through a simple hand pump, a sterile container, or disposable gloves. In one embodiment, the kit contains an applicator which can selectively dispense several compositions which are specific for different tissues. For example, the device can contain several chambers, each of which contained a self-assembling peptide composition which is specific for a tissue. The composition can be dispensed directly onto the site of administration or can be mixed in a mixing chamber within the device prior to administration. In one embodiment, an applicator can be used to administer compositions to several types of tissues including, but not limited to, skin, muscle, brain, cardiac, liver, kidney, eye, intestine, and blood vessels.

II. Methods of Use

A. Extracellular Matrix (ECM) and Tight Junction

Extracellular matrix (ECM) is any material part of a tissue that is not part of any cell. Extracellular matrix is the defining feature of connective tissue. The ECM's main components are various glycoproteins, proteoglycans and hyaluronic acid. In most animals, the most abundant glycoproteins in the ECM are collagens. ECM also contains many other components: proteins such as fibrin, elastin, fibronectins, laminins, and nidogens, and minerals such as hydroxylapatite, or fluids such as blood plasma or serum with secreted free flowing antigens. In addition it sequesters a wide range of cellular growth factors, and acts as a local depot for them. Changes in physiological conditions can trigger protease activities that cause local release of such depots. This allows the rapid and local activation of cellular functions, without de novo synthesis. Given this diversity, ECM can serve many functions, such as providing support and anchorage for cells, providing a way of separating the tissues, and regulating intercellular communication. The ECM regulates a cell's dynamic behavior.

Tight junctions, or zonula occludens, are the closely associated areas of two cells whose membranes join together forming a virtually impermeable barrier to fluid. It is a type of junctional complex. They are formed by claudin and occludin proteins, joining the cytoskeletons of the adjacent cell. Tight junctions perform three vital functions: (1) holding cells together; (2) blocking the movement of integral membrane proteins between the apical and basolateral surfaces of the cell, allowing the specialized functions of each surface (for example receptor-mediated endocytosis at the apical surface and exocytosis at the basolateral surface) to be preserved, and thereby preserving transcellular transport; and (3) preventing the passage of molecules and ions through the space between cells, so materials must actually enter the cells (by diffusion or active transport) in order to pass through the tissue. This pathway provides control over what substances are allowed through. (e.g. Tight junctions play the control role in maintaining the blood-brain barrier.)

Disorders associated with leakage of tight junctions, include sepsis and neurodegeneration. Sepsis is the systemic response to severe infection in critically ill patients. Sepsis, sepsis syndrome, and septic shock represent the increasingly severe stages of the same disease. Severe sepsis and septic shock occur in persons with preexisting illness or trauma. If sepsis is not diagnosed and treated early, it can become self-perpetuating, and elderly persons, in particular, are at a greater risk of death from sepsis. Sepsis is associated with a profound intravascular fluid deficit due to vasodilatation, venous pooling and capillary leakage. Fluid therapy is aimed at restoration of intravascular volume status, hemodynamic stability and organ perfusion.

Circulatory stability following fluid resuscitation is usually achieved in the septic patient at the expense of tissue edema formation that may significantly influence vital organ function. The type of fluid therapy, crystalloid or colloid, in sepsis with capillary leakage remains an area of intensive and controversial discussion.

The self-assembling peptide formulations can be administered using conventional techniques, including but not limited to, topical administration and via injection. The self-assembling peptide formulations can be injected using a syringe or other suitable deliver means. The self-assembling peptide formulations can be delivered directly to a tissue using a syringe or other mechanical deliver means, i.e., spatula, brush, tubing, catheter, spraying, or a combination thereof.

Neurodegenerative disorders, such as Alzheimer's and Parkinson's disease, degrade the central nervous system, resulting in senile dementia and motor dysfunction. Currently there are preventative and therapeutic measures for Alzheimer's disease but no cure. The blood-brain barrier is essential for normal neuronal activity and loss of key features such as tight junctions may lead to neuronal impairment. The microvessel endothelial cells that form the barrier send regulatory signals to cells within the brain, providing vital instructions both during normal brain development and later in adult life. Close connections between the endothelial and surrounding cells (including differentiated glia and neurons as well as uncommitted neural precursor cells) facilitate regulatory interchange between the various cells.

The materials described herein can also be used to treat a variety of neurodegenerative disorders, whose symptoms include retraction of the tight junctions between cells, as well as for preventing leaks of the blood brain barrier.

One embodiment provides a molecular medical device formed by the disclosed self-assembling peptides. The molecular medical device can function as a scaffold for developing tissues or tissues induced to develop, differentiate, or dedifferentiate. Thus, the self-assembling peptides used to produce a particular molecular medical device will depend on the type of tissue to be treated as well as the stage of development of the tissue to be treated. In certain aspects, the self-assembling peptides can be modified to contain one or more morphogenic agents, for example bone morphogenic proteins. The morphogenic agents can be releasably attached to the self-assembling peptides and can form a gradient when present on the assembled molecular medical device or when released from the assembled molecular medical device.

B. Diabetic Retinopathy

Diabetic retinopathy is retinopathy (damage to the retina) caused by complications of diabetes mellitus, which can eventually lead to blindness. Diabetic retinopathy is the result of microvascular retinal changes. Hyperglycemia-induced pericyte death and thickening of the basement membrane lead to incompetence of the vascular walls. These damages change the formation of the blood-retinal barrier and also make the retinal blood vessels become more permeable.

Small blood vessels—such as those in the eye—are especially vulnerable to poor blood sugar control. An overaccumulation of glucose and/or fructose damages the tiny blood vessels in the retina. During the initial stage, called nonproliferative diabetic retinopathy (NPDR), most patients do not notice any changes in their vision.

As the disease progresses, severe nonproliferative diabetic retinopathy enters an advanced, or proliferative, stage. The lack of oxygen in the retina causes fragile, new, blood vessels to grow along the retina and in the clear, gel-like vitreous humour that fills the inside of the eye. Without timely treatment, these new blood vessels can bleed, cloud vision, and destroy the retina. Fibrovascular proliferation can also cause tractional retinal detachment. The new blood vessels can also grow into the angle of the anterior chamber of the eye and cause neovascular glaucoma. Nonproliferative diabetic retinopathy shows up as cotton wool spots, or microvascular abnormalities or as superficial retinal hemorrhages. Even so, the advanced proliferative diabetic retinopathy (PDR) can remain asymptomatic for a very long time, and so should be monitored closely with regular checkups.

In diabetic neuropathy, the structural ECM at the edges of the blood vessel retreat into the cell and as a result the blood vessel leaks. Self-assembling materials may be used to replace or supplement the tight junction of the blood vessels in diabetic neuropathy, as well as vessels in the brain that are also leaking due to the retraction of the tight junctions between cells. The self-assembling compositions can be administered in a variety of ways. In one embodiment, the self-assembling material is injected into the body (e.g., the eye or brain) adjacent to the leak site. In another embodiment, the self-assembling material is injected into the blood stream. The material is encapsulated by the body and released in the environment surrounding the leakage. This method is similar to the method of the activation that the body uses to repair damages to tissues. It is believed that the compositions described herein can bridge the gap between the retreating structural ECM by interacting with the sugars on the glycoproteins in the ECM or integrating into the damaged membranes around the site of injury.

Figure 2:
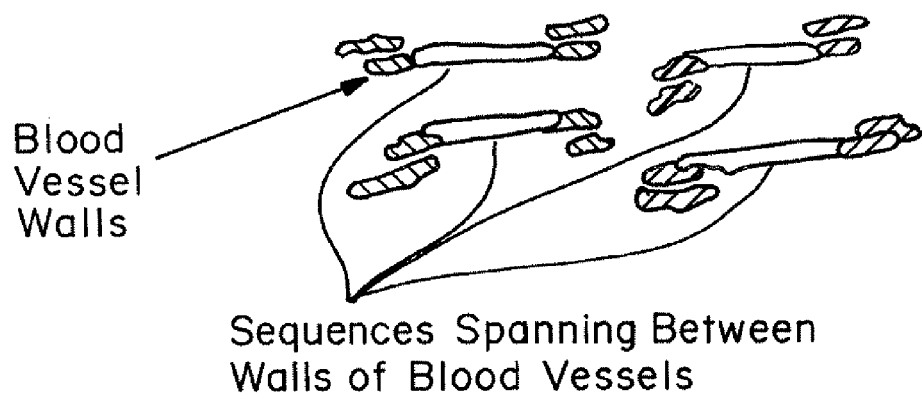
FIG. 2 shows self-assembling peptides bridging the gap between blood vessel wall cells. The peptides can contain a tail such as a hydrophobic or hydrophilic tail, which binds to or interacts with the extracellular matrix of the blood vessel anchoring the peptides to the vessel wall. Upon self-assembly, the peptides can pull the ends of the vessel together, allowing the wound or injury to heal.

FIG. 2 shows an enlarged portion of a blood vessel that is leaking fluid.

When the self assembling material is administered to the site of leakage, self assembling material assembles around the disrupted structural protein. The self-assembling material, when fully assembled, actually pulls the adjacent cells to each other.

C. Reinforcing Vessel Walls

The compositions described herein may also be used to strengthen and/or repair vessels walls, such as in patients suffering from varicose veins. The materials can also be used to reinforce vessel walls in other organs or tissues such as the eye or intestine as well as the organ walls themselves. Templates can be added to the self-assembling material which allow for the coupling of the self-assembling material to the sugars of the extracellular matrix (ECM) of blood vessels for a given tissue. The material spans the entire site of injury upon coupling to the ECM and may be able to bring the blood vessel walls back together to stop leaks. The chemical composition of the templates to be added to the self-assembling material depends on the composition of ECM of the blood vessels of the tissue to be treated. ECM for blood vessels in the brain is different from ECM in the other organs, such as the liver, eyes, heart, etc. One of ordinary skill in the art will be able to determine the appropriate template based on the tissue to be treated. For example, excess ADADADs (SEQ ID ID NO: 410) can be added to the ends of the self-assembling materials. The ADADAD (SEQ ID NO: 410) fragments should be complementary with the ECM sugars of various types of cells. However, templates can be designed that are specific for one type of tissue. Further, hydrophobic templates, such as segments of hydrophobic amino acid residues, can be added to the ends of the self-assembling materials which would allow the materials to integrate into the ECM. The self-assembling nanofiber scaffold is biocompatible and the degradation products, L-amino acids in the case of peptides, can be used by cells as building blocks for cell growth and repair.

D. Burns

Proper fluid management is critical to the survival of the victim of a major thermal injury. In the 1940's, hypovolemic shock or shock-induced renal failure was the leading cause of death after burn injury. Today, with the current knowledge of the massive fluid shifts and vascular changes that occur during burn shock, mortality related to burn-induced volume loss has decreased considerably. Although a vigorous approach to fluid therapy has ensued in the last 20 years and fewer deaths are occurring in the first 24-48 hours post-burn, the fact remains that approximately 50% of the deaths occur within the first 10 days following burn injury from a multitude of causes, one of the most significant being inadequate fluid resuscitation therapy. Knowledge of fluid management following burn shock resuscitation is also important and is often over-looked in burn education.

Burn shock is both hypovolemic shock and cellular shock, and is characterized by specific hemodynamic changes including decreased cardiac output, extracellular fluid, plasma volume and oliguria. As in the treatment of other forms of shock, the primary goal is to restore and preserve tissue perfusion in order to avoid ischemia. However, in burn shock, resuscitation is complicated by obligatory burn edema, and the voluminous transvascular fluid shifts which result from a major burn are unique to thermal trauma. Although the exact pathophysiology of the postburn vascular changes and fluid shifts is unknown, one major component of burn shock is the increase in total body capillary permeability. Direct thermal injury results in marked changes in the microcirculation. Most of the changes occur locally at the burn site, when maximal edema formation occurs at about 8-12 hours post-injury in smaller burns and 12-24 hours post-injury in major thermal injuries. The rate of progression of tissue edema is dependent upon the adequacy of resuscitation.

Fluid resuscitation is aimed at supporting the patient throughout the initial 24-hour to 48-hour period of hypovolemia. The primary goal of therapy is to replace the fluid sequestered as a result of thermal injury. The critical concept in burn shock is that massive fluid shifts can occur even though total body water remains unchanged. What actually changes is the volume of each fluid compartment, intracellular and interstitial volumes increasing at the expense of plasma volume and blood volume.

It is quite clear that the edema process is accentuated by the resuscitation fluid. The magnitude of edema will be affected by the amount and type of fluid administered. The National Institutes of Health consensus summary on fluid resuscitation in 1978 was not in agreement in regard to a specific formula; however, there was consensus in regard to two major issues— the guidelines used during the resuscitation process and the type of fluid used. In regard to the guidelines, the consensus was to give the least amount of fluid necessary to maintain adequate organ perfusion. The volume infused should be continually titrated so as to avoid both under-resuscitation and over-resuscitation. As for the optimum type of fluid, there is no question that replacement of the extracellular salt lost into the burned tissue and into the cell is essential for successful resuscitation.

One of the acute features of cutaneous thermal injury is the swelling of the involved tissue. This swelling is caused by a fluid shift from circulating plasma. Along with the evolution of intravenous fluid therapy in trauma and surgery, the implementation of such therapy to burn victims has improved survival. Edema generation aggravated by fluid therapy may, however, represent a source of increased morbidity. It is well documented that fluid is lost from the circulation into burned tissue because of a moderate increase in capillary permeability to fluid and macromolecules and a modest increase in hydrostatic pressure inside the perfusing microvessels. Recently it was discovered that a very negative interstitial pressure develops in thermally injured skin. This pressure constitutes a strong "suction" adding markedly to the edema generating effect of increased capillary permeability and pressure.

Application of the materials described herein can be utilized to decrease edema, balance negative interstitial pressure, and prevent further fluid loss at the site of burn injuries.

Moreover, the self-assembling material can be formulated in the form to be applied to the injured skin surface of the patients directly. The temperature of the formulation could be adjusted to the level at which the patients are comfortable with.

One embodiment provides a topical electrolyte maintenance solution in combination with the self-assembling peptides for burn victims containing an effective amount of electrolytes to cause fluid movement into the skin from the maintenance solution. The self-assembling peptides forms a barrier to prevent fluids from moving out of the skin. The solution can be cooled or contain an anesthetic. In another embodiment, the electrolye solution can also used in lungs to stop fluid movement and thereby prevent or treat pneumonia in the lungs. Alternatively, the composition can be administered as a powder or solution, superloaded with oxygen to keep oxygen exchange high and minimize or prevent damages to the lungs.

In another embodiment, the self-assembling peptides can form a multilayered structure such as a barrier to cover a wound. The inner layer, or layer in contact with the wound, can be hydrophilic. Such multilayer structures can be formed on a variety of tissues, including the lungs.

E. Prevent Movement of Fluids

As the compositions described here can be used to inhibit movement of a bodily substance in a subject, including movement within or from the epidermis, the compositions can be employed in the context of performing surgery and may be described as new methods for performing surgery or generating a surgical field. The methods, whether performed in the context of surgery or not, can include a step of identifying a subject in need of treatment and a step of providing a nanoscale structured material, or a precursor thereof, at or in the vicinity of a site where unwanted movement has occurred or is expected to occur. The amount of the composition administered and the concentration of self-assembling peptides therein can be sufficient to inhibit the unwanted movement of a bodily substance. For example, one can identify a patient who is about to undergo a surgical procedure and provide a biocompatible composition comprising self-assembling peptides and a vasoconstrictor, a coloring agent, or a local anesthetic agent to a site at which an incision or other invasive maneuver will be made or has been made. The bodily substance that is affected may be a fluid such as blood or a blood product, serous exudate (an inflammation-associated exudate composed largely of plasma, which typically appears as a clear or amber-colored fluid), pus, gastric juice, urine, bile, cerebrospinal fluid (CSF), pancreatic juice, and the like. The bodily substance may be viscous, sludge-like or semi-solid but will generally exhibit an ability to flow or move. Substances of this nature include the contents of the gastrointestinal tract. The composition may be removed after application (e.g., after hemostasis is achieved or an operation on the bowel is complete) or may be left in place. For example, the compositions can be applied to accelerate hemostasis or inhibit movement of intestinal contents during surgery and some or all of the scaffold may be left in place when the operation is complete. This provides a substantial advantage relative to the use of sponges and other materials that must be removed prior to closure. The compositions can be removed in a variety of ways (e.g., by wiping or by suction).

The compositions can also be applied to shield an underlying area (e.g., an area of burned or otherwise injured skin or other tissue) and can, therefore, help to prevent contaminants (e.g., foreign substances) from coming into contact with the area (i.e., the compositions can be used as a barrier or shield). A physician or other health-care provider can examine a wound through the material, and a surgeon can operate through it, while it is in place. Contaminating substances that have landed on the material during the procedure could then be removed by virtue of removing the material.

The compositions can be administered to stabilize a wound prior to definitive treatment (e.g., while the victim is awaiting transport to a hospital or during transit). The compositions are similarly useful where operations are conducted under conditions of less than optimal sterility (e.g., in field hospitals or in areas of the world where access to sterile operating rooms is limited). The compositions and methods have the potential to significantly reduce the likelihood of contamination in instances such as these.

The self-assembling peptide material can also be locally applied in combination with anesthetic in the local area where a procedure is to take place and can be applied at a higher concentration to reduce organ movement during surgery. This may reduce cognitive deficits to older patients by reducing the general anesthetic load. A thin layer can be sprayed on the tissue or skin where the surgeon is operating. It can be applied separately or together, administering specific anesthetic for specific organs. Skin has different receptors than intestines and the need for a specific anesthetic is needed for each of the organs. Intestines need to stop moving during surgery while the blood and blood vessel contraction need to remain constant.

Treatment and Prevention of Bleeding

Any individual who has an increased risk of suffering undesirable bleeding, which may or may not be excessive or immediately life-threatening, can be treated with the compositions described herein. These individuals include those with blood clotting disorders such as hemophilia, patients who are receiving anticoagulant therapy, patients who suffer recurrent nosebleeds, and individuals undergoing surgery, particularly major surgery or procedures that involve accessing an artery. Without limitation, the surgery or procedure can be an operation on the nervous system, eye, ear, nose, mouth) pharynx, respiratory system, cardiovascular system, digestive system, urinary system, musculoskeletal system, integumentary (skin) system, or reproductive system. As noted, the compositions can also be applied to tissues exclusive of those that define the central nervous system (i.e., the brain and spinal cord). Specific examples of surgeries and procedures in which the compositions can be used include arteriography, angiocardiography, cardiac catheterization, repair of obstetric laceration, removal of coronary artery obstruction, insertion of stent, Caesarean section, hysterectomy, reduction of fracture, coronary artery bypass graft, cholecystectomy, organ transplant, total joint (e.g., knee, hip, ankle, shoulder) replacement, appendectomy, excision or destruction of intervertebral disk, partial excision of the large intestine, mastectomy, or prostatectomy. The surgical procedure can involve the intentional or unintentional transection of a blood vessel or causing the release of a bodily substance other than blood.

Accident victims, individuals engaged in combat, and women giving birth are also at risk of experiencing significant blood loss. The compositions can be applied to a site of obstetric bleeding (e.g., within the uterus, vagina, or neighboring tissue) in order to accelerate hemostasis. For example, the compositions can be applied to a placental tear or used to pack the uterus to control bleeding. As with other indications, compositions applied to the reproductive tract can be removed or left in place. Spontaneous hemorrhage, aneurysm rupture, esophageal varices, gastric ulcers, ulcers of the upper portion of the intestine (e.g., duodenal ulcers) are also medical conditions in which considerable bleeding can occur, and these individuals can also be treated as described here.

The precise source of the bleeding can vary and can be from any blood vessel in the arterial or venous system (e.g., an artery, arteriole, capillary or capillary bed, venule, or vein). The size of the vessel may range from large (e.g., the compositions can inhibit bleeding from the aorta, the iliac or femoral artery, or a portal vein) to small (e.g., a capillary), and the vessel may be located anywhere in the body (e.g., in a solid organ such as liver, the stomach, intestine, skin, muscle, bone, the lungs, or the reproductive system).

The time normally required for blood clotting can be prolonged when plasma levels of clotting factors and/or platelets are low or in cases in which an individual has received an anticoagulant (e.g., warfarin or heparin). Bleeding frequently persists for considerably longer than the average clotting time when there is more than minimal damage to blood vessel integrity. Based on the studies, it is expected that the compositions will cause hemostasis in a period of time that is less than, and in at least some cases much less than, the average blood clotting time. Although the compositions are not limited to those that achieve hemostasis in any given time (and uses such as protecting an area from contamination or promoting tissue healing are independent of this function), the compositions may confer a benefit to a bleeding subject in as little as five seconds following application. Other compositions can exert an effect in about 10, 15, or 20 seconds following application. The effective period can be characterized in a manner other than absolute time. For example, compositions may reduce the time required to achieve hemostasis by between 25% and 50%; between 50% and 75%; or between 75% and 100% relative to the time required when iced saline is applied. The time required to achieve hemostasis can be reduced by approximately 2-, 3-, 4-, or 5-fold relative to the time required when iced saline is applied.

The peptide concentration may be selected with reference to variables such as the caliber of the vessel, the extent to which it has been injured, and the force with which blood is exiting (or would exit upon injury). Higher peptide concentrations will be desirable to promote hemostasis from a major vessel (e.g., the aorta, brachiocephalic, carotid, subclavian, celiac, superior mesenteric, renal, iliac, femoral, or popliteal arteries). Useful concentrations can range from between approximately 0.1-10% (e.g., 1-10%; 0.5-5%; 1-4%; 0.1-2%; 0.1-3%; 0.1-4%; 0.1-5%; and 1-8% (e.g., about 1, 1.5, 2, 2.5, 3, 4, 5, 6, or 7%). Any subrange, or any specific value within any of the aforesaid ranges, can be used. Any of the aforementioned concentrations may also be used for the other indications described herein.

As noted, bleeding can be due to any of a large number of different causes and can be internal or external. The compositions can be applied regardless of the cause or the nature of the cause (e.g. whether caused by a disease process or intentional or accidental trauma). The compositions can be used to achieve hemostasis in a confined space (e.g., inside a hollow organ) or at or near the body's surface. For example, the compositions can be applied to a partly or completely severed body part such as a limb or digit. In that event, the compositions may be serving multiple functions; they may not only promote hemostasis, but also protect the wounded tissue from contaminants and promote tissue healing. More specifically, the compositions can be applied to a wound, left in place for a period of time sufficient to achieve hemostasis and for blood clotting to occur, and then removed. Contaminating material such as particulates and infectious agents adhered to the peptide gel would be removed with it. A sterile dressing may then be applied. Of course the compositions can be applied for purposes of cleaning a wound, preventing contamination, or promoting tissue healing even after hemostasis has been achieved or in situations in which acceleration of hemostasis is not needed.

When used to treat a nosebleed, the compositions are inserted into the appropriate nostril and can be left in place until the bleeding has subsided. The compositions can be easily removed by suction (e.g., using an eyedropper or syringe) or may be removed by other physical means, including simply blowing the nose. If desired, the compositions can be administered to the nose by way of inclusion on one or more surfaces of a nosebleed plug.

The compositions can also be left in place on a wound, and a dressing can be applied over the composition. Since the composition itself is easily removed, its presence under the dressing can help prevent the dressing from sticking to the damaged tissue. If desired, a bandage having a transparent portion may be used so the injured site can be viewed through the transparent portion of the bandage and the peptide structure below. This would allow a physician to monitor the progress of the healing without removing the dressing. Modified bandages are described further below and are within the scope of the present invention.

Many medical procedures involve vascular puncture, which can be followed by significant bleeding. A self-assembling peptide composition can be applied to the wall of a punctured vessel, e.g., during withdrawal of an instrument used to puncture the vessel. A vascular plug formed from self-assembling peptides provides an alternative to existing vascular plugs and devices such as those described in U.S. Pat. Nos. 5,192,302; 5,222,974; 5,645,565; and 6,663,655. The vascular plug can be formed in situ (e.g., at a site of vascular puncture), or can be preformed and applied to the site.

More generally, compositions comprising nanostructured materials or precursors thereof (e.g., self-assembling peptides) can be used for sealing any passage through tissue. The present methods therefore include methods of sealing a passage through tissue by applying a composition comprising a nanoscale structured material (e.g., self-assembling amphiphilic peptides) to one or both ends of the passage or to its interior. The tissue can be, for example, the wall of a blood vessel, the wall of an organ, subcutaneous tissue, or adipose tissue. Sealing the passage can result in hemostasis. The passage can also be a fistula (i.e., an abnormal connection between two organs or body structures or between an organ or structure and the external world). If desired, a surgeon can apply the compositions to the interior of a tubular structure such as the intestine or a blood vessel, resect and ligate the intestine or blood vessel in the gel, and evacuate the gel from the interior of the structure to restore continuity of the structure and allow reperfusion of the area with blood or other body substances.

For surgical applications, the wound or any part of the surgical field can be packed with a composition comprising self-assembling peptides. This approach can be used instead of wound packing as it is conventionally performed during surgery. As the compositions contain biocompatible and biodegradable material, they can be left in place, thereby avoiding the need for removal at the end of the procedure and avoiding the need for a subsequent operation for this purpose. Biodegradable materials can be broken down physically and/or chemically within cells or within the body of a subject (e.g., by hydrolysis under physiological conditions or by natural biological processes such as the action of enzymes present within cells or within the body) to form smaller chemical species which can be metabolized and, optionally, reused, and/or excreted or otherwise disposed of. Preferably, the biodegradable compounds are biocompatible.

Gastrointestinal bleeding, which can occur as a consequence of ulcers or angiodysplasia, is a relatively common and serious condition that can be fatal if left untreated. Bleeding esophageal varices, and bleeding gastric or duodenal ulcers can be particularly severe. A number of endoscopic therapeutic approaches have been developed to achieve hemostasis, such as the injection of sclerosing agents, the attachment of mechanical hemostatic devices, and contact electrocautery techniques. The compositions can be administered at, or in the vicinity of, an ulcer or a site of bleeding in the esophagus, stomach, small intestine, or large intestine. Bleeding in the distal portion of the large intestine, rectum, or anus (e.g., hemorrhoids) can also be treated in this manner.

Rupture of an aneurysm can represent a catastrophic event with rapidly fatal consequences. Ruptured aortic aneurysms can rapidly result in exsanguination despite prompt medical attention. Ruptured intracranial aneurysms frequently have devastating consequences. The compositions and methods of the invention can be used to treat bleeding from a ruptured aneurysm in an essentially similar manner to the way in which they are used to treat bleeding due to other causes (e.g., by application of self-assembling precursors or a preformed structure to the site of bleeding). Given the often severe consequences of aneurysm rupture, surgical repair is often attempted. The compositions can be applied in the context of any attempted repair (e.g., during open surgery or endovascular repair (e.g., with placement of a graft and/or stent)). More specifically, the present methods include treating an aneurysm by introducing a composition comprising a nanoscale structured material or precursor thereof (e.g., a composition comprising self-assembling peptides) into the aneurysm (e.g., into the aneurysm sac). Once any bleeding is under better control, the aneurysm may then be repaired using any suitable technique. Presence of the peptide structure within the aneurysm sac reduces the chance of leakage or rupture prior to or during these other procedures. The scaffold can be left in place.

Inhibiting Movement or Leakage of Cerebrospinal Fluid (CSF)

The dura mater is the tough, outermost, fibrous membrane that covers the brain and spinal cord, and lines the inner surface of the skull. Leakage of CSF is a significant complication following injury, surgery, or other procedures in which the dura mater is penetrated, including inadvertent penetration in the course of administering an anesthetic to the epidural space. Such leakage can lead to serious sequelae, such as severe headaches, infection, and meningitis. The composition can inhibit movement or leakage of CSF in a subject in need thereof after application at, or in the vicinity of, a site of unwanted movement or leakage of CSF. The compositions can be applied over sutures following dura mater surgery to help prevent CSF from leaking out of the incision site.

The compositions can also be used to inhibit movement or leakage of fluid from the ear drum.

Inhibiting Leakage of Contents of the Gastrointestinal Tract

The compositions can inhibit the movement of gastrointestinal contents. For example, the structures can prevent leakage of gastrointestinal contents following gastric or intestinal perforation or during surgery (see Example 4). The structures can be used to isolate such bodily substances and prevent their spread within the peritoneal cavity, thereby minimizing contamination and the risk of subsequent chemical peritonitis and/or infection. Gastric contents, which contain digestive secretions of the stomach glands consisting chiefly of hydrochloric acid, mucin, and enzymes such as pepsin and lipase, can cause injury and/or infection if released into the peritoneal cavity. Release of intestinal contents into the peritoneal cavity represents a frequent event during surgery on the intestine and can also occur in cases of intestinal perforation or a ruptured appendix. The composition can be used to inhibit leakage of gastrointestinal contents into the peritoneal cavity. The site of movement can be a site of gastric or intestinal damage caused by a disease process or a surgical incision. The compositions can be applied to the exterior of any organ in the digestive system (e.g., the stomach, or small or large intestine) or can be injected or otherwise introduced into their interior. The compositions can be administered in the course of resecting a segment of the intestine. For example, one can fill a segment of intestine that extends from a first point to a second point with a present composition and resect a portion of the intestine that lies between the first and second points.

In a related method, one can use the compositions to remove intestinal contents that have been released into the peritoneal cavity. The method includes applying a liquid composition to the released intestinal contents, allowing the liquid composition to undergo a phase transition, and then removing the gel-like or semi-solid composition. These steps can be repeated once or more until the surgeon is satisfied with the amount of intestinal contents that have been removed from the peritoneal cavity.

One can similarly inhibit movement of the contents of other internal organs (e.g., organs in the biliary or urinary systems). For example, one can inhibit movement of bile, pancreatic juice (i.e., secretions of the exocrine portion of the pancreas that contain digestive enzymes), or urine and/or decontaminate or clean an area into which bile, pancreatic juice, or urine have been released by application and subsequent removal of the compositions to the site. The methods thus have broad application to surgeries for repairing or otherwise treating intestinal, biliary, and/or urinary system defects. As noted herein, the compositions can be applied to the skin or to an incision in the skin or the wounded tissue underneath to reduce the likelihood of contamination from a microbe such as a bacterium. The methods can be used to decontaminate the site to which they have been applied by removing the compositions at a subsequent time (e.g., upon the completion of a surgical procedure).

Wound Healing

Studies also indicate that the compositions have the ability to enhance healing, particularly of an epithelial layer or muscle, and can therefore be administered to treat a site of tissue damage. For example, one can apply a composition including self-assembling peptides to the site of tissue damage. The compositions appear to both increase the rate of tissue repair and inhibit formation of scar tissue. The compositions can be used for either acute or chronic wound care. For example, they can be applied to skin wounded in any manner (e.g., lacerated or burned) and to lesions such as diabetic ulcers and pressure sores.

Unless defined otherwise, all technical and scientific terms used herein have the same meanings as commonly understood by one of skill in the art to which the disclosed invention belongs. Publications cited herein and the materials for which they are cited are specifically incorporated by reference.

Transmission Electrode Microscopy Sample Preparation.

In the brain and liver of anesthetized adult rats 1% or 2% of NHS-1 was injected immediately after making a cut and the treatment site was sampled. Samples were fixed in a mixture of 2% para-formaldehyde and 2.5% glutaraldehyde in 0.1M PB for 4 hours. The samples were washed in 0.1M PB buffer 10 min×3 at 4° C. and embedded in 2% agar. Agar blocks were post fixed in 1% osmium tetroxide for 2 hrs at 4° C. and then washed in buffer for 10 min×3 at 4° C. The sample blocks were dehydrated in ethanol infiltrated and embedded in pure epon with Lynx EM tissue processor. Ultra-thin 70 nm sections were cut (Reichert-Jung ultra cut) and collected on #200 mesh grids. Sections and grids were stained with uranyl acetate and lead citrate and examined under Philip EM208S transmission electron microscope.

Preparation of the Self-Assembling Solutions.

The NHS-1 solution was prepared using RADA16-I (SEQ ID NO: 60) synthetic dry powder (obtained from the Massachusetts Institute of Technology Center for Cancer Research Biopolymers Lab, Cambridge, Mass.; the Zhang lab and 3-DMatrix, Cambridge, Mass.) dissolved in an Eppendorf tube. The 1% NHS-1 solution was prepared by dissolving 10 mg of RADA16-I (SEQ ID NO: 60) powder in 1 ml of autoclaved Milli-Q water (Millipore corp. Billerica, Mass.), sonicated for up to five minutes and filtered. This was repeated with 20 mg/ml, 30 mg/ml, and 40 mg/ml to produce 2%, 3% and 4% concentrations. NHS-2 and TM-3 dry powders (made by the Massachusetts Institute of Technology Center for Cancer Research Biopolymers Lab, Cambridge, Mass.) were prepared using the same method. The time of preparation did not affect the action of the solution. Some material that was prepared (obtained from Zhang lab), and stored in solution at room temperature, for three years prior to use, was also tested and shown to performed as well as the newly mixed material.

Example 1

Hemostasis in a Brain Injury

Methods and Materials

Adult Syrian hamsters were anesthetized with an intraperitoneal injection of sodium pentobarbital (50 mg/kg) and adult rats were anesthetized with an intraperitoneal injection of ketamine (50 mg/kg). The experimental procedures adhered strictly to the protocol approved by the Department of Health and endorsed by the Committee on the Use of Laboratory Animals for Teaching and Research of the University of Hong Kong and the Massachusetts Institute of Technology Committee on Animal Care.

Figure 4A:
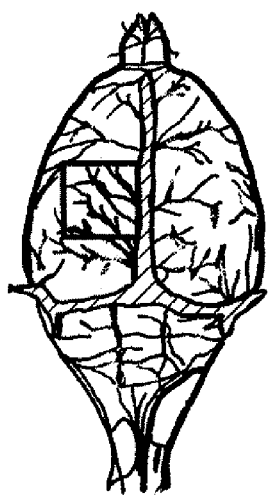
FIGS. 4a-d are schematics of surgical procedures. Rostral is up and caudal is down in all figures. (a) Dorsal view of the rat brain. The blue lines depict the blood vessels superficial to the cortex. The boxed area corresponds to location of the lesion and treatment. (b) Drawing of ventral view of the lower limb of a rat with the femoral artery in red and sciatic nerve in yellow. (c and d) Drawings of a ventral view of rat with abdomen open, overlying structures have been removed exposing the liver. The lobe was transected with a cut (depicted in red) in sagittal (c) and transverse (d) directions.

The animals were fitted in a head holder. The left lateral part of the cortex was exposed. Each animal received a transection of a blood vessel leading to the superior sagittal sinus (FIG. 4a). With the aid of a sterile glass micropipette, 20 µl of 1% NHS-1 solution was applied to the site of injury or iced saline in the control cases. The animals were allowed to survive for up to six months.

Results

Figure 3A:
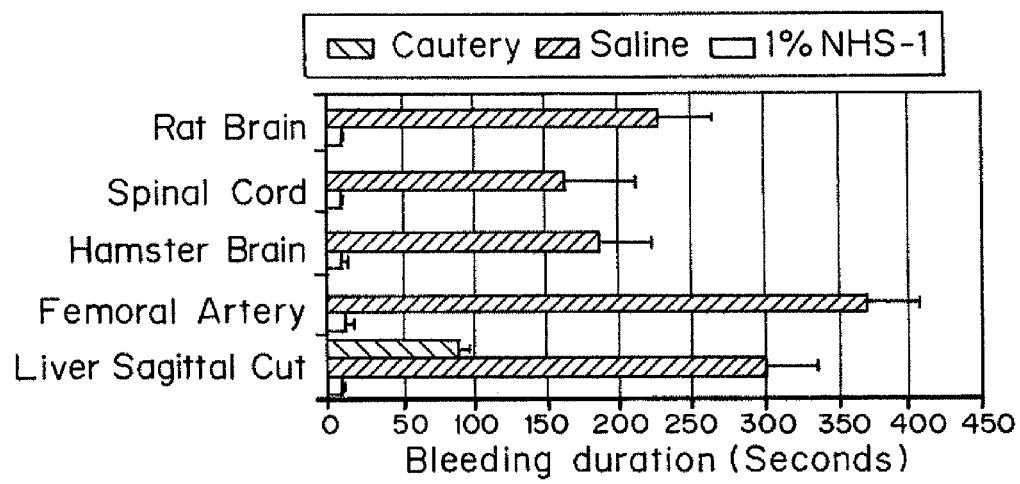
FIGS. 3a-d show bar graphs of the time taken to achieve hemostasis. These graphs illustrate bleeding durations in cases treated with 1% solution of RADA16-I (NHS-1) self-assembling solution compared with those cautery and saline treated controls for brain, femoral artery and liver cuts (a), liver punches (b) and skin punches (c). Each bar shows the mean time in seconds for NHS-1 treated cases in (red), saline controls in (blue) and cautery controls in (yellow). (a) Rat Brain. Durations were measured from the start of application of self-assembling NHS-1 to the completion of hemostasis after transection of the veins leading to the superior sagittal sinus in the brain of adult rats. Complete hemostasis was achieved in 8.4+2.1 seconds. In the saline controls, bleeding continued until 227.0+36.6 seconds. Hamster brain. Complete hemostasis was achieved in 9.0+1.8 seconds. In the saline controls, bleeding continued until 187.6+34.7 seconds. Femoral artery. Complete hemostasis was achieved in 10.5+4.1 seconds. In the saline controls, bleeding continued until 367.5+37.7 seconds. Liver sagittal cut. Complete hemostasis was achieved in 8.6+1.7 seconds. In the cautery control (yellow), bleeding continued until 90.0+5.0 seconds, and the saline controls bled for 301.6+33.2 seconds. (b) Liver 4 mm punch biopsy. A 4 mm core was removed from the left liver lobe and the hole was treated with NHS-1, heat cautery, or saline. Treatment of 3% NHS-1 brought about complete hemostasis in 9.7+1.2 seconds. In the cautery controls (yellow), bleeding continued for 81.2+6.7 seconds and the saline controls bled 204.3+49.6 seconds. (c) Skin 4 mm punch biopsy. A 4 mm punch biopsy was made on the backs of nude mice. The biopsy extended through the dermis and the core was removed. Care was taken not to disrupt the underlying muscle. The three wounds on one side were treated with 1% NHS-1 and complete hemostasis was achieved in 6.4+1.5 seconds. On the opposite side of the animal the wounds were not treated. Bleeding continued until normal clotting occurred at 75.5+16.3 seconds. (d) Concentration response curves of NHS-1 and EAK-16 (TM-3). The left lateral liver lobe received a transverse cut severing a portion of the liver lobe and branch of the portal vein. A higher concentration of NHS-1 (open circles) is more effective in higher pressure and volume bleeds. 4%, 3%, and 2% concentrations of NHS-1 were effective in achieving hemostasis in 11.0+1.0 seconds, 10.0+1.0 seconds and 10.3+0.5 seconds respectively. 1% NHS-1 took 86.6+20.8 seconds at the area of the most severe bleeding. TM-3 (diamonds) was not effective at any concentration; in the saline controls bleeding continued until 377.5+85.0 seconds and one animal died. X axis is time (seconds); y axis is concentration.

Initial experiments in the brain included removing the overlying skull and performing a complete transection of a branch of the superior sagittal sinus in the brain of rats (n=15) and hamsters (n=15) (FIG. 3A). The areas were treated with 20 µl of 1% solution of RADA16-I (SEQ ID NO: 60) (NHS-1) self-assembling solution or with iced saline.

In the NHS-1 treated groups hemostasis was achieved in less than 10 seconds in both hamsters and rats (FIG. 4a-d) Control group hamsters (n=5) and rats (n=5) irrigated with saline, bled for more than 3 minutes (FIG. 3A). Student t test for two independent samples in both hamsters and rats showed highly significant differences (p<0.0001).

Example 2

Hemostasis in a Spinal Cord Injury

Methods and Materials

Under an operating microscope, the second thoracic spinal cord segment (T2) was identified before performing a dorsal laminectomy in anesthetized adult rats. After opening the dura mater, a right hemisection was performed using a ceramic knife. Immediately after the cord hemisection 20 µl of 1% solution of RADA16-I (SEQ ID NO: 60) (NHS-1) was applied to the area of the cut for bleeding control. The controls received a saline treatment. The animals were allowed to survive for up to 8 weeks as part of another experiment.

Results

The spinal environment and the brain environment were investigated for similarities or differences. Secondary damage caused by surgery can be reduced by quickly bringing bleeding under control. After laminectomy and removal of the dura, the spinal cord was hemisected at T2, from the dorsal to ventral aspect and treated (N=5) with 20 µl of 1% NHS-1. Hemostasis was achieved in 7.6 seconds. In the saline controls (n=5) it took on average 163 seconds to stop bleeding (FIG. 3a). Comparison of the treated group and the saline controls using the Student t test for two independent samples showed highly significant difference (p<0.0001).

Example 3

Hemostasis in a High Pressure Femoral Artery Wound

Methods and Materials

Figure 4B:
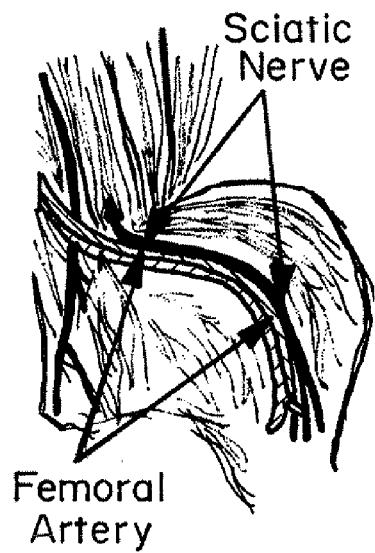

Rats were placed on their backs and the hind limb was extended to expose the medial aspect of the thigh (FIG. 4b). The skin was removed and the overlying muscles were cut to expose the femoral artery and sciatic nerve. The femoral artery was cut to produce a high pressure bleeder. With a 27 gauge needle, 200 µl of 1% RADA16-I (SEQ ID NO: 60) (NHS-1) solution was applied over the site of injury. In two cases powder was applied to the injury site which also worked. (Data not shown and was not included in the analysis). Controls were treated with a combination of saline and pressure with a gauge. All animals were sacrificed four hours after the experiment.

Results

The femoral artery of 14 adult rats was surgically exposed, transected and then treated with 200 µl of 1% solution of NHS-1 or iced saline and packing. The treated cases (n=10) took about 10 seconds to achieve hemostasis (FIG. 3a). The controls (n=4) continued to bleed more than 6 minutes. The difference in times to achieve complete hemostasis was highly significant (Student t test p<0.0001).

Example 4

Hemostasis in Highly Vascularized Liver Wounds

Methods and Materials

Figure 4C:
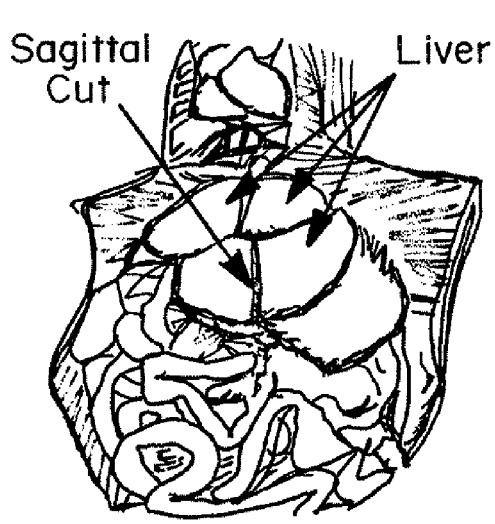
Figure 4D:
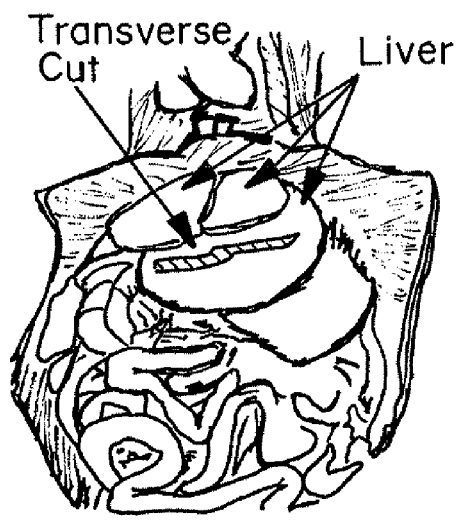

Rats were anesthetized and placed on their back and the abdomen was opened exposing the liver (FIG. 4c). The left lobe of the liver was cut using a scalpel in the rostral to caudal direction separating the two halves of the lobe in the sagittal cut. With a 27 gauge needle, 100 µl of 1% or 2%, of RADA16-I (SEQ ID NO: 60) (NHS-1), RADA-12 (NHS-2), or EAK-16 (TM-3) solution was applied to the site of injury. Livers of the controls were treated with saline or cauterized. Cauterization was performed using a thermal cautery device and was applied to entire surface of the injury. In another group of adult rats the same procedure was followed for the liver, which was cut transversely (FIG. 4d). With a 27 gauge needle, 400 µl of 1%, 2%, 3%, or 4% of NHS-1, or TM-3 solution was applied to the site of injury.

TM-3 is a stiffer gel: 1% TM-3 is similar in stiffness to 3% NHS-1. Three different concentration levels, 1%, 2%, and 3% were tried and it was found that TM-3 was not effective at any concentration; the assembled material fractured and the TM-3 treated animals continued to bleed regardless of the concentration used. There was actually no significant difference between TM-3 and the controls (FIG. 3d) in achieving hemostasis.

In another group of anesthetized adult rats, the liver was exposed and a 4 mm punch biopsy from the ventral aspect through the liver to the dorsal surface of the left liver lobe. The resulting core was removed from the liver and one of three treatments was applied. In one treatment, 200 μl of a 3% NHS-1 solution was applied to the site of injury. In one control saline was applied to the site of injury. In a second control, the injury surface was cauterized. The superficial material was then wiped clear of the injury site. The abdominal incision was closed and the animals were allowed to survive for up to eight weeks.

In anesthetized adult nude mice using aseptic precautions, a 4 mm punch was used to create three wounds on each side of the back of the animal. On one side of the animal the wounds created were treated with 1% NHS-1 solution and the wounds on the opposite side were left untreated for a control. The punch biopsies were made through the fill thickness of the skin. If the wound did not bleed for ten seconds the punch would be excluded from the data analyzed. All procedures were videotaped and the analysis was done by reviewing the tapes. The animals were allowed to survive for up to two months. If animals involved in any of the above experiments appeared to experience any discomfort they were euthanized.

Results

Three different liver cuts using a group of 76 rats were performed 1) A sagittal (rostral caudal) cut to explore NHS in an irregular-shaped laceration wound; 2) a transverse (lateral medial) cut involving the transection of a major branch of the hepatic portal vein to intensify bleeding; and 3) 4 mm punches through the liver lobe to observe the material in uniform wounds. In the first liver experiment a sagittal cut in the left lobe (n=8) was made and upon treatment of 100 μl of 1% NHS-1 solution bleeding ceased in less than 10 seconds. In one set of controls (n=3) bleeding stopped at 90 seconds (FIG. 3a) following cauterization of the wound; in the saline treated control animals (n=3) bleeding continued for more than 5 minutes. Comparison of the cauterized group and the saline treated controls shows a significant difference using the Tukey test with a 99% confidence interval.

In the second experiment a major branch of the portal vein was severed while making a transverse cut in the left lobe to test NHS-1 in a high flow rate environment. Four concentrations of NHS-1 were tested (n=12) along with (n=4) control animals. 400 μl of 4% concentration NHS-1 was applied and bleeding stopped in 11 seconds. The test was successfully duplicated with 400 μl of both 3% and 2% NHS-1 solution; bleeding ceased in 10 and 10.3 seconds, respectively (FIG. 3d). When 400 μl of 1% NHS-1 was applied, bleeding continued for more than 60 seconds (FIG. 3d). The controls, however, bled for over 6 minutes. The dose response shows that treatment results using 3% and 4% NHS-1 are nearly the same as with the 2% concentration. Furthermore, in the 2%, 3% and 4% concentration treatment cases complete hemostasis was maintained after removing the excess assembled NHS-1 material. It was found that the higher blood pressure/flow rate transverse liver cut required a concentration of 2% NHS-1 or higher to bring about complete hemostasis in less than 15 seconds. A significant difference was found between the NHS-1 treated and control groups using ANOVA. When each treatment group was compared to the control group those differences were also significant, a Tukey test showed a 9% confidence interval. There was no significant difference when the various NHS-1 concentrations were compared, except for the 1% NHS-1 solution treatment group.

Figure 3B:
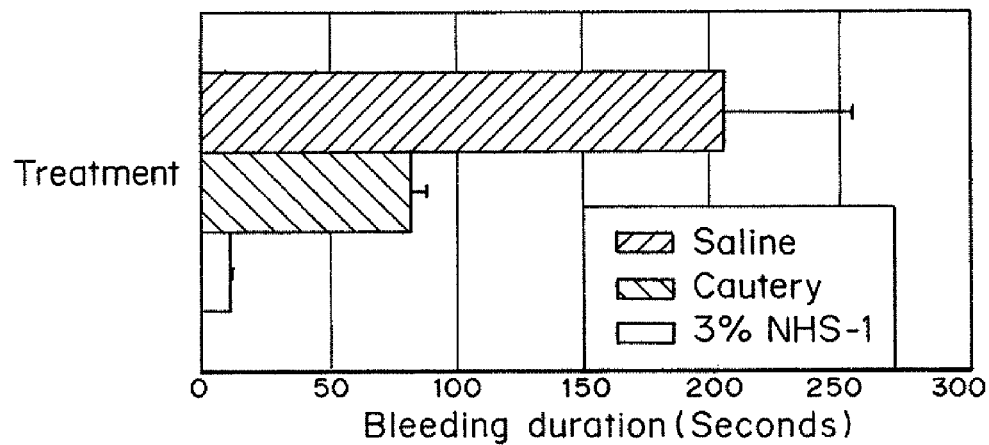

In the third experiment using adult rats (n=45) 4 mm holes were punched through the left lateral lobe and then the area was treated with 3% NHS-1, saline or heat cautery to bring about hemostasis (FIG. 3b). In the experimental group (n=15) a solution of 3% NHS-1 was applied after injury and hemostasis was achieved in about 10 seconds, while the saline controls (n=15) took 3.5 minutes to stop bleeding. In the heat cautery control group (n=15) cessation of bleeding took more than 60 seconds, inclusive of applying heat to cauterize the inside surface of the punch. NHS-1 treated animals were allowed to survive for up to 6 months with no detrimental effect on the tissues. Using ANOVA there was a significant difference between the 3% NHS-1 treatment and the controls (p<0.0001). In addition, the Tukey test showed that each group was significantly different from the other with a 99% confidence interval.

Example 5

Hemostasis in Skin Punch Biopsies

Figure 3C:
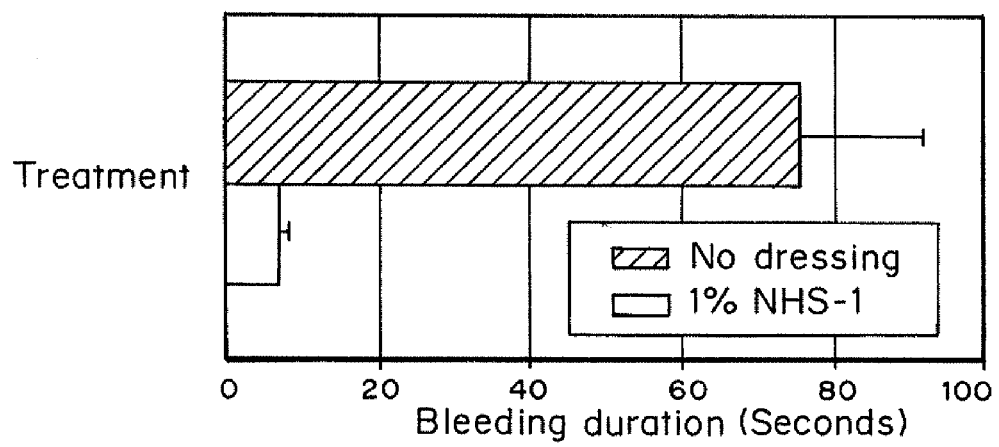
Figure 3D:
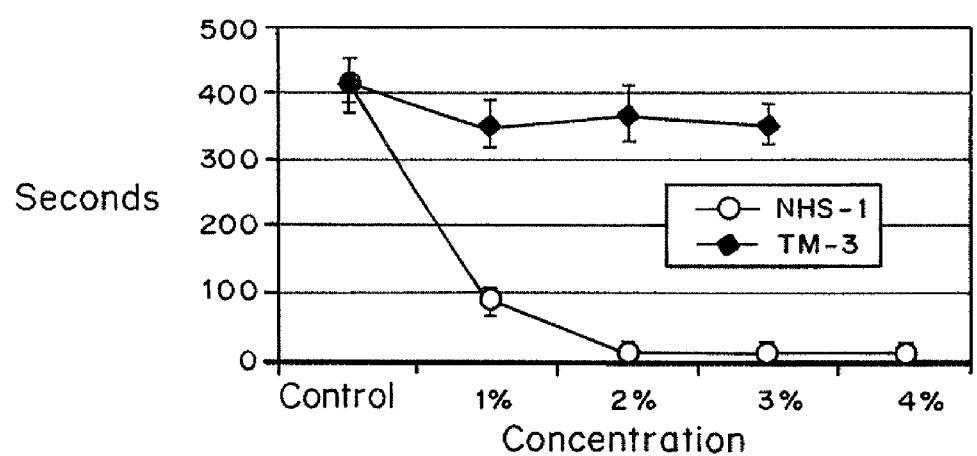

Six 4 mm punch biopsies were made on the back of anesthetized adult nude mice (n=23) for a total of 138 punches into the skin. Three punches were treated with 1% NHS-1 solution and the other three were left untreated, except for dabbing with cotton every 15 seconds until bleeding stopped. Punched wounds that bled for less than 10 seconds were excluded from the experiment. A solution of 1% NHS-1 was applied ten seconds after injury (n=23) and hemostasis took less than 10 seconds; the controls (n=23) continued to bleed for over 60 seconds (FIG. 3c). The bleeding times were averaged for each side of the animal and the Student t test for paired samples showed a significant difference between the treatment and control side of the animal (p<0.0001).

Example 6

Comparison of Three Different Materials

To learn more about the hemostatic properties and mechanism of action of NHS-1 (RADA-16) (SEQ ID NO: 60), both the sagittal and transverse liver experiments were repeated, comparing them with two additional materials that are known to self-assemble and spontaneously form nanofibers: 1) RADA-12 (NHS-2), a sequence variation of NHS-1 and 2) EAK-16 (TM-3), a different sequence in the same family of self-assembling peptides used to determine if the material's length and stiffness altered its hemostatic effectiveness in bleeding models.

Making a sagittal liver cut in adult rats (n=9) 100 μl of 2% NHS-2 solution was applied to the wound and bleeding stopped in less than 10 seconds. In the cautery controls (n=3) bleeding continued for more than 90 seconds (p<0.0001). Repeating the experiment in adult rats (n=8) using 100 μl of 2% TM-3 the material assembled but did not achieve hemostasis; the animals continued to bleed until the experiment was terminated after more than 3 minutes.

The increased blood flow from the portal vein after making a transverse liver cut allowed the performance of another dose response experiment where various concentrations of NHS-1 (1% to 4%) and TM-3 (1% to 3%) could be compared with controls (FIG. 3d). All concentrations of NHS-1 were effective; however the higher blood pressure and flow rate after the transverse liver cut required a concentration of 2% or higher of NHS-1 to stop bleeding in less than 15 seconds.

Example 7

Interface of NHS-1 and Tissues

Still looking for mechanism clues as well as further understanding of the relationship of the NHS-1 blood/tissue interface in both the brain and liver, the treated tissues were examined under the transmission electron microscope (TEM), to determine how the red blood cells (RBCs), platelets, tissue and the ECM interact with the material.

A 1% NHS-1 solution was applied to a liver wound and immediately harvested the tissue. In the electron micrograph the hepatocyte and RBC looks to be intact with the assembled NHS-1 at the interface. When applied shortly after injury, the material appeared to stop the movement of blood from the vessels without detrimental effects to the liver's RBCs; there was also no evidence of lysing. Furthermore, there was no evidence of platelet aggregation at the blood/NHS-1 interface when samples were taken at various time points after treatment.

A very tight interaction between NHS-1 and the neural tissue was found in the brain. No RBCs and no evidence of platelet aggregation were observed in the assembled NHS-1. The RBCs that were present appeared intact at the edges of the assembled NHS-1 with no evidence of lysing. Furthermore, no evidence of thrombi was observed in the brain, lung, or liver of the NHS-1 and NHS-2 treated animals.

NHS-1 and NHS-2 are synthetic, biodegradable and do not contain any blood products, collagens or biological contaminants that may be present in human or animal-derived hemostatic agents, like fibrin glue. They can be applied directly onto, or into, a wound without the worry of the material expanding, reducing the problem of secondary tissue damage as well as the problems caused by constricted blood flow. In our brain studies evidence of the production of prion-like substances or fibril tangles in animals that had the material implanted in their brain for up to six months, was investigated. None was found. Furthermore, the breakdown products of NHS-1 are amino acids which may be used as tissue building blocks for the repair of the injury. Independent third-party testing of the material found no pyrogenicity, which has been found with some other hemostatic agents, and no systemic coagulation or other safety issues in animals. These data demonstrate that hemostasis can be achieved in less than 15 seconds in multiple tissues as well as a variety of different wounds.

The NHS-1 and NHS-2 solutions easily filled in and conformed to the irregular shapes of the wounds before assembling, as shown in the electron micrographs. This tight contact is believed to play a role in the hemostatic action because of the size of the self-assembling peptide units. The micrographs also showed that the material does not cause the RBCs to lyse appearing to protect them from normal degradation when exposed to the air.

The observed hemostasis cannot be explained by gelation kinetics. One would think that a stiffer gel would be more effective for higher pressure bleeders; however the opposite was found to be true. TM-3, which is from the same family of peptides as NHS-1 and NHS-2, and is the stiffest of the three self-assembling peptides tested, did not arrest bleeding; it fractured at the tissue interface and within the resultant gel. TM-3 may have fractured due to 1) the pulsations of the liver and 2) the inability of the material to flex with the tissue as blood pumped through the organ. This is similar to the fracturing of an artery when grown in a laminar flow environment and then transplanted to a pulsed environment. The cells line up along the direction of flow, unlike the natural helical coil 36-39 seen in a pulsed environment, which allows for expansion and contraction, without splitting, as blood moves though the artery. Conversely, NHS-1 and NHS-2 were able to flex with the tissue.

Finally, NHS-2, the least stiff of the three materials, appeared to perform the same as NHS-1 most likely due to their similar structure and modulus.

With this discovery the speed of hemostasis will fundamentally change how much blood is needed during surgery of the future. As much as 50% of surgical time can be spent packing wounds to reduce or control bleeding. The NHS solutions may represent a step change in technology and could revolutionize bleeding control during surgery and trauma; however they need to be clinically tested for use in humans.

Those skilled in the art will recognize, or be able to ascertain using no more than routine experimentation, many equivalents to the specific embodiments described herein. Such equivalents are intended to be encompassed by the following claims.

We claim:

1. A method for treatment of disorders involving leaky or damaged tight junctions and weak, diseased, or injured extracellular matrix comprising
administering to a human in need thereof a formulation comprising self-assembling peptides, wherein the self-assembling peptides consist of a sequence of from 8 to 16 amino acid residues conforming to one or more of Formulas I-IV:

$$((Xaa^{neu}-Xaa^{+})_x(Xaa^{neu}-Xaa^{-})_y)_n \quad (I)$$

$$((Xaa^{neu}-Xaa^{-})_x(Xaa^{neu}-Xaa^{+})_y)_n \quad (II)$$

$$((Xaa^{+}-Xaa^{neu})_x(Xaa^{-}-Xaa^{neu})_y)_n \quad (III)$$

$$((Xaa^{-}-Xaa_{neu})_x((Xaa^{+}-Xaa^{neu})_y)_n \quad (IV)$$

wherein $Xaa^{neu}$ represents alanine; $Xaa^{+}$ represents arginine or lysine; $Xaa^{-}$ represents aspartic acid or glutamic acid; x and y are integers having a value of 1 or 2, or 3, or 4, independently; and n is an integer having a value of 14,
wherein the formulation has a total concentration of less than 5 mM Li+, Na+, K+, and Cs+ ions and a concentration of self-assembling peptides between 1.0% weight to volume and 4.0% weight to volume, inclusive,
wherein the formulation is administered into a site selected from the group consisting of the blood stream and the interior of the intestines, and
wherein the self-assembling peptides assemble within the paracellular spaces between cells having leaky or damaged tight junctions and weak, diseased, or injured extracellular matrix,
and wherein the amount and concentration of self-assembling peptides is effective to form a barrier structure to prevent or limit the movement of blood and bodily fluids through leaky or damaged tight junctions and weak, diseased, or injured extracellular matrix.

2. The method of claim 1, wherein the formulation further comprises a pharmaceutically acceptable carrier for administration in the body.

3. The method of claim 2, wherein the formulation comprises a dry powder, a wafer, a disk, a tablet, a capsule, a liquid, a gel, nano or microparticles, a polymeric matrix, or a polymeric or fibrous structure.

4. The method of claim 1, wherein x and y are 1 and n is 4.

5. The method of claim 1, wherein the self-assembling peptides comprise a sequence of amino acid residues conforming to Formula III or Formula IV.

6. The method of claim 1, wherein the self-assembling peptides comprise the amino acid sequence RADARADARADARADA (SEQ ID NO: 60).

7. The method of claim 1, wherein the amino acid residues are naturally occurring amino acid residues.

8. The method of claim 7, wherein the naturally occurring amino acid residues are suitable for cell growth and repair.

9. The method of claim 1 for the treatment and support of intestinal walls.

10. The method of claim 1 for the treatment and support of tubular structures such as urethra, intestine, veins, arteries, bile ducts.

11. The method of claim 1 for the treatment of necrotic tissue or damaged tissue in stomach.

12. The method of claim 1, wherein the peptide is administered into the blood stream.

13. The method of claim 1, wherein the composition is administered in an amount sufficient to provide a reservoir of self-assembling peptides within the body to provide self-assembling material as needed throughout the flowing system.

14. The method of claim 9, wherein the formulation is injected or otherwise introduced into the interior of an organ.

* * * * *